(12) United States Patent
Beim et al.

(10) Patent No.: US 9,836,577 B2
(45) Date of Patent: Dec. 5, 2017

(54) METHODS AND DEVICES FOR ASSESSING RISK OF FEMALE INFERTILITY

(71) Applicant: Celmatix, Inc., New York, NY (US)

(72) Inventors: Piraye Yurttas Beim, New York, NY (US); Michael Elashoff, Redwood City, CA (US)

(73) Assignee: Celmatix, Inc., New York, NY (US)

( * ) Notice: Subject to any disclaimer, the term of this patent is extended or adjusted under 35 U.S.C. 154(b) by 0 days.

(21) Appl. No.: 14/605,452

(22) Filed: Jan. 26, 2015

(65) Prior Publication Data

US 2015/0142331 A1    May 21, 2015

Related U.S. Application Data

(63) Continuation-in-part of application No. 14/107,800, filed on Dec. 16, 2013.

(60) Provisional application No. 61/932,226, filed on Jan. 27, 2014, provisional application No. 61/889,738, filed on Oct. 11, 2013, provisional application No. 61/737,693, filed on Dec. 14, 2012.

(51) Int. Cl.
| | |
|---|---|
| G01N 33/48 | (2006.01) |
| G06F 19/18 | (2011.01) |
| C12Q 1/68 | (2006.01) |
| G06F 19/00 | (2011.01) |
| G06G 7/58 | (2006.01) |

(52) U.S. Cl.
CPC .......... G06F 19/18 (2013.01); C12Q 1/6827 (2013.01); C12Q 1/6883 (2013.01); G06F 19/3431 (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 5,510,270 A | 4/1996 | Fodor et al. | |
| 5,539,083 A | 7/1996 | Cook et al. | |
| 5,556,752 A | 9/1996 | Lockhart et al. | |
| 5,578,832 A | 11/1996 | Trulson et al. | |
| 6,028,189 A | 2/2000 | Blanchard | |
| 6,214,558 B1 | 4/2001 | Shuber et al. | |
| 6,300,077 B1 | 10/2001 | Shuber et al. | |
| 6,566,101 B1 | 5/2003 | Shuber et al. | |
| 6,818,395 B1 | 11/2004 | Quake et al. | |
| 6,890,763 B2 | 5/2005 | Jackowski et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,282,337 B1 | 10/2007 | Harris | |
| 7,323,305 B2 | 1/2008 | Leamon et al. | |
| 7,335,762 B2 | 2/2008 | Rothberg et al. | |
| 7,531,635 B2 | 5/2009 | Nelson et al. | |
| 7,666,593 B2 | 2/2010 | Lapidus | |
| 9,177,098 B2 | 11/2015 | Elashoff et al. | |
| 2002/0164629 A1 | 11/2002 | Quake et al. | |
| 2005/0214836 A1 | 9/2005 | Nakamura et al. | |
| 2006/0172322 A1 | 8/2006 | Nakabayashi et al. | |
| 2006/0195269 A1 | 8/2006 | Yeatman et al. | |
| 2009/0026082 A1 | 1/2009 | Rothberg et al. | |
| 2009/0127589 A1 | 5/2009 | Rothberg et al. | |
| 2009/0137478 A1 | 5/2009 | Bernstein et al. | |
| 2009/0156412 A1 | 6/2009 | Boyce, IV et al. | |
| 2009/0191565 A1 | 7/2009 | Lapidus et al. | |
| 2010/0035252 A1 | 2/2010 | Rothberg et al. | |
| 2010/0036192 A1 | 2/2010 | Yao et al. | |
| 2010/0081135 A1 | 4/2010 | Dorak et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0071033 A1 | 3/2011 | Yurttas et al. | |
| 2011/0166029 A1 | 7/2011 | Margulies et al. | |
| 2012/0094845 A1 | 4/2012 | Yurttas et al. | |
| 2013/0109583 A1 | 5/2013 | Beim | |
| 2014/0107934 A1 | 4/2014 | Elashoff et al. | |
| 2014/0171337 A1 | 6/2014 | Beim | |

(Continued)

FOREIGN PATENT DOCUMENTS

| | | |
|---|---|---|
| EP | 1484399 A1 | 12/2004 |
| EP | 1947195 A1 | 7/2008 |

(Continued)

OTHER PUBLICATIONS

Talkowski, 2012, Sequencing Chromosomal Abnormalities Reveals Neurodevelopmental Loci that Confer Risk across Diagnostic Boundaries, Cell 149:525-37.
Tanwar, 2008, "In vivo evidence of role of bone morphogenetic protein-4 in the mouse ovary," Anim Reprod Sci 106 (3-4):232-40.
Teixeira Filho, 2002, "Aberrant expression of growth differentiation factor-9 in oocytes of women with polycystic ovary syndrome," J Clin Endocrinol Metab 87(3):1337-44.
Telford, 1990, Transition from maternal to embryonic control in early mammalian development: a comparison of several species, Mol Reprod Dev 26:90-100.
Thompson, 1998, Mouse embryos do not wait for the MBT: chromatin and RNA polymerase remodeling in genome activation at the onset of development, Dev Genet 22:31-42.
Tian, 2009, Evolution and functional divergence of NLRP genes in mammalian reproductive systems, BMC Evol Biol 9:202.
Tian, 2009, Gene Birth, Death, and Divergence: The Different Scenarios of Reproduction Related Gene Evolution, Biology of Reproduction 80:616-21.
Tokushige, 2006, High density of small nerve fibres in the functional layer of the endometrium in women with endometriosis, Human Reproduction 21(3):782-87.
Tong, 1999, "A mouse gene encoding an oocyte antigen associated with autoimmune premature ovarian failure," Endocrinology 140(8):3720-6.

(Continued)

*Primary Examiner* — Eric S Dejong

(74) *Attorney, Agent, or Firm* — Brown Rudnick LLP; Thomas C. Meyers

(57) ABSTRACT

The invention generally relates to methods and devices for assessing risk of female infertility. In certain aspects, methods of the invention involve obtaining a sample, conducting an assay on at least one infertility-associated biomarker, and assessing risk to the patient of developing early-onset decrease in fertility based upon results of the assay.

18 Claims, 15 Drawing Sheets

(56) References Cited

U.S. PATENT DOCUMENTS

| | | | |
|---|---|---|---|
| 2014/0186839 A1 | 7/2014 | Margulies et al. | |
| 2014/0337052 A1 | 11/2014 | Pellini et al. | |
| 2015/0142331 A1 | 5/2015 | Beim et al. | |
| 2015/0211068 A1 | 7/2015 | Beim et al. | |
| 2016/0017426 A1 | 1/2016 | Beim et al. | |
| 2016/0078172 A1 | 3/2016 | Elashoff et al. | |

FOREIGN PATENT DOCUMENTS

| | | |
|---|---|---|
| JP | 2004-533229 A | 11/2004 |
| WO | 2001/005935 A2 | 1/2001 |
| WO | 2001/05935 A2 | 1/2001 |
| WO | 2002/081492 A1 | 10/2002 |
| WO | 03/011326 A1 | 2/2003 |
| WO | 2006/055761 A1 | 5/2006 |
| WO | 2008/109147 A2 | 9/2008 |
| WO | 2009/109043 A1 | 9/2009 |
| WO | 2010/147714 A1 | 12/2010 |
| WO | 2011031786 A2 | 3/2011 |
| WO | 2011/133175 A1 | 10/2011 |
| WO | 2013/052505 A2 | 4/2013 |
| WO | 2014/062393 A1 | 4/2014 |
| WO | 2015/112972 A1 | 7/2015 |
| WO | 2016011377 A1 | 1/2016 |

OTHER PUBLICATIONS

Tong, 2000, "Mater encodes a maternal protein in mice with a leucine-rich repeat domain homologous to porcine ribonuclease inhibitor," Mamm Genome 11(4):281-7.
Tong, 2000, "Mater, a maternal effect gene required for early embryonic development in mice," Nat Genet 26(3):267-8.
Tong, 2002, "A human homologue of mouse Mater, a maternal effect gene essential for early embryonic development," Hum Reprod 17(4):903-11.
Tong, 2004, "Developmental expression and subcellular localization of mouse MATER, an oocyte-specific protein essential for early development," Endocrinology 145(3):1427-34.
Toralova, 2009, "Silencing CENPF in bovine preimplantation embryo induces arrest at 8-cell stage," Reproduction 138 (5):783-91.
Tormala, 2008, Zona pellucida components are present in human fetal ovary before follicle formation, Mol Cell Endocrinol 289(1-2):10-15.
Tschopp, 2003, NALPs: a novel protein family involved in inflammation, Nature Rev Molec Cell Biol 4:95-104.
Uda, 2004, "Foxl2 disruption causes mouse ovarian failure by pervasive blockage of follicle development," Hum Mol Genet 13(11):1171-81.
Uhlenhaut, 2006, "Foxl2 function in ovarian development," Mol Genet Metab 88(3):225-34.
Underwood, 1998, "A novel calcium-independent phospholipase A2, cPLA2-gamma, that is prenylated and contains homology to cPLA2," J Biol Chem 273(34):21926-32.
van Monffoort et al., 2008, "Differential gene expression in cumulus cells as a prognostic indicator of embryo viability: a rnicroarray analysis," HMR-Basic Science of Reproductive Medicine, 14(3):157-168.
Vatansever, 2005, "Changed Bcl:Bax ratio in endometrium of patients with unexplained infertility," Acta Histochem 107 (5):345-55.
Velasco, 1999, Cloning and Characterization of Human MMP-23, a New Matrix Metalloproteinase Predominantly Expressed in Reproductive Tissues and Lacking Conserved Domains in Other Family Members, Journal of Biological Chemistry 274:4570-76.
Velculescu, 1995, Serial analysis of gene expression, Science 270:484-87.
Velculescu, 1997, Characterization of the Yeast Transcriptome, Cell, 88:243 51.

Venners, 2006, "Urinary estrogen and progesterone metabolite concentrations in menstrual cycles of fertile women with non-conception, early pregnancy loss or clinical pregnancy," Human Reprod 21(9):2272-80.
Vernet, 1992, Changes in permissiveness for the expression of microinjected DNA during the first cleavages of mouse embryos, Mech Dev 36:129-39.
Vitale, 2007, "Proteomic profiling of murine oocyte maturation," Mol Reprod Dev 74(5):608-16.
Vitt, 2001, "Stage-dependent role of growth differentiation factor-9 in ovarian follicle development," Mol Cell Endocrinol 183(1-2)171-7.
Vogt, 2009, "Aurora kinase B, epigenetic state of centromeric heterochromatin and chiasma resolution in oocytes," Reprod Biomed Online 19(3):352-68.
Wan, 2008, "Maternal depletion of CTCF reveals multiple functions during oocyte and preimplantation embryo development," Development 135(16):2729-38.
Wang, 1996, "Purification and biochemical heterogeneity of the mammalian SWI-SNF complex," EMBO J 15(19):5370-82.
Wang, 2006, Search for basonuclin target genes, Biochemical and Biophysical Research Communications 348:1261-71.
Watkins, 2006, "An investigation into FOXE1 polyalanine tract length in premature ovarian failure," Mol Hum Reprod 12(3):145-9.
Weis, 1992, Detection of rare mRNAs via quantitative RT-PCR, Trends in Genetics 8:263-64.
Wilcoxon, 1945, "Individual comparisons by ranking methods," Biometrics Bulletin 1(6):80-83.
Wright, 2003, "ePAD, an oocyte and early embryo-abundant peptidylarginine deiminase-like protein that localizes to egg cytoplasmic sheets," Dev Biol 256(1):73-88.
Wu, 2003, "Zygote arrest 1 (Zar1) is a novel maternal-effect gene critical for the oocyte-to-embryo transition," Nat Genet 33(2):187-91.
Wu, 2009, "Maternal depletion of NLRP5 blocks early embryogenesis in rhesus macaque monkeys (Macaca mulatta)," Hum Reprod 24(2):415-24.
Xiao, 1999, "HSF1 is required for extra-embryonic development, postnatal growth and protection during inflammatory responses in mice," EMBO J 18(21):5943-52.
Yan, 2005, "Mice deficient in oocyte-specific oligoadenylate synthetase-like protein OAS1D display reduced fertility," Mol Cell Biol 25(11):4615-24.
Yang, 2001, "BADGE, BeadsArray for the Detection of Gene Expression, a High-Throughput Diagnostic Bioassay," Genome Res 11:1888-98.
Yang, 2008, "Towards a transgenic model of Huntington's disease in a non-human primate," Nature 453:921-24.
Yang, 2008, "Parental effect of DNA (Cytosine-5) methyltransferase 1 on grandparental-origin-dependent transmission ratio distortion in mouse crosses and human families," Genetics 178(1):35-45.
Yeung, 2001, "Principal component analysis for clustering gene expression data," Bioinformatics 17(9):763-74.
Youngson, 2011, A missense mutation in the transcription factor Foxo3a causes teratomas and oocyte abnormalities in mice, Mammalian Genome 22:235-48.
Yu & Bradley, 2001, "Mouse genomic technologies: engineering chromosomal rearrangements in mice," Nature Reviews Genetics 2:780-90.
Yurttas, 2008, "Role for PADI6 and the cytoplasmic lattices in ribosomal storage in oocytes and translational control in the early mouse embryo," Development 135(15):2627-36.
Yurttas, 2010, Use of proteomics to identify highly abundant maternal factors that drive the egg-to-embryo transition, Reproduction 139:809-23.
Zhang, 2005, "Localization of mitotic arrest deficient 1 (MAD1) in mouse oocytes during the first meiosis and its functions as a spindle checkpoint protein," Biol Reprod 72(1):58-68.
Zhang, 2007, Distinct sets of developmentally regulated genes that are expressed by human oocytes and human embryonic stem cells, Fertil Steril 87(3):677-90.

(56) References Cited

OTHER PUBLICATIONS

Oh, 1997, "Spindlin, a major maternal transcript expressed in the mouse during the transition from oocyte to embryo," Development 124:493-503.
Ohsugi, 2008, "Maternally derived FILIA-MATER complex localizes asymmetrically in cleavage-stage mouse embryos," Development 135(2):259-69.
Okuwaki, 2012, Function of homo- and hetero-oligomers of human nucleoplasmin/nucleophosmin family proteins NPM1, NPM2 and NPM3 during sperm chromatin remodeling, Nucleic Acids Res 40(11):4861-78.
Oliphant, 2002, "BeadArray Technology: Enabling an Accurate Cost-Effective Approach to High-Throughput Genotyping," Discovery of Markers for Disease, Biotechniques 32:s56-61.
Palmer, 1990, "Comparison of human ZFY and ZFX transcripts," Proc Natl Acad Sci U S A 87(5):1681-5.
Park, 2006, Genetic approach to identify critical factors for mouse early embryogenesis, Integrative Biosciences 10:41-47.
Parker & Barnes, 1999, mRNA: Detection by In Situ and Northern Hybridization, Methods in Molecular Biology 106:247-83.
Parry, 2011, Mutations Causing Familial Biparental Hydatidiform Mole Implicate C6orf221 as a Possible Regulator of Genomic Imprinting in the Human Oocyte, Am J Hum Genet 89(3):451-58.
Pasini, 2004, "Suz12 is essential for mouse development and for EZH2 histone methyltransferase activity," EMBO J 23(20):4061-71.
Patterson, 2003, "Proteomics: the first decade and beyond," Nat Genet Supplement 33:311-23.
Pavlik, 2011, Divergent effects of the 677C>T mutation of the 5,10-methylenetetrahydrofolate reductase (MTHFR) gene on ovarian responsiveness and anti-Müllerian hormone concentrations, Fertility and Sterility 95(7):2257-62.
Payer, 2003, "Stella is a maternal effect gene required for normal early development in mice," Curr Biol 13(23):2110-7.
Paynton, 1994, Polyadenylation and deadenylation of maternal mRNAs during oocyte growth and maturation in the mouse, Molecular Reproduction and Development 37.
Pease, 1994, Light-generated oligonucleotide arrays for rapid DNA sequence analysis, PNAS 91(11):5022-26.
Penny, 1996, "Requirement for Xist in X chromosome inactivation," Nature 379(6561):131-7.
Pittman, 2004, "Integrated modeling of clinical and gene expression information for personalized prediction of disease outcomes," PNAS 101(22):8431-36.
Pozzi, 2009, Maternal polymorphisms for methyltetrahydrofolate reductase and methionine synthetase reductase and risk of children with Down syndrome, Am J Obstet Gynecol 200(6):636.e1-6.
Prueitt, 2000, "Physical mapping of nine Xq translocation breakpoints and identification of XPNPEP2 as a premature ovarian failure candidate gene," Cytogenet Cell Genet 89(1-2):44-50.
Punnonen, 1996, "Increased levels of interleukin-6 and interleukin-10 in the peritoneal fluid of patients with endometriosis," Am J Obstet Gynecol 174(5):1522-6.
Rajkovic, 2002, "The ret finger protein-like 4 gene, Rfpl4, encodes a putative E3 ubiquitin-protein ligase expressed in adult germ cells," Mech Dev 112(1-2):173-7.
Rajkovic, 2004, "NOBOX deficiency disrupts early folliculogenesis and oocyte-specific gene expression," Science 305(5687)1157-9.
Rankin, 1999, "Abnormal zonae pellucidae in mice lacking ZP1 result in early embryonic loss," Development 126(17):3847-55.
Ratnam, 2002, "Dynamics of Dnmt1 methyltransferase expression and intracellular localization during oogenesis and preimplantation development," Dev Biol 245(2):304-14.
Rosenthal & Brown, 2007, "The mouse ascending: perspectives for human-disease models," Nature Cell Biology 9:993-99.
Roth, 1998, "Finding DNA regulatory motifs within unaligned noncoding sequences clustered by whole-genome mRNA quantitation," Nat Biotechnol 16:939-45.
Rucker, 2000, "Bcl-x and Bax regulate mouse primordial germ cell survival and apoptosis during embryogenesis," Mol Endocrinol 14(7):1038-52.
Ruczinski, 2003, Journal of Computational and Graphical Statistcs 12:475-512.
Sahoo, 2011, Microdeletion of Xq28 involving the AFF2 (FMR2) gene in two unrelated males with developmental delay, Am. J. Med. Genet. A 155A:3110-15.
Salih, 2008, Regulation of catechol O-methyltransferase expression in granulosa cells: a potential role for follicular arrest in polycystic ovary syndrome, Fertility and Sterility 89(5) Supplement:1414-21.
Sanger, 1977, DNA sequencing with chain-terminating inhibitors, Proc.National Academy of Science USA 74(12):5463-7.
Santini, 2003, "Evolutionary conservation of regulatory elements in vertebrate Hox gene clusters," Genome Research 13.6a:1111-22.
Santos, 2002, Dynamic Reprogramming of DNA Methylation in the Early Mouse Embryo, Dev Biol 241(1):172-82.
Saskova, 2008, "Aurora kinase A controls meiosis I progression in mouse oocytes," Cell Cycle 7(15):2368-76.
Sato et al., 2011, Characterization of porcine autism susceptibility candidate 2 as a candidate gene for the number of corpora lutea in pigs, Animal Reproduction Science 126:211-20.
Schena, 1995, Quantitative Monitoring of Gene Expression Patterns with a Complementary DNA Microarray, Science 270:467-70.
Schena, 1996, Parallel human genome analysis: Microarray-based expression monitoring of 1000 genes, PNAS 93:10614-19.
Schmidt, 2011, Prenatal vitamins, one-carbon metabolism gene variants, and risk for autism, Epidemiology 22(4):476-85.
Schneider-Gadicke, 1989, "ZFX has a gene structure similar to ZFY, the putative human sex determinant, and escapes X inactivation," Cell 57(7):1247-58.
Schultz, 1977, Biochemical studies of mammalian oogenesis: protein synthesis during oocyte growth and meiotic maturation in the mouse, Journal of Cell Science 24:167-94.
Schultz, 2002, The molecular foundations of the maternal to zygotic transition in the preimplantation embryo, Hum Reprod Update 8:323-31.
Schumann, 2011, Genome-wide association and genetic functional studies identify autism susceptibility candidate 2 gene (AUTS2) in the regulation of alcohol consumption, Proc. Natl. Acad. Sci. U.S.A. 108:7119-24.
Seydoux, 2006, Pathway to totipotency: lessons from germ cells, Cell 127:891-904.
Shalon, 1996, A DNA microarray system for analyzing cmopelx DNA samples using two-color fluorescent probe hybridization, Genome Res 6:639-45.
Sharan, 2004, "BRCA2 deficiency in mice leads to meiotic impairment and infertility," Development 131(1):131-42.
Soni & Meller, 2007, Progress toward ultrafast DNA sequencing using solid-state nanopores, Clin Chem 53: 1996-2001.
Soyal, 2000, "FIGalpha, a germ cell-specific transcription factor required for ovarian follicle formation," Development 127(21):4645-54.
Stanislawska-Sachadyn, 2010, The transcobalamin (TCN2) 776C>G polymorphism affects homocysteine concentrations among subjects with low vitamin B12 status, Eur J Clin Nutr 64(11):1338-43.
Sturn, 2002, "Genesis: cluster analysis of microarray data," Bioinformatics 18(1):207-08.
Suzumori, 2003, "RFPL4 interacts with oocyte proteins of the ubiquitin-proteasome degradation pathway," Proc Natl Acad Sci U S A 100(2):550-5.
Swanson, 2002, The rapid evolution of reproductive proteins, Nat Rev Genet 3:137-44.
Zhang, 2008, "Expression analysis of the NLRP gene family suggests a role in human preimplantation development," PLoS One 3(7):e2755.
Zhang, 2009, "Proteomic-based identification of maternal proteins in mature mouse oocytes," BMC Genomics 10:348.
Zhao, 2008, "Transcription factor FIGLA is mutated in patients with premature ovarian failure," Am J Hum Genet 82(6):1342-8.

(56) References Cited

OTHER PUBLICATIONS

Zheng, 2007, Oocyte-Specific Genes Affect Folliculogenesis, Fertilization, and Early Development, Semin Reprod Med 25(4):243-51.
Zheng, 2009, "Role of Filia, a maternal effect gene, in maintaining euploidy during cleavage-stage mouse embryogenesis," Proc Natl Acad Sci U S A 106(18):7473-8.
Zuccotti, 2008, Maternal Oct-4 is a potential key regulator of the developmental competence of mouse oocytes, BMC Dev Biol 8:97.
Zuccotti, 2009, "Oct-4 regulates the expression of Stella and Foxj2 at the Nanog locus:implications for the developmental competence of mouse oocytes," Hum Reprod 24(9):2225-37.
Zuccotti, 2009, Role of Oct-4 during acquisition of developmental competence in mouse oocyte, Reprod Biomed Online 19 Suppl 3:57-62.
Australian Patent Examination Report No. 1 for App. No. 2010351560, dated Apr. 22, 2014, 5 pages.
International Preliminary Report on Patentability for PCT/US10/50063, dated Oct. 23, 2012, 6 pages.
International Preliminary Report on Patentability for PCT/US12/58492, dated Jan. 23, 2013, 6 pages.
International Search Report and Written Opinion for PCT/US10/50063, dated Feb. 3, 2011, 9 pages.
International Search Report and Written Opinion for PCT/US12/58492, dated Jan. 24, 2013, 7 pages.
International Search Report and Written Opinion for PCT/US13/63381, dated Dec. 16, 2013, 10 pages.
Supplementary European Search Report for EP10850395.4, dated Sep. 2, 2013.
Sha, G., et al. "Differentially expressed genes in human endometrial endothelial cells derived from eutopic endometrium of patients with endometriosis compared with those from patients without endometriosis." Human reproduction 22.12 (2007): 3159-3169.
Crispi, Stefania, et al. "Transcriptional profiling of endometriosis tissues identifies genes related to organogenesis defects." Journal of cellular physiology 228.9 (2013): 1927-1934.
Eyster, Kathleen M., et al. "Whole genome deoxyribonucleic acid microarray analysis of gene expression in ectopic versus eutopic endometrium." Fertility and sterility 88.6 (2007): 1505-1533.
Hever, Aniko, et al. "Human endometriosis is associated with plasma cells and overexpression of B lymphocyte stimulator." Proceedings of the National Academy of Sciences 104.30 (2007): 12451-12456.
Hull, M. Louise, et al. "Endometrial-peritoneal interactions during endometriotic lesion establishment." The American journal of pathology 173.3 (2008): 700-715.
Talbi, S., et al. "Molecular phenotyping of human endometrium distinguishes menstrual cycle phases and underlying biological processes in normo-ovulatory women." Endocrinology 147.3 (2006): 1097-1121.
International Search Report and Written Opinion for PCT/US15/40947 dated Nov. 2, 2015 (15 pages).
Nassieri et al. Elevated Day 3 Serum Follicle Stimulating Hormone And/Or Estradiol May Predict Fetal Aneuploidy. Ferility and Sterility. Apr. 1999, vol. 71, No. 4, pp. 715-718.
International Search Report and Written Opinion for PCT/US2015/012887 dated Jun. 24, 2015 (16 pages).
Crackower et al., 2003, Essential Role of Fkbp6 in Male Fertility and Homologous Chromosome Pairing in Meiosis, Science 300(5623): 1291-1295.
O'Bryan et al, 2006, Mouse models for genes involved in impaired spermatogenesis, International Journal of Andrology, 29(1): 76-88.
Yatsenko et al, 2010, The power of mouse genetics to review study spermatogenesis, J. Androl., 31(1): 34-44.
Yurttas et al, 2013, Personalized reproductive medicine on the brink: progress, opportunities and challenges ahead, Reproductive BioMedicine Online 27: 611-623.
Freudenberg et al, 2002, A similarity-based method for genome-wide prediction of disease-relevant human genes, Bioinformatics, Suppl 2:S110-5.
Ford et al., Mutation Res., vol. 313, p. 153-164 (1994).
International Search Report and the Written Opinion of the International Searching Authority for PCT/US13/63381, dated Dec. 16, 2013, 11 pages.
Ertunce et al., Human Reproduction vol. 20, No. 8 pp. 2157-2161, 2005.
International Search Report for Application No. PCT/US2012/58492 dated Jan. 24, 2013.
Lyall et al., Association Between Ovulation Inducing Drug Use, Infertility, and Autism Spectrum Disorders in the Nurses' Health Study II. Meeting for Autism Research: International Society for Autism Research. May 20, 2010, Retrieved on 213—Dec. 2012.
Lyall et al., Autism Dev Disord (2011)41:618-627, published online Aug. 10, 2010.
Rupp & Locker, 1987, "Purification and analysis of RNA from paraffin-embedded tissues," Biotechniques 6(1):56-60.
Dong, 1996, "Growth differentiation factor-9 is required during early ovarian folliculogenesis," Nature 383(6600):531-5.
Doolin, 2002, Maternal Genetic Effects, Exerted by Genes Involved in Homocysteine Remethylation Influence, Am J of Human Genet 71(5):1222-26.
Dube, 1998, "The bone morphogenetic protein 15 gene is X-linked and expressed in oocytes," Mol Endocrinol 12 (12):1809-17.
Egholm, 1993,PNA hybridizes to complementary oligonucleotides obeying the Watson—Crick hydrogen-bonding rules, Nature 365:566-68.
Eisen, 1998, "Cluster analysis and display of genome-wide expression patterns," PNAS 95(25):14863-68.
Elnakat & Ratnam, 2006, Role of folate receptor genes in reproduction and related cancers, Frontiers in Bioscience 11:506-19.
Ertunc, 2005, Glutathione-S-transferase P1 gene polymorphism and susceptibility to endometriosis, Human Reprod 20(8):2157-61.
Esposito, 2007, "Peptidylarginine deiminase (PAD) 6 is essential for oocyte cytoskeletal sheet formation and female fertility," Mol Cell Endocrinol 273(1-2):25-31.
Evans, 2008, "Prokineticin 1 signaling and gene regulation in early human pregnancy," Endocrinology 149(6):2877-87.
Ferguson, 1996, High-Density Fiber-Optic DNA Random Microsphere Array, Nature Biotech. 14:1681-84.
Ferguson, 2000, High-Density Fiber Optic DNA Random Microsphere Array, Analytical Chemistry 72:5618.
Fodor, 1991, Light-directed, spatially addressable parallel chemical synthesis, Science 251:767-773.
Fogli, 2003, "Ovarian failure related to eukaryotic initiation factor 2B mutations," Am J Hum Genet 72(6):1544-50.
Friedman, 1937, "The use of ranks to avoid the assumption of normality implicit in the analysis of variance," J Amer Stat Assoc 32(200):675-701.
Froehler, 1986, Synthesis of DNA via deoxynudeoside H-phosphonate Intermediates, Nucleic Acids Res 14:5399-5407.
Fu, 2010, Clathrin recruits phosphorylated TACC3 to spindle poles for bipolar spindle assembly and chromosome alignment, J. Cell. Sci. 123:3645-51.
Fujimoto, 2010, Highdensity lipoprotein metabolism and the human embryo, Human Reproduction Update 16, 25 20-38.
Fukumura, 2003, A sensitive transcriptome analysis method that can detect unknown transcripts, Nucl. Acids. Res. 31(16):e94.
Galan-Caridad, 2007, "Zfx controls the self-renewal of embryonic and hematopoietic stem cells," Cell 129(2):345-57.
Galloway, 2000, "Mutations in an oocyte-derived growth factor gene (BMP15) cause increased ovulation rate and Infertility in a dosage-sensitive manner," Nat Genet 25(3):279-83.
Garcia-Cruz, 2009, "ATR, BRCA1 and gammaH2AX localize to unsynapsed chromosomes at the pachytene stage in human oocytes," Reprod Biomed Online 18(1):37-44.
Genuis, 2012, J of Environmental & Public Health, article ID 185731, 10 pages.
Gonzalo, 2006, DNA methyltransferases control telomere length and telomere recombination in mammalian cells, Nat. Cell Biol. 8:416-24.
Greenfeld, 2007, "BAX is involved in regulating follicular growth, but is dispensable for follicle atresia in adult mouse ovaries," Reproduction 133(1):107-16.

(56) References Cited

OTHER PUBLICATIONS

Greenfeld, 2007, "BAX regulates follicular endowment in mice," Reproduction 133(5):865-76.
Grigorova, 2007, "Haplotype structure of FSHB, the beta-subunit gene for fertility-associated follicle-stimulating hormone:possible influence of balancing selection," Ann Hum Genet 71(Pt 1):18-28.
Gurtu, 2002, "Maternal effect for DNA mismatch repair in the mouse," Genetics 160(1):271-7.
Guzman, 2006, Cystathionine beta-synthase is essential for female reproductive function, Hum Mol Genet 15(21):3168-76.
Halperin, 2008, "Prolactin signaling through the short form of its receptor represses forkhead transcription factor FOXO3 and its target gene galt causing a severe ovarian defect," Mol Endocrinol 22(2):513-22.
Hao, 2002, "TACC3 expression and localization in the murine egg and ovary," Mol Reprod Dev 63(3):291-9.
Hardison, 1997, Long human-mouse sequence alignments reveal novel regulatory elements: a reason to sequence the mouse genome, Genome Res 7:959-66.
Hardouin & Nagy, 2000, Mouse models for human disease, Clinical Genetics 57(4):237-44.
Harris, 2005, "INHA promoter polymorphisms are associated with premature ovarian failure," Mol Hum Reprod 11(11):779-84.
Harris, 2008, Single-Molecule DNA Sequencing of a Viral Genome, Science 320:106-109.
Hawkins, 2011, Functional MicroRNA Involved in Endometriosis, Molecular Endocrinology 25(5):821-32.
Heid, 1996, Real Time Quantitative PCR, Genome Research 6:986-994.
Herr, 2008, "Distribution of RNA binding protein MOEP19 in the oocyte cortex and early embryo indicates pre-patterning related to blastomere polarity and trophectoderm specification," Dev Biol 314(2):300-16.
Hirasawa, 2008, Maternal and zygotic Dnmt1 are necessary and sufficient for the maintenance of DNA methylation imprints during preimplantation development, Genes Dev 22(12):1607-16.
Hod, 1992, A simplified ribonuclease protection assay, Biotechniques 13(6):852-54.
Hollingsworth, 2004, Mucins in cancer: protection and control of the cell surface, Nature Rev Cancer 4(1):45-60.
Horn, 1995, "A member of the caudal family of homeobox genes maps to the X-inactivation centre region of the mouse and human X chromosomes," Hum Mol Genet 4(6):1041-7.
Howe, 2011, "Limitation of inverse probability-of-censoring weights in estimating survival in the presence of strong selection bias," Am J Epidmiology 173:569-77.
Howell, 2001, "Genomic imprinting disrupted by a maternal effect mutation in the Dnmt1 gene," Cell 104(6):829-38.
Hu, 2007, "p53 regulates maternal reproduction through LIF," Nature 450(7170):721-4.
Hu, 2008, "p53:a new player in reproduction," Cell Cycle 7(7):848-52.
Hu, 2010, FIGLA, a Basic Helix-Loop-Helix Transcription Factor, Balances Sexually Dimorphic Gene Expression in Postnatal Oocytes, Mol Cell Biol, 30(14):3661-67.
Huber, 2004, matchprobes: a Bioconductor package for the sequence-matching of microarray probe elements, Bioinformatics 20(10):1651-52.
Hughes, 2001, Expression profiling using microarrays fabricated by an ink-jet oligonucleotide synthesizer, Nat Biotech 19:342-47.
Huntriss, 2002, "Isolation, characterization and expression of the human Factor in the Germline alpha (FIGLA) gene in ovarian follicles and oocytes," Mol Hum Reprod 8(12):1087-95.
Huntriss, 2006, "cDNA cloning and expression of the human NOBOX gene in oocytes and ovarian follicles," Mol Hum Reprod 12(5):283-9.
Abrams, 1997, Cognitive, behavioral, and neuroanatomical assessment of two unrelated male children expressing FRAXE, Am. J. Med. Genet. 74:73-81.
Agarwal, 2003, Role of reactive oxygen species in the pathophysiology of human reproduction, Fertility and Sterility 79(4):829-43.
Allingham-Hawkins, 1999, "Fragile X premutation is a significant risk factor for premature ovarian failure: The International collaborative POF in fragile X study—preliminary data," Am J Med Genet 83:322-25.
Amano, 2006, "Identification and targeted disruption of the mouse gene encoding ESG1 (PH34/ECAT2/DPPA5)," BMC Dev Biol 6:11, 9 pages.
Andersson, 2007, "Distinct and cooperative roles of mammalian Vg1 homologs GDF1 and GDF3 during early embryonic development," Dev Biol 311(2):500-11.
Aoki, 1997, Regulation of transcriptional activity during the first and second cell cycles in the preimplantation mouse embryo, Dev Biol 181:296-307.
Arnhold, 2009, "Inactivating mutations of luteinizing hormone beta-subunit or luteinizing hormone receptor cause oligo-amenorrhea and infertility in women," Horm Res 71(2):75-82.
Bachvarova, 1981, Synthesis, turnover, and stability of heterogeneous RNA in growing mouse oocytes, Dev Biol 86:384-92.
Barlow, 1998, "Atm deficiency results in severe meiotic disruption as early as leptonema of prophase I," Development 125(20):4007-17.
Bayne, 2004, "Increased expression of the FIGLA transcription factor is associated with primordial follicle formation in the human fetal ovary," Mol Hum Reprod 10(6):373-81.
Bedell, 1997, "Mouse models of human disease. Part I: Techniques and resources for genetic analysis in mice," Genes and Development 11:1-10.
Bedogni, 2010, Tbr1 regulates regional and laminar identity of postmitotic neurons in developing neocortex, Proceedings of the National Academy of Sciences 107:13129-34.
Benkhalifa, 2010, Imprinting: RNA expression for homocysteine recycling in the human oocyte, Fertility & Sterility 93(5) 1585-90.
Berker, 2009, Homocysteine concentrations in follicular fluid are associated with poor oocyte and embryo qualities in polycystic ovary syndrome patients undergoing assisted reproduction, Human Reproduction 24(9):2293-2302.
Bione, 1998, "A human homologue of the *Drosophila melanogaster* diaphanous gene is disrupted in a patient with premature ovarian failure:evidence for conserved function in oogenesis and implications for human sterility," Am J Hum Genet 62(3):533-41.
Blackburn, 2000, Metabolic Consequences of Adenosine Deaminase Deficiency in Mice Are Associated with Defects in Alveogenesis, Pulmonary Inflammation, and Airway Obstruction, Journal of Experimental Medicine 192:159-70.
Blanchard, 1996, High-density oligonucleotide arrays, Biosensors & Bioelectronics 11:687-90.
Blanchette, 2002, "Discovery of regulatory elements by a computational method for phylogenetic footprinting," Genome Res 12:739-48.
Bornstein, 2000, Thrombospondin 2 Modulates Collagen Fibrillogenesis and Angiogenesis, Journal of Investigative Dermatology Symposium Proceedings 5(1):61-66.
Borowczyk, 2009, Identification of a region of the DNMT1 methyltransferase that regulates the maintenance of genomic imprints, PNAS 106(49):20806-11.
Bottini, 2001, Autism: evidence of association with adenosine deaminase genetic polymorphism, Neurogenetics 3:111-13.
Bottini, 2002, Cooperative effect of adenosine deaminase and ABO-secretor genetic complex on susceptibility to childhood asthma, European Respiratory Journal 20:1613-15.
Braslavsky, 2003, Sequence information can be obtained from single DNA molecules, Proceedings of the National Academy of Sciences, (USA) 100:3960-4.
Brenner, 2000, Gene expression analysis by massively parallel signature sequencing (MPSS) on microbead arrays, Nature Biotechnology 18:630-34.
Brenner, 2002, Conserved regulation of the lymphocyte-specific expression of lck in the Fugu and mammals, PNAS 99:2936-41.
Bultman, 2000, "A Brg1 null mutation in the mouse reveals functional differences among mammalian SWI/SNF complexes," Mol Cell 6(6):1287-95.

(56) References Cited

OTHER PUBLICATIONS

Bultman, 2006, "Maternal BRG1 regulates zygotic genome activation in the mouse," Genes Dev 20(13):1744-54.
Burney, 2007, Gene Expression Analysis of Endometrium Reveals Progesterone Resistance and Candidate Susceptibility Genes in Women with Endometriosis, Endocrinology 148(8):3814-26.
Burns, 2003, Roles of NPM2 in chromatin and nucleolar organization in oocytes and embryos, Science 300:633-36.
Carabatsos, 1998, "Characterization of oocyte and follicle development in growth differentiation factor-9-deficient mice," Dev Biol 204(2):373-84.
Carlson, 1992, Properties and localization of DNA methyltransferase in preimplantation mouse embryos: implications for genomic imprinting, Genes Dev. 6:2536-41.
Cenarro, 2003, A common variant in the ABCA1 gene is associated with a lower risk for premature coronary heart disease in familial hypercholesterolaemia, Journal of Medical Genetics 40:163-68.
Chang, 2011, MUC4 gene polymorphisms associate with endometriosis development and endometriosis related infertility, BMC Med 9:19.
Chirgwin, 1979, Isolation of biologically active ribonucleic acid from sources enriched in ribonuclease, Biochemistry, 18:5294-99.
Chiu, 2008, Effects of Native Human Zona Pellucida Glycoproteins 3 and 4 on Acrosome Reaction and Zona Pellucida Binding of Human Spermatozoa, Biol Reprod 79(5):869-77.
Chong, 1993, "Preimplantation prevention of X-linked disease:reliable and rapid sex determination of single human cells by restriction analysis of simultaneously amplified ZFX and ZFY sequences," Hum Mol Genet 2(8):1187-91.
Christians, 1997, "Evidence for the involvement of mouse heat shock factor 1 in the atypical expression of the HSP70.1 heat shock gene during mouse zygotic genome activation," Mol Cell Biol 17(2):778-88.
Christians, 2000, "Maternal effect of Hsf1 on reproductive success," Nature 407(6805):693-4.
Christiansen-Weber, 2000, Functional Loss of ABCA1 in Mice Causes Severe Placental Malformation, Aberrant Lipid Distribution, and Kidney Glomerulonephritis As Well As High-Density Lipoprotein Cholesterol Deficiency, The American Journal of Pathology 157:1017.
Ciccone, 2009, "KDM1B is a histone H3K4 demethylase required to establish maternal genomic imprints," Nature 461(7262):415-8.
Cirio, 2008, "DNA methyltransferase 1o functions during preimplantation development to preclude a profound level of epigenetic variation," Dev Biol 324(1):139-50.
Collins, 2006, The Application of genomic and proteomic technoloies in predictive, preventive and personalized medicine, Vascular Pharmacology, Vascular Pharmacology 45(5):258-67.
Davidson, 2003, "Cdx4 mutants fail to specify blood progenitors and can be rescued by multiple hox genes," Nature 425(6955):300-6.
Davis, 1993, "A null c-myc mutation causes lethality before 10.5 days of gestation in homozygotes and reduced fertility in heterozygous female mice," Genes Dev 7(4):671-82.
De Andres, 1995, Improved Method for mRNA Extraction from Paraffin a Embedded Tissues, BioTechniques 18:42-44.
de Klein, 2000, "Targeted disruption of the cell-cycle checkpoint gene ATR leads to early embryonic lethality in mice," Curr Biol 10(8):479-82.
Dean, 1992, "Biology of mammalian fertilization:role of the zona pellucida," J Clin Invest 89(4):1055-9.
DeRisi, 1996, Use of a cDNA microarray to analyse gene expression patterns in human cancer, Nature Genetics 14:457-60.
Ding & Cantor, 2003, A high-throughput gene expression analysis technique using competitive PCR and matrix-assisted laser desorption ionization time-of-flight MS, PNAS 100(6):3059-64.
Dion, 2008, Dnmtl deficiency promotes CAG repeat expansion in the mouse germline, Human Molecular Genetics 17:1306-17.

Iglesias, 2008, "Expression pattern of glypican-3 (GPC3) during human embryonic and fetal development," Histol Histopathol 23(11):1333-40.
Ikeda, 2010, Expression of methylation pathway enzymes in bovine oocytes and preimplantation embryos, J of Exper Zoology Part A: Ecol Genet & Physiol 313A(3):129-36.
Irizarry, 2003, Exploration, normalization, and summaries of high density oligonucleotide array probe level data, Biostatistics 4(2):249-64.
Iuchi, 1999, Basonuclin, a zinc finger protein of keratinocytes and reproductive germ cells, binds to the rRNA gene promoter, Proc. Natl. Acad. Sci. U.S.A. 96:9628-32.
Jeddi-Tehrani, 2011, Analysis of Plasminogen Activator Inhibitor-1, Integrin Beta3, Beta Fibrinogen, and Methylenetetrahydrofolate Reductase Polymorphisms in Iranian Women with Recurrent Pregnancy Loss, Am J of Reprod Immunol 66(2):149-56.
Kanai, 1994, Rapid and simple method for preparation of genomic DNA from easily obtainable clotted blood, J Clin Pathol 47:1043-44.
Kang, 2009, "Single-nucleotide polymorphisms in the p53 pathway regulate fertility in humans," Proc Natl Acad Sci U S A 106(24):9761-6.
Kanka, 2003, Gene expression and chromatin structure in the pre-implantation embryo, Theriogenology 59:3-19.
Kao, 2003, "Expression profiling of endometrium from women with endometriosis reveals candidate genes for disease-based implantation failure and infertility," Endocrinology 144(7):2870-81.
Karolchik, 2008, "Comparative genomic analysis using the UCSC genome browser," Comparative Genomics (Humana Press), 17-33.
Kawai, 2012, Negative regulation of Odd-skipped related 2 by TGF-beta achieves the induction of cellular migration and the arrest of cell cycle, Biochem & Biophys Research Communications 421(4):696-700.
Kawamoto, 1999, "Expression profiling by iAFLP: a PCR-based method for genome-wide gene expression profiling," Genome Res 12:1305-12.
Kay, 1993, "Expression of Xist during mouse development suggests a role in the initiation of X chromosome inactivation," Cell 72(2):171-82.
Kim, 2008, SEBOX Is Essential for Early Embryogenesis at the Two-Cell Stage in the Mouse, Biol Reprod 79(6):1192-1201.
Komiyana, 2007, Local activation of TGF-beta1 at endometriosis sites, J Reprod Med 52(4):306-12.
Kononen, 1998, "Tissue microarrays for high-throughput molecular profiling of tumor specimens," Nat Med 4(7):844-47.
Kosaki, 2004, "Premature ovarian failure in a female with proximal symphalangism and Noggin mutation," Fertil Steril 81(4):1137-9.
Latham, 1992, Acquisition of a transcriptionally permissive state during the 1-cell stage of mouse embryogenesis, Dev Biol 149:457-62.
Lee, 2004, "Effects of bone morphogenetic protein-7 (BMP-7) on primordial follicular growth in the mouse ovary," Mol Reprod Dev 69(2):159-63.
Lefievre, 2004, "Four zona pellucida glycoproteins are expressed in the human," Hum Reprod 19(7):1580-6.
LeGouy, 1998, "Differential preimplantation regulation of two mouse homologues of the yeast SWI2 protein," Dev Dyn 212(1):38-48.
Leland, 2009, "Heterozygosity for a Bub1 mutation causes female-specific germ cell aneuploidy in mice," Proc Natl Acad Sci U S A 106(31):12776-81.
Li, 2008, "A subcortical maternal complex essential for preimplantation mouse embryogenesis," Dev Cell 15(3):416-25.
Liang & Pardee, 1992, Differential display of eukaryotic messenger RNA by means of the polymerase chain reaction, Science 257:967-71.
Lockhart, 1996, Expression monitoring by hybridization to high-density oligonucleotide arrays, Nature Biotechnology 14 (13):1675.
Loffler, 2003, "Etiology of ovarian failure in blepharophimosis ptosis epicanthus inversus syndrome:FOXL2 is a conserved, early-acting gene in vertebrate ovarian development," Endocrinology 144(7):3237-43.

(56) References Cited

OTHER PUBLICATIONS

Loughery, 2011, DNMT1 deficiency triggers mismatch repair defects in human cells through depletion of repair protein levels in a process involving the DNA damage response, Human Molecular Genetics 20:3241-55.
Lyall, 2010, "Association between ovulation inducing drug use, infertility, and autism spectrum disorders in the nurses' health study II," Meeting for Autism Research: International Society for Autism Research [Retrieved Dec. 23, 2012] from https://imfar.confex.com/imfar/2010/webprogram/Paper5541.html. Abstract.
Lyall, 2011, Maternal Ealry Life Factors Associated with Hormone Levels and the Risk of Having a Child with an Autism Spectrum Disorder in the Nurses Health Study II, J Autism Dev Disord 41:618-27.
Ma, 2006, "Basonuclin:a novel mammalian maternal-effect gene," Development 133(10):2053-62.
Ma, 2008, Histone deacetylase 1 (HDAC1) regulates histone acetylation, development, and gene expression in preimplantation mouse embryos, Dev Biol 319:110-20.
Maldonado-Perez, 2007, "Potential roles of the prokineticins in reproduction," Trends Endocrinol Metab 18(2).
Malizia, 2009, "Cumulative live-birth rates after in vitro fertilization," New England J Med 360:236-43.
Mannikko, 2005, Association between Sequence variations in genes encoding human zona pellucida glycoproteins and fertilization failure in IVF, Human Reproduction, 20(6):1578-1585.
Marguilies, 2005, "Genome sequencing in microfabricated high-density picolitre reactors," Nature 437:376-80.
Maskos & Southern, 1992, Oligonucleotide hybridisations on glass supports: a novel linker for oligonucleotide synthesis and hybridisation properties of oligonucleotides synthesised in situ, Nuc Acids Res 20:1679-84.
Matzuk, 2002, Genetic dissection of mammalian fertility pathways, Nature Cell Bio 4 Suppl:s41-49.
Maxam, 1977, A new method for sequencing DNA, Proc. of National Academy of Science USA 74:560-4.
McBride, 1983, An Investigation of Several Oeoxynucleoside Phosphoramidites Useful for Synthesizing Deoxyoligonucleotides, Tetrahedron Lett 24:245-48.
McCarthy, 2003, Loss of Bard1, the Heterodimeric Partner of the Brca1 Tumor Suppressor, Results in Early Embryonic Lethality and Chromosomal Instability, Molecular Cellular Biology 23(14):5056-63.
McKenzie, 2004, "Human cumulus granulosa cell gene expression: a predictor of ferilization and embryo selection in women undergoing IVF," Human reproduction, 19(12):2869-2874.
Medina & Lebovic, 2009, Endometriosis-associated nerve fibers and pain, Acta Obstet Gynecol Scand 88:968-75.
Messina, 2011, Dysregulation of Semaphorin7A/β1-integrin signaling leads to defective GnRH-1 cell migration, abnormal gonadal development and altered fertility, Hum Mol Genetics 20(24):4759-74.
Miettinen, 2001, Abnormal lipoprotein metabolism and reversible female infertility in HDL receptor (SR-BI)—deficient mice, J Clin Invest 108:1717-22.
Moore, 2005, "Molecular biology and physiological role of the oocyte factor, BMP-15," Mol Cell Endocrinol 234(1-2):67-73.
Mottershead, 2008, "Characterization of recombinant human growth differentiation factor-9 signaling in ovarian granulosa cells," Mol Cell Endocrinol 283(1-2):58-67.
Moudrianakis & Beer, 1965, Base sequence determination in nucleic acids with the electron microscope, PNAS 53:564-71.
Mouillet, 2008, "DEAD-box protein-103 (DP103, Ddx20) is essential for early embryonic development and modulates ovarian morphology and function," Endocrinology 149(5):2168-75.
Murray, 1999, Microdeletions in FMR2 may be a significant cause of premature ovarian failure, Journal of Medical Genetics 36:767-70.
Nicotra, 1998, Adenosine deaminase and human reproduction: a comparative study of fertile women and women with recurrent spontaneous abortion, Am. J. Reprod. Immunol. 39:266-70.
Aston et al. Human Reproduction. 2010. 25(6)L 1383-1397.
Bale et al. Nature Biotechnology. Feb. 2011. 29: 117-118.
Elashoff et al., "Accurate prediction of the number of cycles to achieve live birth," Fertility and Sterility, vol. 100, No. 3, Oct. 2013.
Gagneux et al. Molecular Phylogenetics and Evolution. 2001. 18:2-13.
Halushka et al. Nature. Jul. 1999. 22: 239-247.
Hattersley et al. The Lancet. 2005. 366: 1315-1323.
Hirschhorn et al. Genetics in Medicine. vol. 4, No. 2, pp. 45-61, Mar. 2002.
Lucentini et al The Scientist (2004) vol. 18, p. 2.
Minaretzis et al., "Multivariate Analysis of Factors Predictive of Successful Live Births in In Vitro Fertilization (IVF) Suggests Strategies to Improve IVF Outcome," Journal of Assisted Reproduction and Genetics, vol. 15, No. 6, Jan. 1998, pp. 365-371.
Mummidi et al Journal of Biological Chemistry 2000 vol. 275 No. 25 pp. 18946-18961.
Shelling et al. Reproduction. 2010. 140: 633-641.
Stolk et al. Nature Genetics. Available online Jan. 22, 2012.44(3): 260.
Yue et al. BMC Bioinformatics. 2006. 7:166.
Zhang et al Nucleic Acids Research. Published online May 27, 2011. 39: W437-W443.

Combining Clinical and Genetic Data Analytics

Fertility doctors collect clinical data for SART reporting.

Celmatix cleans and analyzes clinical data: 100,000 cycles 200 variables we are able to narrow in more rapidly on genetic biomarkers.

With a cleaner cohort of patients..

The application of data analytics allows us to identify outliers more effectively.

METHODS AND DEVICES FOR ASSESSING RISK OF FEMALE INFERTILITY

RELATED APPLICATIONS

This application is a continuation-in-part of U.S. Non-Provisional Ser. No. 14/107,800, filed Dec. 16, 2013, which claims priority to U.S. Provisional Nos. 61/889,738, filed Oct. 11, 2013, and 61/737,693, filed Dec. 14, 2012. This application also claims priority to and the benefit of U.S. Provisional No. 61/932,226, filed Jan. 27, 2014. The aforementioned applications are incorporated by reference herein.

TECHNICAL FIELD

The invention generally relates to methods and devices for assessing risk of female infertility.

BACKGROUND

Approximately one in seven couples has difficulty conceiving. Infertility may be due to a single cause in either partner, or a combination of factors (e.g., genetic factors, diseases, or environmental factors) that may prevent a pregnancy from occurring or continuing. Every woman will become infertile in her lifetime due to menopause. On average, egg quality and number begins to decline precipitously at 35. However, some women experience this decline much earlier in life, while a number of women are fertile well into their 40's. Though, generally, advanced maternal age (35 and above) is associated with poorer fertility outcomes, there is no way of diagnosing egg quality issues in younger women or knowing when a particular woman will start to experience decline in her egg quality or reserve.

The elucidation of the genetic basis of female infertility disorders permits the development of powerful, rapid, and non-invasive diagnostic tools that will help clinicians direct patients to efficient and effective treatment options. Additionally, the discovery of the key genes underlying these disorders holds great promise for the identification of novel targets for drug development and therapeutics. Finally, a better understanding of the crucial molecular pathways underlying human fertility guides the next generation of targeted, non-hormonal contraceptives.

SUMMARY

The invention provides applications and methods for determining the identity of genetic loci biologically or statistically correlated with increased risk of susceptibility of an individual to infertility or early-onset decrease in fertility (premature menopause). In one aspect, the invention provides nucleic acid sequences that can be used to assess the presence or absence of particular nucleotides at polymorphic sites in an individual's RNA or genomic DNA that are associated with susceptibility to decreased fertility. In certain aspects, the invention provides methods for observing commonly occurring or rare genetic variants within a subset of genes of interest for human infertility and risk of premature menopause. In certain aspects, the invention provides methods for ranking the relative importance of individual genetic variants, genes, or genetic regions for allowing determination of infertility or premature menopause risk. In certain aspects, the invention provides a method for identifying a human subject as having an increased risk for infertility or premature menopause, including the following steps: 1) obtaining a sample from a patient; 2) conducting an assay on at least one infertility-associated biomarker; and 3) assessing risk to the patient of developing early-onset decrease in fertility.

As discussed below, an array of genetic information concerning the status of various infertility-related genetic regions is used in order to assess the risk of a subject having an increased susceptibility to reduced fertility, premature menopause, or infertility. The genetic information may include one or more polymorphisms in one or more infertility-related genetic regions, mutations in one or more of those genetic regions, or particular epigenetic signatures affecting the expression of those genetic regions. The molecular consequence of these genetic region mutations could be one or a combination of the following: alternative splicing, lowered or increased RNA expression, and/or alterations in protein expression. These alterations could also include a different protein product being produced, such as one with reduced or increased activity, or a protein that elicits an abnormal immunological reaction. All of this information is significant in terms of informing a patient of her susceptibility to infertility or reduced fertility relative to her age or other relevant phenotypes such as hormone levels or ovarian follicle count.

In addition to looking exclusively at genomic information, by combining genetic information (e.g., polymorphisms, mutations, etc.) with phenotypic and/or environmental data, methods of the invention provide an additional level of clinical clarity. For example, polymorphisms in genes discussed below may provide information about a disposition toward infertility or reduced fertility. However, in certain cases, the clinical outcome may not be determinative unless combined with certain phenotypic and/or environmental information. Thus, methods of the invention provide for a combination of genetic predispositional analyses in combination with phenotypic and environmental exposure data in order to assess the potential for infertility or reduced fertility relative to age. Thus, in certain cases, genetic predisposition may be sufficient to make a diagnosis, but in other cases, the clinical outcome may not be clear based upon genetic analysis alone and the combination of genetic and phenotypic or environmental data must be used in order to assess the likelihood of infertility or reduced fertility.

In addition to providing information to women related to the risk of infertility or reduced fertility if she chooses to try for a child at a particular age, methods of the invention may also be used by a physician for treatment purposes, e.g., allowing a physician to make vitamin/drug recommendations to help reduce or eliminate the risk to early-onset reduction in fertility. For example, data herein show that a mutation in the CBS gene affects infertility. This data may be used by a physician to generate a treatment plan that may help remediate the infertility risk in the woman. For example, the physician may advise the woman to take a high dose of folic acid or other vitamin supplements/drugs in order to improve fertility. Such a treatment plan may reduce or eliminate the infertility risk in the woman.

A biomarker generally refers to a molecule that acts as an indicator of a biological state. In certain embodiments, the biomarker is a genetic region. In particular embodiments, the genetic region is an infertility-related genetic region. Any assay known in the art may be used to analyze the genetic region. In certain embodiments, the assay includes sequencing at least a portion of the genetic region to determine presence or absence of a mutation that is associated with infertility. Mutations detected according to the invention may be any type of genetic mutation. Exemplary mutations include a single nucleotide polymorphism, a deletion, an insertion, an inversion, other rearrangements, a copy number variation, or a combination thereof. Any method of detecting genetic mutations is useful with methods of the invention, and numerous methods are known in the art. In certain embodiments, sequencing is used to determine the presence of a mutation in the infertility-associated genetic region. In particularly-preferred embodiments, the sequencing is sequencing-by-synthesis.

In other embodiments, the biomarker is a gene product. In particular embodiments, the gene product is a product of an infertility-related gene. The gene product may be RNA or protein. Any assay known in the art may be used to analyze the gene product. In certain embodiments, the assay involves determining an amount of the gene product and comparing the determined amount to a reference.

Methods of the invention may further involve obtaining a sample from the mammal that includes the infertility-associated biomarker. The sample may be a human tissue or body fluid. In particular embodiments, the sample is blood or saliva. Methods of the invention may also involve enriching the sample for the infertility-associated biomarker.

Methods of the invention may be used to assess the risk of infertility that is linked to an infertility-associated biomarker. Another aspect of the invention provides methods for assessing infertility that involve obtaining a sample, conducting an assay on at least one infertility-associated biomarker, and assessing level of fertility based on results of the assay.

DETAILED DESCRIPTION

Figure 1:
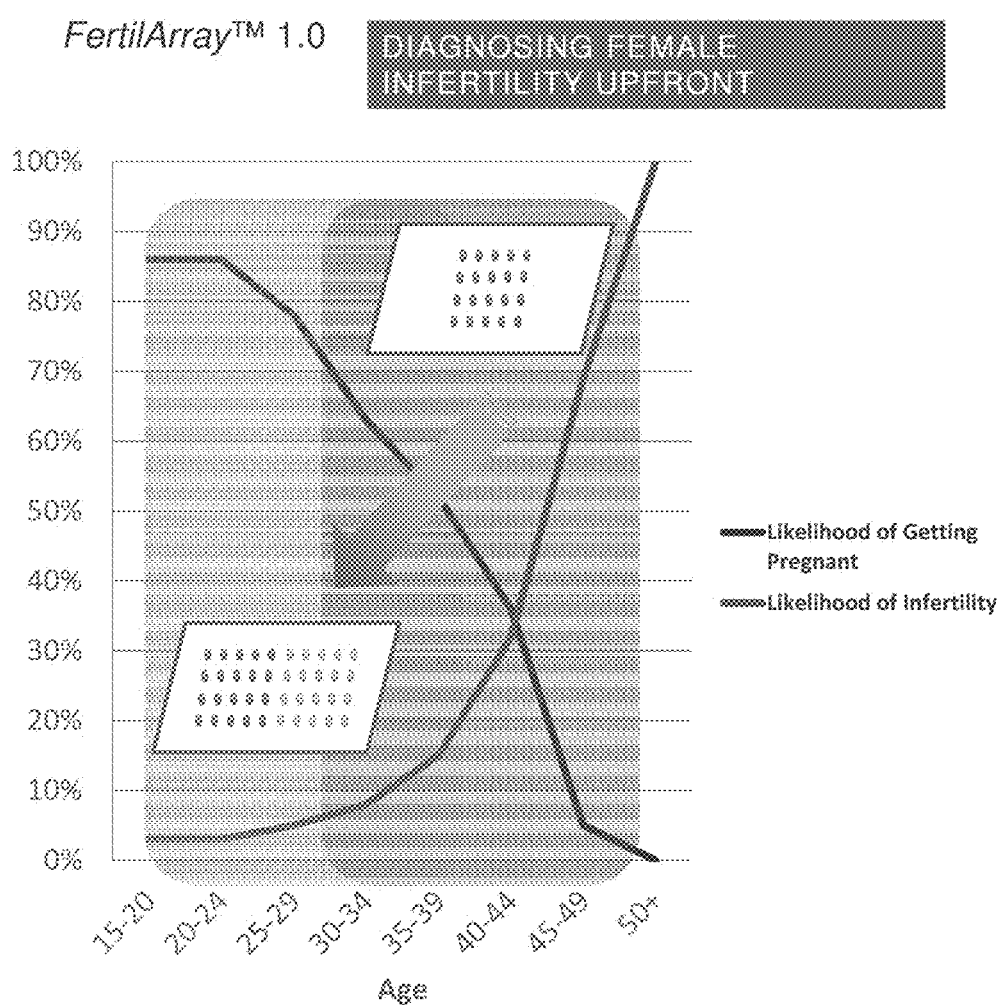
FIG. 1 depicts the rate of decline of fertility with age and the corresponding increase in the risk of infertility with age. The shades areas represent different age groups who would benefit from a genetic screen for infertility risk (late teen to mid 40's) versus a genetic screen of premature decline in fertility (late teens to late 30's).
Figure 2:
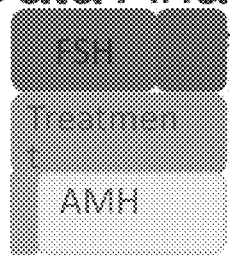
FIG. 2 depicts one way that phenotypic variables can be utilized to accelerate the discovery of genetic regions related to female infertility.
Figure 2:
Figure 2:
Figure 2:
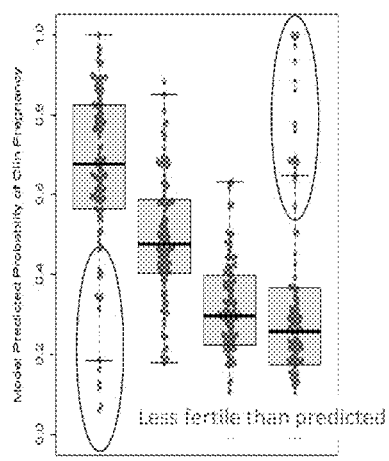
Figure 2:
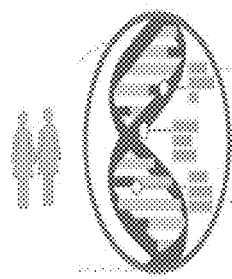
Figure 2:
Figure 2:
Figure 3:
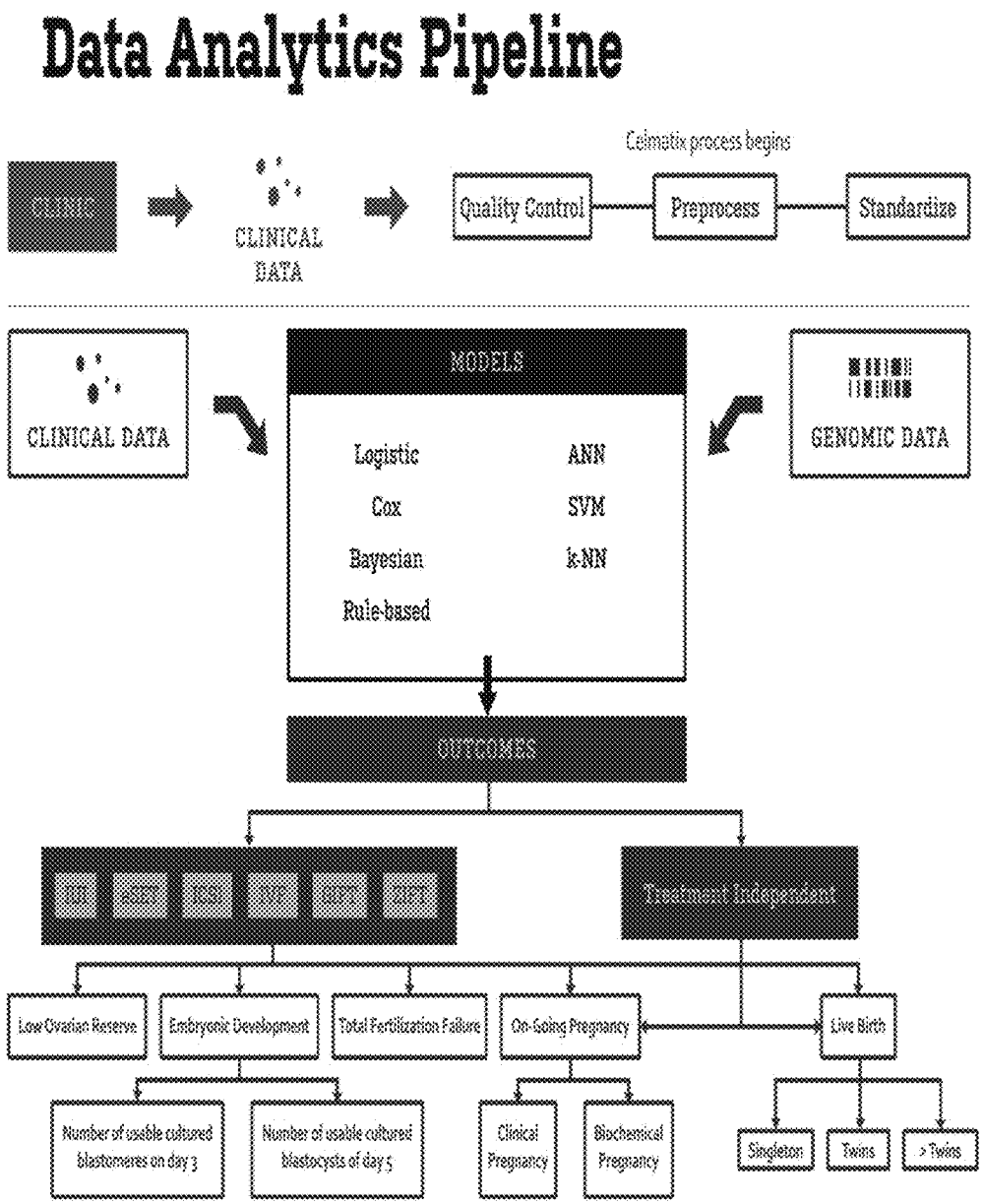
FIG. 3 depicts the methodology for integrating clinical data with genomic data to predict treatment dependent and independent fertility outcomes.
Figure 4:
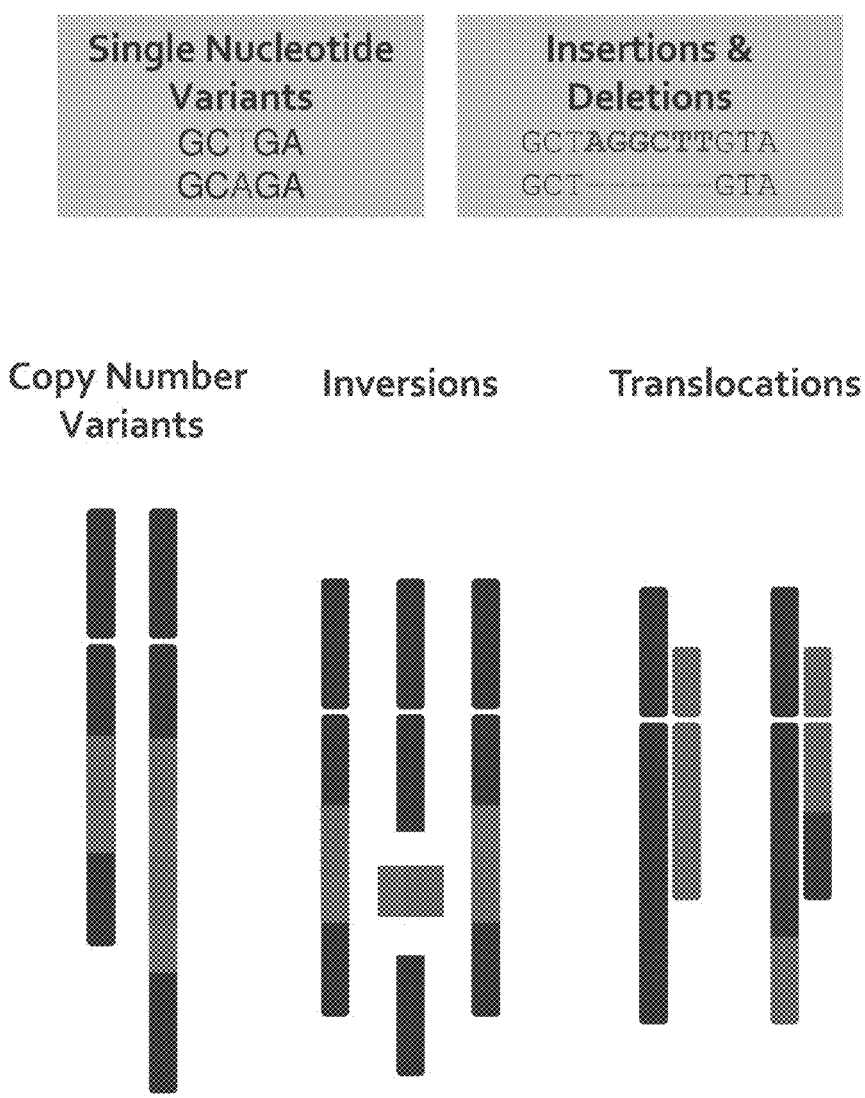
FIG. 4 depicts the different kinds of genetic variants associated with risk of infertility.

The invention generally relates to methods and devices for assessing risk of susceptibility to infertility, reduced fertility, or reduced fertility at a particular age including premature menopause. In certain embodiments, the invention provides methods for assessing risk of susceptibility to infertility or reduced fertility that involve obtaining a biological sample, conducting an assay on at least one infertility-associated biomarker, and assessing risk to of infertility or reduced fertility based upon results of the assay.

Samples

Methods of the invention involve obtaining a sample, e.g., a tissue or body fluid, that is suspected to include an infertility-associated gene or gene product. The sample may be collected in any clinically acceptable manner. A tissue is a mass of connected cells and/or extracellular matrix material, e.g. skin tissue, hair, nails, endometrial tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, maternal blood, phlegm, saliva, sweat, amniotic fluid, menstrual fluid, endometrial aspirates, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed. In certain embodiments, infertility-associated genes or gene products may be found in reproductive cells or tissues, such as gametic cells, gonadal tissue, fertilized embryos, and placenta. In certain embodiments, the sample is drawn blood or saliva.

Nucleic acid is extracted from the sample according to methods known in the art. See for example, Maniatis, et al., Molecular Cloning: A Laboratory Manual, Cold Spring Harbor, N.Y., pp. 280-281, 1982, the contents of which are incorporated by reference herein in their entirety. In certain embodiments, a genomic sample is collected from a subject followed by enrichment for genetic regions or genetic fragments of interest, for example by hybridization to a nucleotide array comprising fertility-related genes or gene fragments of interest. The sample may be enriched for genes of interest (e.g., infertility-associated genes) using methods known in the art, such as hybrid capture. See for examples, Lapidus (U.S. Pat. No. 7,666,593), the content of which is incorporated by reference herein in its entirety.

RNA may be isolated from eukaryotic cells by procedures that involve lysis of the cells and denaturation of the proteins contained therein. Tissue of interest includes gametic cells, gonadal tissue, endometrial tissue, fertilized embryos, and placenta. RNA may be isolated from fluids of interest by procedures that involve denaturation of the proteins contained therein. Fluids of interest include blood, menstrual fluid, mammary fluid, follicular fluid of the ovary, peritoneal fluid, or culture medium. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+ RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX (see Ausubel et al., CURRENT PROTOCOLS IN MOLECULAR BIOLOGY, vol. 2, Current Protocols Publishing, New York (1994). Once bound, poly(A)+ mRNA is eluted from the affinity column using 2 mM EDTA/0.1% SDS.

Biomarkers

A biomarker generally refers to a molecule that may act as an indicator of a biological state. Biomarkers for use with methods of the invention may be any marker that is associated with infertility. Exemplary biomarkers include genes (e.g. any region of DNA encoding a functional product), genetic regions (e.g. regions including genes and intergenic regions with a particular focus on regions conserved throughout evolution in placental mammals), and gene products (e.g., RNA and protein). In certain embodiments, the biomarker is an infertility-associated genetic region. An infertility-associated genetic region is any DNA sequence in which variation is associated with a change in fertility. Examples of changes in fertility include, but are not limited to, the following: a homozygous mutation of an infertility-associated gene leads to a complete loss of fertility; a homozygous mutation of an infertility-associated gene is incompletely penetrant and leads to reduction in fertility that varies from individual to individual; a heterozygous mutation is completely recessive, having no effect on fertility; and the infertility-associated gene is X-linked, such that a potential defect in fertility depends on whether a non-functional allele of the gene is located on an inactive X chromosome (Barr body) or on an expressed X chromosome.

According to certain aspects, methods of the invention provide for determining infertility genetic regions of interest based on data obtained from public and private fertility/infertility related databases. Infertility/fertility related data may include implantation genes, idiopathic infertility genes, polycystic ovary syndrome (PCOS) genes, egg quality genes, endometriosis genes, and premature ovarian failure genes. As described below, the infertility/fertility related data can then be processed using evolutionary conservation to identify genomic regions and variations of interest.

Evolutionary conservation analysis involves, generally, comparing nucleic acid sequences among evolutionary and distantly related genomes to identify similarities and differences between coding and/or non-coding regions across the genomes. The similarity between a region being examined and the related genomes correlates to a degree of conservation. Regions (e.g. coding, non-coding regions, and intergenic regions flanking a gene) that maintain a high degree of similarity across genomes over time are considered highly conserved. Differences between the examined region and regions of related genomes indicate that the examined region has evolved over time. If the examined region is conserved among related genomes, the region is generally considered to exhibit or perform functions that are important for the species (i.e. functionally relevant). This is because genetic abnormalities at functionally important regions are typically harmful to the species, and are phased out over the evolutionary time span. Because functional elements are subject to selection, functional regions tend to evolve at slower rates than nonfunctional regions. A degree of conservation (e.g. degree of similarity between a target genomic region and related genomes) that is considered to be functionally relevant depends on the particular application. For example, a functionally relevant degree of conservation may be 80%, 85%, 90%, 91%, 92%, 93%, 94%, 95%, 96% 97%, 98%, 99%, etc. Regions of genes identified by evolutionary conservation as being functionally-relevant can then be used as regions of interest for diagnosing diseases and disorders, such as infertility.

According to certain embodiments, infertility regions of interest are identified by performing evolutionary conservation analysis of one or more genes obtained from infertility and/or fertility-related data. The process of filtering through infertility/fertility related databases using evolutionary conservation, according to the invention, is called the ABCoRE algorithm (see FIG. 6). For example, nucleic acid data obtained from the infertility/fertility related databases can be compared to distantly related genomes in order to assess conservation of the infertility-related nucleic acid. Regions of the nucleic acid determined to be conserved are classified as infertility regions of interest. In one embodiment, methods of the invention assess conservation of coding regions to determine infertility regions of interest. In another embodiment, methods of the invention assess conservation of non-coding regions to determine infertility regions of interest. In further embodiments, methods of the invention assess conservation of intergenic regions (i.e. a non-coding region flanking a gene) to determine infertility regions of interest. In other embodiments, conversation of both coding and non-coding regions is assessed to determine infertility regions of interest. In any of the above embodiments, coding, non-coding, and intergenic regions may be classified as an infertility region of interest if they have a degree of conservation of, for example, 80%, 85%, 90%, 91%, 92%, 93%, 94%, 95%, 96% 97%, 98%, 99%, etc.

In particular aspects, the following method is employed to determine whether a genomic region is a fertility region of interest using conservation analysis. First, private and/or public nucleic acid data corresponding to infertility or fertility is obtained. Next, one or more genetic loci from that data is examined for conservation. The coding regions (i.e. exons)) of a gene, non-coding regions of the gene, and/or regions flanking the gene (intergenic regions upstream and downstream from the gene being examined) are then analyzed for conservation. According to certain embodiments, if the coding region is found to be conserved (e.g. a degree of conservation 90% or above), the coding region is considered to be an infertility region of interest. The degree of conservation of the non-coding region is then compared to the degree of conservation of the coding region. If the degree of conservation of the non-coding region is similar to the degree of conversation of the coding region, then the non-coding region is also classified an infertility region of interest. This degree of conservation comparison may also be used to determine whether intergenic regions flanking a gene should be classified as an infertility region of interest.

Conservation of coding and/or non-coding sequences is described in Hardison, R. C., Oeltjen, J., and Miller, W. 1997. Long human-mouse sequence alignments reveal novel regulatory elements: A reason to sequence the mouse genome. Genome Res. 7: 959-966; Brenner, S., Venkatesh, B., Yap, W. H., Chou, C. F., Tay, A., Ponniah, S., Wang, Y., and Tan, Y. H. 2002. Conserved regulation of the lymphocyte-specific expression of lck in the Fugu and mammals. Proc. Natl. Acad. Sci. 99: 2936-2941; Karolchik, Donna, et al. "Comparative genomic analysis using the UCSC genome browser." Comparative Genomics. Humana Press, 2008. 17-33; Santini, Simona, Jeffrey L. Boore, and Axel Meyer. "Evolutionary conservation of regulatory elements in vertebrate Hox gene clusters." Genome research 13.6a (2003): 1111-1122; Roth, F. P., Hughes, J. D., Estep, P. W., and Church, G. M. 1998. Finding DNA regulatory motifs within unaligned noncoding sequences clustered by whole-genome mRNA quantitation. Nat. Biotechnol. 16: 939-945; and Blanchette, M. and Tompa, M. 2002. Discovery of regulatory elements by a computational method for phylogenetic footprinting. Genome Res. 12: 739-748.

In particular embodiments, the infertility-associated genetic region is a maternal effect gene. Maternal effects genes are genes that have been found to encode key structures and functions in mammalian oocytes (Yurttas et al., Reproduction 139:809-823, 2010). Maternal effect genes are described, for example in, Christians et al. (Mol Cell Biol 17:778-88, 1997); Christians et al., Nature 407:693-694, 2000); Xiao et al. (EMBO J. 18:5943-5952, 1999); Tong et al. (Endocrinology 145:1427-1434, 2004); Tong et al. (Nat Genet. 26:267-268, 2000); Tong et al. (Endocrinology, 140: 3720-3726, 1999); Tong et al. (Hum Reprod 17:903-911, 2002); Ohsugi et al. (Development 135:259-269, 2008); Borowczyk et al. (Proc Natl Acad Sci USA, 2009); and Wu (Hum Reprod 24:415-424, 2009). The content of each of these is incorporated by reference herein in its entirety.

The above-described infertility genetic regions of interest may then be ranked according to significance using one or more the following ranking schemes of the invention.

In particular embodiments, the infertility-associated genetic region is a gene (including exons, introns, and evolutionarily conserved regions of DNA flanking either side of said gene) that impacts fertility selected from the genes shown in Table 1 below. In Table 1, HGNC (http://www.genenames.org/) reference numbers are provided when available.

Table 1 below depicts one possible gene ranking scheme for the relative infertility, subfertility, or premature decline in fertility risk associated with novel or common mutations or variants in a fertility gene. The number of varients column corresponds to the experimental observations of these variants in a study of women with unexplained infertility. The most highly ranked (from top to bottom) genes in this list contained the most varients that were predicted to significantly affect protein structure and function (biologically significant) out of a list of fertility related genes. Genetic variants considered to be biologically significant include mutations that result in a change: 1) to a different amino acid predicted to alter the folding and/or structure of the encoded protein, 2) to a different amino acid occurring at a site with high evolutionarily conservation in mammals, 3) that introduces a premature stop termination signal, 4) that causes a stop termination signal to be lost, 5) that introduces a new start codon, 6) that causes a start codon to be lost, 7) that disrupts a splicing signal, 8) that alters the reading frame or 9) that alters the dosage of encoded protein or RNA. All genetic variants detected from re-sequencing exclude sites where the variant allele is detected in only one chromosome (singletons) and sites sequenced in only one individual.

TABLE 1

Genomic loci containing biologically significant mutations ranked based on number of biologically significant variants observed in a study of unexplained female infertility.

| Gene | Celmatix Gene ID | Entrez ID | HGNC ID | Number of Variants detected | Variant Description (type and count) |
|---|---|---|---|---|---|
| MUC4 | CMX-G0000006719 | 4585 | 7514 | 353 | Drastic nonsynonymous: 352; Start codon gained: 1 |
| EPHA8 | CMX-G0000000415 | 2046 | 3391 | 23 | CNV loss: 23 |
| LOXL4 | CMX-G0000016263 | 84171 | 17171 | 11 | CNV loss: 11 |
| FGF8 | CMX-G0000016316 | 2253 | 3686 | 4 | CNV gain: 4 |
| KISS1R | CMX-G0000026560 | 84634 | 4510 | 4 | CNV gain: 4 |
| SCARB1 | CMX-G0000019991 | 949 | 1664 | 4 | Drastic nonsynymous: 1; Start codon gained: 3 |
| BARD1 | CMX-G0000004834 | 580 | 952 | 3 | Drastic nonsynymous: 1; Start codon gained: 1 Start codon lost: 1 |
| DDX20 | CMX-G0000001412 | 11218 | 2743 | 3 | Start codon gained: 3 |
| ECHS1 | CMX-G0000016594 | 1892 | 3151 | 3 | CNV gain: 2, CNV loss: 1 |
| FMN2 | CMX-G0000002910 | 56776 | 14074 | 3 | Start codon gained: 3 |
| FOXO3 | CMX-G0000010672 | 2309 | 3821 | 3 | CNV gain: 3 |
| HS6ST1 | CMX-G0000004221 | 9394 | 5201 | 3 | Drastic nonsynymous: 3 |
| MAP3K2 | CMX-G0000004205 | 10746 | 6854 | 3 | CNV gain: 3 |
| MST1 | CMX-G0000005619 | 4485 | 7380 | 3 | Drastic nonsynymous: 2 Splice site acceptor: 1 |
| MTRR | CMX-G0000008130 | 4552 | 7473 | 3 | Drastic nonsynymous: 3 |

TABLE 1-continued

Genomic loci containing biologically significant mutations ranked based on number of biologically significant variants observed in a study of unexplained female infertility.

| Gene | Celmatix Gene ID | Entrez ID | HGNC ID | Number of Variants detected | Variant Description (type and count) |
|---|---|---|---|---|---|
| NLRP11 | CMX-G0000028188 | 204801 | 22945 | 3 | Drastic nonsynonymous: 2; Start codon gained: 1 |
| NLRP14 | CMX-G0000016919 | 338323 | 22939 | 3 | Drastic nonsynonymous: 3 |
| NLRP8 | CMX-G0000028191 | 126205 | 22940 | 3 | Drastic nonsynonymous: 2; Stop codon lost: 1 |
| ASCL2 | CMX-G0000016707 | 430 | 739 | 2 | Start codon gained: 1 CNV gain: 1 |
| BMP6 | CMX-G0000009564 | 654 | 1073 | 2 | CNV loss: 2 |
| BRCA1 | CMX-G0000025305 | 672 | 1100 | 2 | Drastic nonsynonymous: 2 |
| BRCA2 | CMX-G0000020222 | 675 | 1101 | 2 | Drastic nonsynonymous: 2 |
| CENPI | CMX-G0000031175 | 2491 | 3968 | 2 | Start codon gained: 2 |
| COMT | CMX-G0000029621 | 1312 | 2228 | 2 | Drastic nonsynonymous: 1; Start codon gained: 1 |
| CYP11B1 | CMX-G0000013888 | 1584 | 2591 | 2 | CNV gain: 2 |
| DAZL | CMX-G0000005296 | 1618 | 2685 | 2 | Start codon gained: 2 |
| EEF1A1 | CMX-G0000010487 | 1915 | 3189 | 2 | Start codon gained: 2 |
| FMR1 | CMX-G0000031614 | 2332 | 3775 | 2 | Drastic nonsynonymous: 1; Start codon gained: 1 |
| GDF1 | CMX-G0000027183 | 2657 | 4214 | 2 | Drastic nonsynonymous: 1; CNV gain: 1 |
| HK3 | CMX-G0000009361 | 3101 | 4925 | 2 | Drastic nonsynonymous: 2 |
| IGF2 | CMX-G0000016702 | 3481 | 5466 | 2 | CNV gain: 2 |
| ISG15 | CMX-G0000000029 | 9636 | 4053 | 2 | CNV gain: 2 |
| JMY | CMX-G0000008593 | 133746 | 28916 | 2 | Drastic nonsynonymous: 2 |
| KL | CMX-G0000020228 | 9365 | 6344 | 2 | Drastic nonsynonymous: 2 |
| MTHFR | CMX-G0000000213 | 4524 | 7436 | 2 | Drastic nonsynonymous: 1; Start codon gained: 1 |
| NLRP13 | CMX-G0000028190 | 126204 | 22937 | 2 | Drastic nonsynonymous: 2 |
| NLRP5 | CMX-G0000028192 | 126206 | 21269 | 2 | Drastic nonsynonymous: 2 |
| NOBOX | CMX-G0000012690 | 135935 | 22448 | 2 | Drastic nonsynonymous: 2 |
| PRKRA | CMX-G0000004587 | 8575 | 9438 | 2 | Drastic nonsynonymous: 1; Nonsynonymous start: 1 |
| SDC3 | CMX-G0000000574 | 9672 | 10660 | 2 | Drastic nonsynonymous: 2 |
| TACC3 | CMX-G0000006818 | 10460 | 11524 | 2 | Drastic nonsynonymous: 2 |
| TLE6 | CMX-G0000026639 | 79816 | 30788 | 2 | CNV loss: 2 |
| ACVR1C | CMX-G0000004406 | 130399 | 18123 | 1 | Drastic nonsynonymous: 1 |
| AHR | CMX-G0000011332 | 196 | 348 | 1 | Start codon gained: 1 |
| APOA1 | CMX-G0000018327 | 335 | 600 | 1 | CNV gain: 1 |
| AURKA | CMX-G0000028967 | 6790 | 11393 | 1 | Start codon gained: 1 |
| BMP15 | CMX-G0000030783 | 9210 | 1068 | 1 | CNV gain: 1 |
| BMP4 | CMX-G0000021216 | 652 | 1071 | 1 | Stop codon lost: 1 |
| C6orf221 | CMX-G0000010478 | 154288 | 33699 | 1 | Drastic nonsynonymous: 1 |
| CASP8 | CMX-G0000004721 | 841 | 1509 | 1 | CNV loss: 1 |
| CBS | CMX-G0000029408 | 875 | 1550 | 1 | Drastic nonsynonymous: 1 |
| CDX2 | CMX-G0000020191 | 1045 | 1806 | 1 | Drastic nonsynonymous: 1 |
| CENPF | CMX-G0000002670 | 1063 | 1857 | 1 | Drastic nonsynonymous: 1 |
| CGB | CMX-G0000027860 | 1082 | 1886 | 1 | Start codon gained: 1 |
| CSF1 | CMX-G0000001374 | 1435 | 2432 | 1 | CNV loss: 1 |
| CSF2 | CMX-G0000008885 | 1437 | 2434 | 1 | CNV loss: 1 |
| DCTPP1 | CMX-G0000023705 | 79077 | 28777 | 1 | CNV gain: 1 |
| DNMT1 | CMX-G0000026880 | 1786 | 2976 | 1 | Drastic nonsynonymous: 1 |
| EFNA4 | CMX-G0000001896 | 1945 | 3224 | 1 | CNV loss: 1 |
| EFNB3 | CMX-G0000024616 | 1949 | 3228 | 1 | CNV gain: 1 |
| EIF3CL | CMX-G0000023621 | 728689 | 26347 | 1 | CNV loss: 1 |

TABLE 1-continued

Genomic loci containing biologically significant mutations ranked based on number of biologically significant variants observed in a study of unexplained female infertility.

| Gene | Celmatix Gene ID | Entrez ID | HGNC ID | Number of Variants detected | Variant Description (type and count) |
|---|---|---|---|---|---|
| EPHA5 | CMX-G0000007213 | 2044 | 3389 | 1 | CNV loss: 1 |
| EPHA7 | CMX-G0000010603 | 2045 | 3390 | 1 | CNV loss: 1 |
| EZH2 | CMX-G0000012702 | 2146 | 3527 | 1 | Drastic nonsynonymous: 1 |
| FOXL2 | CMX-G0000006297 | 668 | 1092 | 1 | Start codon gained: 1 |
| FOXP3 | CMX-G0000030750 | 50943 | 6106 | 1 | CNV gain: 1 |
| GALT | CMX-G0000014248 | 2592 | 4135 | 1 | Splice site acceptor: 1 |
| GDF9 | CMX-G0000008902 | 2661 | 4224 | 1 | Start codon gained: 1 |
| GJA4 | CMX-G0000000643 | 2701 | 4278 | 1 | CNV gain: 1 |
| GJB3 | CMX-G0000000642 | 2707 | 4285 | 1 | CNV gain: 1 |
| GJB4 | CMX-G0000000641 | 127534 | 4286 | 1 | CNV gain: 1 |
| GJD3 | CMX-G0000025169 | 125111 | 19147 | 1 | CNV gain: 1 |
| GPC3 | CMX-G0000031486 | 2719 | 4451 | 1 | CNV gain: 1 |
| HSD17B2 | CMX-G0000024260 | 3294 | 5211 | 1 | Drastic nonsynonymous: 1 |
| IGFBPL1 | CMX-G0000014341 | 347252 | 20081 | 1 | CNV loss: 1 |
| KISS1 | CMX-G0000002533 | 3814 | 6341 | 1 | CNV gain: 1 |
| LHCGR | CMX-G0000003462 | 3973 | 6585 | 1 | Drastic nonsynonymous: 1 |
| MAD1L1 | CMX-G0000011200 | 8379 | 6762 | 1 | Start codon gained: 1 |
| MAD2L1 | CMX-G0000007650 | 4085 | 6763 | 1 | Start codon gained: 1 |
| MB21D1 | CMX-G0000010484 | 115004 | 21367 | 1 | Drastic nonsynonymous: 1 |
| MCM8 | CMX-G0000028433 | 84515 | 16147 | 1 | Drastic nonsynonymous: 1 |
| MYC | CMX-G0000013826 | 4609 | 7553 | 1 | Start codon gained: 1 |
| NLRP2 | CMX-G0000028140 | 55655 | 22948 | 1 | Start codon gained: 1 |
| NLRP4 | CMX-G0000028189 | 147945 | 22943 | 1 | Start codon gained: 1 |
| OAS1 | CMX-G0000019838 | 4938 | 8086 | 1 | Splice site acceptor: 1 |
| PADI3 | CMX-G0000000342 | 51702 | 18337 | 1 | CNV gain: 1 |
| PAEP | CMX-G0000015254 | 5047 | 8573 | 1 | CNV gain: 1 |
| PLCB1 | CMX-G0000028445 | 23236 | 15917 | 1 | CNV gain: 1 |
| PMS2 | CMX-G0000011251 | 5395 | 9122 | 1 | Drastic nonsynonymous: 1 |
| POF1B | CMX-G0000031099 | 79983 | 13711 | 1 | CNV gain: 1 |
| PRDM9 | CMX-G0000008219 | 56979 | 13994 | 1 | CNV loss: 1 |
| SEPHS2 | CMX-G0000023707 | 22928 | 19686 | 1 | CNV gain: 1 |
| SERPINA10 | CMX-G0000021629 | 51156 | 15996 | 1 | CNV gain: 1 |
| SIRT3 | CMX-G0000016629 | 23410 | 14931 | 1 | CNV loss: 1 |
| SPN | CMX-G0000023664 | 101929889 | 11249 | 1 | CNV loss: 1 |
| TFPI | CMX-G0000004632 | 7035 | 11760 | 1 | Drastic nonsynonymous: 1 |
| TGFB1I1 | CMX-G0000023757 | 7041 | 11767 | 1 | CNV gain: 1 |
| TP63 | CMX-G0000006674 | 8626 | 15979 | 1 | Start codon gained: 1 |
| UBE3A | CMX-G0000022200 | 7337 | 12496 | 1 | Start codon gained: 1 |
| UBL4B | CMX-G0000001378 | 164153 | 32309 | 1 | CNV loss: 1 |
| UIMC1 | CMX-G0000009362 | 51720 | 30298 | 1 | Drastic nonsynonymous: 1 |
| VKORC1 | CMX-G0000023741 | 79001 | 23663 | 1 | CNV gain: 1 |
| ZP3 | CMX-G0000011947 | 7784 | 13189 | 1 | Start codon gained: 1 |

In particular embodiments, the infertility-associated genetic region is a gene (including exons, introns, and evolutionarily conserved regions of DNA flanking either side of said gene) that impacts fertility selected from the genes shown in Table 2 below. In Table 2, HGNC (http://www.genenames.org/) reference numbers are provided when available.

Table 2 below depicts another possible gene ranking scheme for the relative infertility, subfertility, or premature decline in fertility risk associated with novel or common mutations or variants in a fertility gene. Table 2 contains the 10 genes, listed in order from most to least statistically significant, that were determined to be statistically significantly correlated with infertility risk in a study of unexplained female infertilty based on variants detected in the coding regions of these genes. P-values<0.025 are considered statistically significant, and all other fertility genes did not fit the pass the significance test for inclusion and ranking in this list. For the coding level analysis, we first compute a coding variant score for the coding regions for each individual/gene. The coding variant score represents the variability of the gene at coding regions in an individual and is computed as the sum of the proportion of variant locations within the coding regions of that gene for that individual. A series of linear regression models are fit, where the outcome variable is the coding variant score for a given gene, and the independent variables are group (infertile vs control) and principal component derived ethnicity (continuous). The p-value for group is used for statistical inference. The model is fit once for each gene.

TABLE 2

Fertility genes demonstrating statistical significance at the gene coding region level for infertility risk ranked based on p-values, observed in a study of unexplained female infertility.

| Gene | Celmatix Gene ID | Entrez ID | HGNC ID | P-value |
|---|---|---|---|---|
| ZP4 | CMX-G0000002903 | 57829 | 15770 | 5.17E−10 |
| UIMC1 | CMX-G0000009362 | 51720 | 30298 | 0.001401803 |
| PADI6 | CMX-G0000000344 | 353238 | 20449 | 0.003420271 |
| ZP1 | CMX-G0000017558 | 22917 | 13187 | 0.003845858 |
| MDM2 | CMX-G0000019503 | 4193 | 6973 | 0.009323844 |
| PRKRA | CMX-G0000004587 | 8575 | 9438 | 0.009832035 |
| PMS2 | CMX-G0000011251 | 5395 | 9122 | 0.015453858 |
| TGFB1 | CMX-G0000027588 | 7040 | 11766 | 0.018576967 |
| ESR2 | CMX-G0000021326 | 2100 | 3468 | 0.022661688 |
| PRDM1 | CMX-G0000010653 | 639 | 9346 | 0.024522163 |

In particular embodiments, the infertility-associated genetic region is a gene (including exons, introns, and evolutionarily conserved regions of DNA flanking either side of said gene) that impacts fertility selected from the genes shown in Table 3 below. In Table 3, HGNC (http://www.genenames.org/) reference numbers are provided when available.

Table 3 below depicts another possible gene ranking scheme for the relative infertility, subfertility, or premature decline in fertility risk associated with novel or common mutations or variants in a fertility gene. Table 3 contains the 11 genes, listed in order from most to least statistically significant, that were determined to be statistically significantly correlated with infertility risk in a study of unexplained female infertilty based on variants detected in the coding, non-coding, and conserved upstream and downstream regions of the fertility gene. P-values<0.025 are considered statistically significant, and all other fertility genes did not fit the pass the significance test for inclusion and ranking in this list. For the gene level analysis, we first compute a gene variant score for the entire transcript and flanking evolutionarily conserved regions for each individual/gene. The gene variant score represents the variability of the gene in an individual and is computed as the sum of the proportion of variant locations within that gene and its evolutionarily conserved regions flanking the gene for that individual. A series of linear regression models are fit, where the outcome variable is the gene variant score for a given gene, and the independent variables are group (infertile vs control) and principal component derived ethnicity (continuous). The p-value for group is used for statistical inference. The model is fit once for each gene.

TABLE 3

Fertility genes demonstrating statistical significance at the entire gene level for infertility risk ranked based on p-values, observed in a study of unexplained female infertility.

| Gene | Celmatix Gene ID | Entrez ID | HGNC ID | P-value |
|---|---|---|---|---|
| PADI6 | CMX-G0000000344 | 353238 | 20449 | 0.00079599 |
| CGB | CMX-G0000027860 | 1082 | 1886 | 0.000983714 |
| PMS2 | CMX-G0000011251 | 5395 | 9122 | 0.001500248 |

TABLE 3-continued

Fertility genes demonstrating statistical significance at the entire gene level for infertility risk ranked based on p-values, observed in a study of unexplained female infertility.

| Gene | Celmatix Gene ID | Entrez ID | HGNC ID | P-value |
|---|---|---|---|---|
| ESR2 | CMX-G0000021326 | 2100 | 3468 | 0.004733531 |
| UIMC1 | CMX-G0000009362 | 51720 | 30298 | 0.005170633 |
| ZP1 | CMX-G0000017558 | 22917 | 13187 | 0.00852914 |
| MDM2 | CMX-G0000019503 | 4193 | 6973 | 0.009794758 |
| BRCA2 | CMX-G0000020222 | 675 | 1101 | 0.019744499 |
| TGFB1 | CMX-G0000027588 | 7040 | 11766 | 0.020358934 |
| CDKN1C | CMX-G0000016717 | 1028 | 1786 | 0.022605239 |
| TAF4B | CMX-G0000026229 | 6875 | 11538 | 0.024673723 |

In particular embodiments, the infertility-associated genetic region is a gene (including exons, introns, and evolutionarily conserved regions of DNA flanking either side of said gene) that impacts fertility selected from the genes shown in Table 4 below. In Table 4, HGNC (http://www.genenames.org/) reference numbers are provided when available.

Table 4 below depicts another possible gene ranking scheme for the relative infertility, subfertility, or premature decline in fertility risk associated with novel or common mutations or variants in a fertility gene. Table 4 contains the top ranked 100 fertility genes, listed in order from most to least likely for variants in that gene to affect fertility. Genes are ranked according to a Celmatix Fertilome™ Score, G1Version2, that reflects the likelihood a gene is involved in fertility or reproduction. This score is computed using a database of mined and curated data, containing attributes for each gene in the genome (See FIGS. 5 and 6). These attributes include: diseases and disorders related to infertility, molecular pathways, molecular interactions, gene clusters, mouse phenotypes associated with each gene, gene expression data in reproductive tissues, proteomics data in oocytes, and accrued information from scientific publications through text-mining.

The process for ranking fertility-related attributes of a gene or genetic region (locus) to obtain an infertility score is called the SESMe algorithm. The SESMe algorithm is applied to a database of features and attributes that might make a particular gene important for fertility. The algorithm assigns a score and a relative weight to each feature then ranks genetic regions from most to least important (or vice versa) by weighting features and attributes associated with that genetic region. For example, a score is assigned to a gene by compiling the combined weighted values of attributes associated with that gene. After each gene is scored based on its weighted attributes, the genes can be ranked in order of importance in accordance with their score. The weighted value for each infertility attribute may be scaled in any manner including and not limited to assigning a positive or negative integer to reflect the significance or severity of the attribute to infertility.

In certain embodiments, the weighted value for gene infertility attributes may be on a scale from −10 to +10. A +10 may indicate that an attribute of a gene being scored is highly associated with infertility because that attribute is prevalently found in infertile patient populations. A +4 may represent an attribute that is a latent infertility marker, meaning it will not cause infertility on its own, but may lead to infertility upon influence of external factors such as aging and smoking. Whereas +2 may represent an attribute found in some infertile patients but nothing directly relates the attribute to infertility. A zero on the scale may include an attribute not yet known to have any effect or any negative effect towards infertility. A −10 may include an attribute shown not to affect infertility whatsoever. Further, embodiments provide for the weighted scale to include a +1 for attributes that are commonly found in infertile patient populations, 0.5 for attributes similar to those found in infertile patient populations, and 0 for attributes without a causal link to infertility.

In addition, weighted values for attributes may be normalized based on the known significance of that attribute towards infertility. For example and in certain embodiments, when scoring attributes of a particular gene, each attribute may be assigned a 0 if the attribute is absent and a 1 if the attribute is present. The attributes may then be normalized based on the infertility significance of that attribute. For example, if the attribute is a genetic mutation known to be associated with infertility, then that attribute may be normalized by a factor of 5. In another example, if the attribute is a signaling pathway defect sometimes associated with infertility, then that attribute may be normalized by a factor of 2.

Table 4, provided below, lists 100 Human Fertility Genes that were ranked by weighing attributes associated with the gene in accordance with methods of the invention.

TABLE 4

List of Top 100 Human Fertility Genes based on the Fertilome ™ Score, G1Version2.

| Rank | Gene Symbol | Celmatix Gene ID | Entrez Gene ID | HGNC Gene ID | Celmatix Fertilome ™ Score |
|---|---|---|---|---|---|
| 1 | C6orf221 | CMX-G0000010478 | 154288 | 33699 | 15 |
| 2 | NLRP5 | CMX-G0000028192 | 126206 | 21269 | 15 |
| 3 | ZP3 | CMX-G0000011947 | 7784 | 13189 | 12.93 |
| 4 | FIGLA | CMX-G0000003616 | 344018 | 24669 | 12 |
| 5 | PADI6 | CMX-G0000000344 | 353238 | 20449 | 12 |
| 6 | DNMT1 | CMX-G0000026880 | 1786 | 2976 | 11.67 |
| 7 | ZP2 | CMX-G0000023549 | 7783 | 13188 | 11.67 |
| 8 | FSHR | CMX-G0000003464 | 2492 | 3969 | 11.37 |
| 9 | OOEP | CMX-G0000010479 | 441161 | 21382 | 11 |
| 10 | FOXO3 | CMX-G0000010672 | 2309 | 3821 | 10.39 |
| 11 | ACVR1B | CMX-G0000019186 | 91 | 172 | 10.14 |
| 12 | CGA | CMX-G0000010560 | 1081 | 1885 | 10.04 |
| 13 | INHA | CMX-G0000004914 | 3623 | 6065 | 10.02 |
| 14 | LHCGR | CMX-G0000003462 | 3973 | 6585 | 10.01 |
| 15 | DPPA3 | CMX-G0000018719 | 359787 | 19199 | 10 |
| 16 | KDM1B | CMX-G0000009642 | 221656 | 21577 | 10 |
| 17 | NOBOX | CMX-G0000012690 | 135935 | 22448 | 10 |
| 18 | NPM2 | CMX-G0000013114 | 10361 | 7930 | 10 |
| 19 | ESR1 | CMX-G0000011002 | 2099 | 3467 | 9.91 |
| 20 | AURKA | CMX-G0000028967 | 6790 | 11393 | 9.84 |
| 21 | BRCA2 | CMX-G0000020222 | 675 | 1101 | 9.75 |
| 22 | WT1 | CMX-G0000017126 | 7490 | 12796 | 9.53 |
| 23 | CBS | CMX-G0000029408 | 875 | 1550 | 9.49 |
| 24 | CDKN1C | CMX-G0000016717 | 1028 | 1786 | 9.37 |
| 25 | IGF1 | CMX-G0000019714 | 3479 | 5464 | 9.35 |
| 26 | HAND2 | CMX-G0000007954 | 9464 | 4808 | 9.17 |
| 27 | GDF9 | CMX-G0000008902 | 2661 | 4224 | 9 |
| 28 | MAD2L1 | CMX-G0000007650 | 4085 | 6763 | 9 |
| 29 | ZAR1 | CMX-G0000007128 | 326340 | 21436 | 9 |
| 30 | FOXL2 | CMX-G0000006297 | 668 | 1092 | 8.88 |
| 31 | BARD1 | CMX-G0000004834 | 580 | 952 | 8.54 |
| 32 | FMN2 | CMX-G0000002910 | 56776 | 14074 | 8.4 |
| 33 | TACC3 | CMX-G0000006818 | 10460 | 11524 | 8.39 |
| 34 | MYC | CMX-G0000013826 | 4609 | 7553 | 8.25 |
| 35 | IL11RA | CMX-G0000014249 | 3590 | 5967 | 7.9 |
| 36 | MCM8 | CMX-G0000028433 | 84515 | 16147 | 7.85 |
| 37 | LHB | CMX-G0000027859 | 3972 | 6584 | 7.82 |
| 38 | TAF4B | CMX-G0000026229 | 6875 | 11538 | 7.68 |
| 39 | USP9X | CMX-G0000030612 | 8239 | 12632 | 7.67 |
| 40 | PRLR | CMX-G0000008271 | 5618 | 9446 | 7.58 |
| 41 | HSF1 | CMX-G0000013948 | 3297 | 5224 | 7.35 |
| 42 | FSHB | CMX-G0000017113 | 2488 | 3964 | 7.33 |
| 43 | ZP1 | CMX-G0000017558 | 22917 | 13187 | 7.29 |
| 44 | MDM2 | CMX-G0000019503 | 4193 | 6973 | 7.27 |
| 45 | BMP15 | CMX-G0000030783 | 9210 | 1068 | 7.25 |
| 46 | GPC3 | CMX-G0000031486 | 2719 | 4451 | 7.11 |
| 47 | PRDM1 | CMX-G0000010653 | 639 | 9346 | 7.05 |
| 48 | FST | CMX-G0000008371 | 10468 | 3971 | 7 |
| 49 | EZH2 | CMX-G0000012702 | 2146 | 3527 | 6.91 |
| 50 | SMAD2 | CMX-G0000026329 | 4087 | 6768 | 6.89 |
| 51 | NODAL | CMX-G0000015959 | 4838 | 7865 | 6.88 |
| 52 | ACVR1 | CMX-G0000004407 | 90 | 171 | 6.81 |
| 53 | HSD17B12 | CMX-G0000017190 | 51144 | 18646 | 6.71 |
| 54 | BRCA1 | CMX-G0000025305 | 672 | 1100 | 6.67 |
| 55 | DICER1 | CMX-G0000021645 | 23405 | 17098 | 6.53 |
| 56 | ESR2 | CMX-G0000021326 | 2100 | 3468 | 6.47 |

TABLE 4-continued

List of Top 100 Human Fertility Genes based on the Fertilome™ Score, G1Version2.

| Rank | Gene Symbol | Celmatix Gene ID | Entrez Gene ID | HGNC Gene ID | Celmatix Fertilome™ Score |
|---|---|---|---|---|---|
| 57 | MDM4 | CMX-G0000002542 | 4194 | 6974 | 6.42 |
| 58 | AR | CMX-G0000030935 | 367 | 644 | 6.41 |
| 59 | SCARB1 | CMX-G0000019991 | 949 | 1664 | 6.39 |
| 60 | CDKN1B | CMX-G0000018846 | 1027 | 1785 | 6.25 |
| 61 | TP53 | CMX-G0000024614 | 7157 | 11998 | 6.23 |
| 62 | NOG | CMX-G0000025542 | 9241 | 7866 | 6.22 |
| 63 | IL6ST | CMX-G0000008398 | 3572 | 6021 | 6.13 |
| 64 | DAZL | CMX-G0000005296 | 1618 | 2685 | 6 |
| 65 | NLRP11 | CMX-G0000028188 | 204801 | 22945 | 6 |
| 66 | NLRP13 | CMX-G0000028190 | 126204 | 22937 | 6 |
| 67 | NLRP8 | CMX-G0000028191 | 126205 | 22940 | 6 |
| 68 | NLRP9 | CMX-G0000028184 | 338321 | 22941 | 6 |
| 69 | ZFX | CMX-G0000030503 | 7543 | 12869 | 5.67 |
| 70 | TFPI | CMX-G0000004632 | 7035 | 11760 | 5.36 |
| 71 | HSD17B7 | CMX-G0000002148 | 51478 | 5215 | 5.32 |
| 72 | TP63 | CMX-G0000006674 | 8626 | 15979 | 5.28 |
| 73 | NR5A1 | CMX-G0000015051 | 2516 | 7983 | 5.24 |
| 74 | BMP7 | CMX-G0000028985 | 655 | 1074 | 5.09 |
| 75 | CGB | CMX-G0000027860 | 1082 | 1886 | 5 |
| 76 | CGB5 | CMX-G0000027866 | 93659 | 16452 | 5 |
| 77 | DDX43 | CMX-G0000010483 | 55510 | 18677 | 5 |
| 78 | FMR1 | CMX-G0000031614 | 2332 | 3775 | 5 |
| 79 | LIN28B | CMX-G0000010647 | 389421 | 32207 | 5 |
| 80 | NLRP14 | CMX-G0000016919 | 338323 | 22939 | 5 |
| 81 | NLRP4 | CMX-G0000028189 | 147945 | 22943 | 5 |
| 82 | NLRP7 | CMX-G0000028139 | 199713 | 22947 | 5 |
| 83 | PROK1 | CMX-G0000001385 | 84432 | 18454 | 5 |
| 84 | SPIN1 | CMX-G0000014689 | 1927 | 11243 | 5 |
| 85 | TFPI2 | CMX-G0000012044 | 7980 | 11761 | 5 |
| 86 | ZP4 | CMX-G0000002903 | 57829 | 15770 | 5 |
| 87 | ESRRB | CMX-G0000021489 | 2103 | 3473 | 4.8 |
| 88 | UBE3A | CMX-G0000022200 | 7337 | 12496 | 4.76 |
| 89 | SUZ12 | CMX-G0000025003 | 23512 | 17101 | 4.73 |
| 90 | XIST | CMX-G0000031023 | 7503 | 12810 | 4.7 |
| 91 | ATM | CMX-G0000018234 | 472 | 795 | 4.62 |
| 92 | AURKB | CMX-G0000024639 | 9212 | 11390 | 4.55 |
| 93 | STK3 | CMX-G0000013673 | 6788 | 11406 | 4.52 |
| 94 | POLG | CMX-G0000023009 | 5428 | 9179 | 4.51 |
| 95 | CDX2 | CMX-G0000020191 | 1045 | 1806 | 4.46 |
| 96 | TP73 | CMX-G0000000110 | 7161 | 12003 | 4.43 |
| 97 | MTOR | CMX-G0000000201 | 2475 | 3942 | 4.42 |
| 98 | AHR | CMX-G0000011332 | 196 | 348 | 4.41 |
| 99 | LIF | CMX-G0000029949 | 3976 | 6596 | 4.38 |
| 100 | PRKRA | CMX-G0000004587 | 8575 | 9438 | 4.38 |

In particular embodiments, the infertility-associated genetic region is a gene (including exons, introns, and evolutionarily conserved regions of DNA flanking either side of said gene) that impacts fertility selected from the genes shown in Table 5 below. In Table 5, HGNC (http://www.genenames.org/) reference numbers are provided when available.

Table 5 below depicts another possible gene ranking scheme for the relative infertility, subfertility, or premature decline in fertility risk associated with novel or common mutations or variants in a fertility gene. Table 5 contains the top ranked 100 fertility genes, listed in order from most to least likely for variants in that gene to affect fertility. Genes are ranked according to a Celmatix Fertilome™ Score, G1Version3, that reflects the likelihood a gene is involved in fertility or reproduction. This score is computed using a database of mined and curated data, containing attributes for each gene in the genome (See FIGS. 5 and 6). These attributes include: diseases and disorders related to infertility, molecular pathways, molecular interactions, gene clusters, mouse phenotypes associated with each gene, gene expression data in reproductive tissues, proteomics data in oocytes, and accrued information from scientific publications through text-mining. The Celmatix Fertilome™ Score, G1Version3 differs from G1Version2 (Table 4) because it contains more fertility genes as an input for the score calculation.

TABLE 5

List of Top 100 Human Fertility Genes based on the Fertilome ™ Score, G1Version3.

| Rank | Gene Symbol | Celmatix Gene ID | Entrez Gene ID | HGNC Gene ID | Celmatix Fertilome ™ Score |
|---|---|---|---|---|---|
| 1 | C6orf221 | CMX-G0000010478 | 154288 | 33699 | 15 |
| 2 | NLRP5 | CMX-G0000028192 | 126206 | 21269 | 15 |
| 3 | TCL1A | CMX-G0000021654 | 8115 | 11648 | 14 |
| 4 | ZP3 | CMX-G0000011947 | 7784 | 13189 | 12.93 |
| 5 | FIGLA | CMX-G0000003616 | 344018 | 24669 | 12 |
| 6 | PADI6 | CMX-G0000000344 | 353238 | 20449 | 12 |
| 7 | RSPO1 | CMX-G0000000687 | 284654 | 21679 | 12 |
| 8 | EPHA1 | CMX-G0000012650 | 2041 | 3385 | 11.82 |
| 9 | DNMT1 | CMX-G0000026880 | 1786 | 2976 | 11.67 |
| 10 | ZP2 | CMX-G0000023549 | 7783 | 13188 | 11.67 |
| 11 | MOS | CMX-G0000013392 | 4342 | 7199 | 11.5 |
| 12 | FSHR | CMX-G0000003464 | 2492 | 3969 | 11.37 |
| 13 | OOEP | CMX-G0000010479 | 441161 | 21382 | 11 |
| 14 | CUL1 | CMX-G0000012701 | 8454 | 2551 | 10.67 |
| 15 | HSP90B1 | CMX-G0000019724 | 7184 | 12028 | 10.57 |
| 16 | FOXO3 | CMX-G0000010672 | 2309 | 3821 | 10.39 |
| 17 | KISS1 | CMX-G0000002533 | 3814 | 6341 | 10.21 |
| 18 | ACVR1B | CMX-G0000019186 | 91 | 172 | 10.14 |
| 19 | CGA | CMX-G0000010560 | 1081 | 1885 | 10.04 |
| 20 | INHA | CMX-G0000004914 | 3623 | 6065 | 10.02 |
| 21 | LHCGR | CMX-G0000003462 | 3973 | 6585 | 10.01 |
| 22 | DPPA3 | CMX-G0000018719 | 359787 | 19199 | 10 |
| 23 | KDM1B | CMX-G0000009642 | 221656 | 21577 | 10 |
| 24 | NOBOX | CMX-G0000012690 | 135935 | 22448 | 10 |
| 25 | NPM2 | CMX-G0000013114 | 10361 | 7930 | 10 |
| 26 | PRMT3 | CMX-G0000017073 | 10196 | 30163 | 10 |
| 27 | GJA4 | CMX-G0000000643 | 2701 | 4278 | 9.92 |
| 28 | ESR1 | CMX-G0000011002 | 2099 | 3467 | 9.91 |
| 29 | SFRP4 | CMX-G0000011506 | 6424 | 10778 | 9.89 |
| 30 | AURKA | CMX-G0000028967 | 6790 | 11393 | 9.84 |
| 31 | BRCA2 | CMX-G0000020222 | 675 | 1101 | 9.75 |
| 32 | WT1 | CMX-G0000017126 | 7490 | 12796 | 9.53 |
| 33 | CBS | CMX-G0000029408 | 875 | 1550 | 9.49 |
| 34 | CDKN1C | CMX-G0000016717 | 1028 | 1786 | 9.37 |
| 35 | IGF1 | CMX-G0000019714 | 3479 | 5464 | 9.35 |
| 36 | PLCB1 | CMX-G0000028445 | 23236 | 15917 | 9.33 |
| 37 | CEP290 | CMX-G0000019604 | 80184 | 29021 | 9.3 |
| 38 | MSH5 | CMX-G0000010000 | 4439 | 7328 | 9.29 |
| 39 | HAND2 | CMX-G0000007954 | 9464 | 4808 | 9.17 |
| 40 | GDF9 | CMX-G0000008902 | 2661 | 4224 | 9 |
| 41 | MAD2L1 | CMX-G0000007650 | 4085 | 6763 | 9 |
| 42 | TNFAIP6 | CMX-G0000004377 | 7130 | 11898 | 9 |
| 43 | ZAR1 | CMX-G0000007128 | 326340 | 20436 | 9 |
| 44 | FOXL2 | CMX-G0000006297 | 668 | 1092 | 8.88 |
| 45 | PCNA | CMX-G0000028417 | 5111 | 8729 | 8.78 |
| 46 | YBX2 | CMX-G0000024578 | 51087 | 17948 | 8.57 |
| 47 | BARD1 | CMX-G0000004834 | 580 | 952 | 8.57 |
| 48 | AMBP | CMX-G0000014963 | 259 | 453 | 8.4 |
| 49 | FMN2 | CMX-G0000002910 | 56776 | 14074 | 8.4 |
| 50 | NCOA2 | CMX-G0000013477 | 10499 | 7669 | 8.4 |
| 51 | TEX12 | CMX-G0000018279 | 56158 | 11734 | 8.4 |
| 52 | TACC3 | CMX-G0000006818 | 10460 | 11524 | 8.39 |
| 53 | PGR | CMX-G0000018173 | 5241 | 8910 | 8.37 |
| 54 | FANCC | CMX-G0000014774 | 2176 | 3584 | 8.25 |
| 55 | MYC | CMX-G0000013826 | 4609 | 7553 | 8.25 |
| 56 | FGF8 | CMX-G0000016316 | 2253 | 3686 | 8.23 |
| 57 | SMAD5 | CMX-G0000008943 | 4090 | 6771 | 8.12 |
| 58 | CCS | CMX-G0000017793 | 9973 | 1613 | 8 |
| 59 | MSH4 | CMX-G0000001108 | 4438 | 7327 | 8 |
| 60 | SPO11 | CMX-G0000028986 | 23626 | 11250 | 8 |
| 61 | SYCE1 | CMX-G0000016602 | 93426 | 28852 | 8 |
| 62 | SYCP1 | CMX-G0000001457 | 6847 | 11487 | 8 |
| 63 | TFAP2C | CMX-G0000028982 | 7022 | 11744 | 8 |
| 64 | WNT7A | CMX-G0000005260 | 7476 | 12786 | 7.96 |
| 65 | IL11RA | CMX-G0000014249 | 3590 | 5967 | 7.9 |
| 66 | MCM8 | CMX-G0000028433 | 84515 | 16147 | 7.85 |
| 67 | SYCP2 | CMX-G0000029020 | 10388 | 11490 | 7.85 |
| 68 | INHBA | CMX-G0000011550 | 3624 | 6066 | 7.83 |
| 69 | MGAT1 | CMX-G0000009451 | 4245 | 7044 | 7.83 |
| 70 | LHB | CMX-G0000027859 | 3972 | 6584 | 7.82 |
| 71 | CYP19A1 | CMX-G0000022537 | 1588 | 2594 | 7.74 |
| 72 | GGT1 | CMX-G0000029874 | 2678 | 4250 | 7.71 |
| 73 | TAFB4 | CMX-G0000026229 | 6875 | 11538 | 7.68 |
| 74 | SMC1B | CMX-G0000030247 | 27127 | 11112 | 7.67 |

TABLE 5-continued

List of Top 100 Human Fertility Genes based on the Fertilome™ Score, G1Version3.

| Rank | Gene Symbol | Celmatix Gene ID | Entrez Gene ID | HGNC Gene ID | Celmatix Fertilome™ Score |
|---|---|---|---|---|---|
| 75 | USP9X | CMX-G0000030612 | 8239 | 12632 | 7.67 |
| 76 | PRLR | CMX-G0000008271 | 5618 | 9446 | 7.58 |
| 77 | DNMT3B | CMX-G0000028640 | 1789 | 2979 | 7.54 |
| 78 | SOD1 | CMX-G0000029263 | 6647 | 11179 | 7.54 |
| 79 | SH2B1 | CMX-G0000023639 | 25970 | 30417 | 7.5 |
| 80 | HOXA11 | CMX-G0000011417 | 3207 | 5101 | 7.48 |
| 81 | UBB | CMX-G0000024729 | 7314 | 12463 | 7.43 |
| 82 | HSF1 | CMX-G0000013948 | 3297 | 5224 | 7.35 |
| 83 | CYP17A1 | CMX-G0000016340 | 1586 | 2593 | 7.33 |
| 84 | FSHB | CMX-G0000017113 | 2488 | 3964 | 7.33 |
| 85 | SYCP3 | CMX-G0000019706 | 50511 | 18130 | 7.33 |
| 86 | NOS3 | CMX-G0000012751 | 4846 | 7876 | 7.31 |
| 87 | ZP1 | CMX-G0000017558 | 22917 | 13187 | 7.29 |
| 88 | GNRHR | CMX-G0000007221 | 2798 | 4421 | 7.27 |
| 89 | MDM2 | CMX-G0000019503 | 4193 | 6973 | 7.27 |
| 90 | BMP15 | CMX-G0000030783 | 9210 | 1068 | 7.25 |
| 91 | KDM1A | CMX-G0000000422 | 23028 | 29079 | 7.25 |
| 92 | MDK | CMX-G0000017221 | 4192 | 6972 | 7.21 |
| 93 | MSX2 | CMX-G0000009331 | 4488 | 7392 | 7.21 |
| 94 | CTNNB1 | CMX-G0000005462 | 1499 | 2514 | 7.2 |
| 95 | NRIP1 | CMX-G0000029160 | 8204 | 8001 | 7.2 |
| 96 | UBC | CMX-G0000019992 | 7316 | 12468 | 7.2 |
| 97 | FKBP4 | CMX-G0000018615 | 2288 | 3720 | 7.19 |
| 98 | MLH3 | CMX-G0000021470 | 27030 | 7128 | 7.14 |
| 99 | MSX1 | CMX-G0000006873 | 4487 | 7391 | 7.13 |
| 100 | GPC3 | CMX-G0000031486 | 2719 | 4451 | 7.11 |

In particular embodiments, the infertility-associated genetic region is a gene (including exons, introns, and evolutionarily conserved regions of DNA flanking either side of said gene) that impacts fertility selected from the genes shown in Table 6 below. In Table 5, HGNC (http://www.genenames.org/) reference numbers are provided when available.

Table 6 below depicts another possible gene ranking scheme for the relative infertility, subfertility, or premature decline in fertility risk associated with novel or common mutations or variants in a fertility gene. Table 6 contains the top ranked fertility genes based on a comparison of how often the gene appears in one of the lists above (Tables 1-5). This list represents the top 20 genetic regions with utility for diagnosing female infertility, subfertility, or premature decline in fertility. These targets were identified using a compendium of factors: 1) Carrying statistically significant genetic mutations at the coding level in a pilot study, 2) Carrying statistically significant genetic mutations at the coding level in a pilot study, 3) Carrying genetic variations in our pilot study that impact the biochemical properties of the gene, 4) Highly ranked in our Celmatix Fertilome™ Score system, that reflects the likelihood a gene is involved in fertility or reproduction.

TABLE 6

List of the Top 20 Fertility Genes (arranged in alphabetical order)

| Gene Symbol | Celmatix Gene ID | Entrez Gene ID | HGNC Gene ID |
|---|---|---|---|
| BARD1 | CMX-G0000004834 | 580 | 952 |
| C6orf221 | CMX-G0000010478 | 154288 | 33699 |
| DNMT1 | CMX-G0000026880 | 1786 | 2976 |
| FMR1 | CMX-G0000031614 | 2332 | 3775 |
| FOXO3 | CMX-G0000010672 | 2309 | 3821 |
| MUC4 | CMX-G0000006719 | 4585 | 7514 |
| NLRP11 | CMX-G0000028188 | 204801 | 22945 |
| NLRP14 | CMX-G0000016919 | 338323 | 22939 |
| NLRP5 | CMX-G0000028192 | 126206 | 21269 |
| NLRP8 | CMX-G0000028191 | 126205 | 22940 |
| NPM2 | CMX-G0000013114 | 10361 | 7930 |
| PADI6 | CMX-G0000000344 | 353238 | 20449 |
| PMS2 | CMX-G0000011251 | 5395 | 9122 |
| SCARB1 | CMX-G0000019991 | 949 | 1664 |
| SPIN1 | CMX-G0000014689 | 10927 | 11243 |
| TACC3 | CMX-G0000006818 | 10460 | 11524 |
| ZP1 | CMX-G0000017558 | 22917 | 13187 |
| ZP2 | CMX-G0000023549 | 7783 | 13188 |
| ZP3 | CMX-G0000011947 | 7784 | 13189 |
| ZP4 | CMX-G0000002903 | 57829 | 15770 |

In particular embodiments, the infertility-associated genetic region is a gene (including exons, introns, and evolutionarily conserved regions of DNA flanking either side of said gene) that impacts fertility selected from the genes shown in Table 7 below. In Table 7, HGNC (http://www.genenames.org/) reference numbers are provided when available.

Table 7 below depicts all of the biologically and/or statistically significant variants detected in the genes depicted in Table 6 in a genetic study of female infertility. Genetic variants considered to be biologically significant include mutations that result in a change: 1) to a different amino acid predicted to alter the folding and/or structure of the encoded protein, 2) to a different amino acid occurring at a highly evolutionarily conserved site, 3) that introduces a premature stop termination signal, 4) that causes a stop termination signal to be lost, 5) that introduces a new start codon, 6) that causes a start codon to be lost, 7) that disrupts a splicing signal, 8) that alters the reading frame or 9) that alters the dosage of encoded protein or RNA. All genetic variants detected from resequencing exclude sites at the single nucleotide level where the variant allele is detected in only one chromosome (singletons) and sites sequenced in only one individual. Structural variants impacting biological function are also reported. Using these criteria applied to targeted re-sequencing data from a study of infertile females, we detected 490 variants, of which 379 are listed in Table 7.

For the statistically significant variant level analysis, a series of logistic regression models are fit, where the outcome variable is the binary indicator of variant status for a given location, and the independent variables are group (infertile vs. control) and principal component-derived ethnicity (continuous). The p-value and odds ratio for group are used for statistical inference. The model is fit once for each location. P-values<0.001 are considered statistically significant. We performed a SNP association study by targeted re-sequencing and identified a total of 147 SNPs significantly associated with female infertility (of which 52 are reported in Table 7). Each variant was classified as novel or known. Novel sites are excluded from the p-value computation. For known variants, we apply a series of logistic regression models where the outcome variable is the binary indicator of variant status for a given location, and the independent variables are group (infertile vs. control) and principal component-derived ethnicity (continuous). The p-value and odds ratio for group are used for statistical inference. P-values less than 0.001 were considered significant. Position refers to NCBI Build 37. Alleles are reported on the forward strand. Ref=Reference allele, Alt=Variant allele.

TABLE 7

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| APOA1 | CMX-G0000018327 | CMX-V1388879 | chr11:112553969-126265772 | NA | CNV gain | APOA1 (3 exons) | NA |
| ASCL2 | CMX-G0000016707 | CMX-V1067111 | chr11:2234334-2298706 | NA | CNV gain | ASCL2 (1 exon) | NA |
| BARD1 | CMX-G0000004834 | CMX-V9083698 | chr2:215674224 | G | A | Drastic nonsynonymous | NA |
| BARD1 | CMX-G0000004834 | CMX-V9083699 | chr2:215595645 | C | T | Start codon lost | NA |
| BARD1 | CMX-G0000004834 | CMX-V9083700 | chr2:215674323 | C | G | Start codon gained | NA |
| BARD1 | CMX-G0000004834 | CMX-SV00001 | chr2:215645502 | GTGGTGAAGAACATTCAGGCAA | G | Codon deletion | NA |
| BARD1 | CMX-G0000004834 | CMX-V9084177 | chr2:215742204 | G | T | NA | 6.77E−05 |
| BMP15 | CMX-G0000030783 | CMX-V1250077 | chrX:50639969-50981841 | NA | CNV gain | BMP15 (2 exons) | NA |
| BMP6 | CMX-G0000009564 | CMX-V1247770 | chr6:7726514-7727614 | NA | CNV loss | BMP6 (1 exon) | NA |
| BMP6 | CMX-G0000009564 | CMX-V1166409 | chr6:7724859-7728905 | NA | CNV loss | BMP6 (1 exon) | NA |
| C6orf221 | CMX-G0000010478 | CMX-V9083706 | chr6:74073531 | C | G | Drastic nonsynonymous | NA |
| CASP8 | CMX-G0000004721 | CMX-V1843349 | chr2:201851129-203110758 | NA | CNV loss | CASP8 (2 exons) | NA |
| CSF1, UBL4B | CMX-G0000001374, CMX-G0000001378 | CMX-V1667025 | chr1:110441465-110831379 | NA | CNV loss | CSF1 (4 exons), UBL4B (1 exon) | NA |
| CSF2 | CMX-G0000008885 | CMX-V1456214 | chr5:128320218-131440732 | NA | CNV loss | CSF2 (4 exons) | NA |
| CYP11B1 | CMX-G0000013888 | CMX-V1957973 | chr8:143951813-143958440 | NA | CNV gain | CYP11B1 (4 exons) | NA |
| CYP11B1 | CMX-G0000013888 | CMX-V1609269 | chr8:143953403-143991713 | NA | CNV gain | CYP11B1 (4 exons) | NA |
| DCTPP1, SEPHS2, TGFB1I1, VKORC1 | CMX-G0000023705, CMX-G0000023707, CMX-G0000023757, CMX-G0000023741 | CMX-V1070550 | chr16:30347689-31632796 | NA | CNV gain | DCTPP1 (1 exon), SEPHS2 (1 exon), TGFB1I1 (3 exons), VKORC1 (1 exon) | NA |
| DNMT1 | CMX-G0000026880 | CMX-V9083720 | chr19:10291181 | T | C | Drastic nonsynonymous | NA |
| ECHS1 | CMX-G0000016594 | CMX-V1101514 | chr10:135087081-135243330 | NA | CNV gain | ECHS1 (8 exons) | NA |
| ECHS1 | CMX-G0000016594 | CMX-V1131837 | chr10:135088839-135243616 | NA | CNV loss | ECHS1 (8 exons) | NA |
| ECHS1 | CMX-G0000016594 | CMX-V1335364 | chr10:135087962-135243616 | NA | CNV gain | ECHS1 (8 exons) | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| EFNA4 | CMX-G0000001896 | CMX-V1267541 | chr1:154354576-155066744 | NA | CNV loss | EFNA4 (4 exons) | NA |
| EFNB3 | CMX-G0000024616 | CMX-V1295730 | che17:7135639-7702377 | NA | CNV gain | EFNB3 (5 exons) | NA |
| EIF3CL | CMX-G0000023621 | CMX-V1992389 | chr16:28197032-28410526 | NA | CNV loss | EIF3CL (13 exons) | NA |
| EPHA5 | CMX-G0000007213 | CMX-V1585842 | chr4:66114884-66870165 | NA | CNV loss | EPHA5 (17 exons) | NA |
| EPHA7 | CMX-G0000010603 | CMX-V1939194 | chr6:94015504-95364976 | NA | CNV loss | EPHA7 (3 exons) | NA |
| EPHA8 | CMX-G0000000415 | CMX-V1493926 | chr1:22906197-22914076 | NA | CNV loss | EPHA8 (1 exon) | NA |
| EPHA8 | CMX-G0000000415 | CMX-V1680494 | chr1:22905731-22915711 | NA | CNV loss | EPHA8 (2 exons) | NA |
| EPHA8 | CMX-G0000000415 | CMX-V1333389 | chr1:22904786-22915711 | NA | CNV loss | EPHA8 (2 exons) | NA |
| EPHA8 | CMX-G0000000415 | CMX-V1750787 | chr1:22906271-22915711 | NA | CNV loss | EPHA8 (2 exons) | NA |
| EPHA8 | CMX-G0000000415 | CMX-V1102470 | chr1:22906197-22915711 | NA | CNV loss | EPHA8 (1 exon) | NA |
| EPHA8 | CMX-G0000000415 | CMX-V1356293 | chr1:22905731-22915352 | NA | CNV loss | EPHA8 (1 exon) | NA |
| EPHA8 | CMX-G0000000415 | CMX-V1845595 | chr1:22905731-22913963 | NA | CNV loss | EPHA8 (1 exon) | NA |
| EPHA8 | CMX-G0000000415 | CMX-V1973671 | chr1:22906526-22913011 | NA | CNV loss | EPHA8 (1 exon) | NA |
| EPHA8 | CMX-G0000000415 | CMX-V1086453 | chr1:22905731-22916983 | NA | CNV loss | EPHA8 (2 exons) | NA |
| EPHA8 | CMX-G0000000415 | CMX-V1138079 | chr1:22904856-22913700 | NA | CNV loss | EPHA8 (1 exon) | NA |
| EPHA8 | CMX-G0000000415 | CMX-V1957426 | chr1:22904786-22914210 | NA | CNV loss | EPHA8 (1 exon) | NA |
| EPHA8 | CMX-G0000000415 | CMX-V1635641 | chr1:22906197-22915352 | NA | CNV loss | EPHA8 (1 exon) | NA |
| EPHA8 | CMX-G0000000415 | CMX-V1387198 | chr1:22905731-22914256 | NA | CNV loss | EPHA8 (1 exon) | NA |
| EPHA8 | CMX-G0000000415 | CMX-V1481340 | chr1:22906271-22913750 | NA | CNV loss | EPHA8 (1 exon) | NA |
| EPHA8 | CMX-G0000000415 | CMX-V1077862 | chr1:22904856-22913963 | NA | CNV loss | EPHA8 (1 exon) | NA |
| EPHA8 | CMX-G0000000415 | CMX-V1288029 | chr1:22904064-22914256 | NA | CNV loss | EPHA8 (1 exon) | NA |
| EPHA8 | CMX-G0000000415 | CMX-V1098423 | chr1:22906395-22913750 | NA | CNV loss | EPHA8 (1 exon) | NA |
| EPHA8 | CMX-G0000000415 | CMX-V1825294 | chr1:22906271-22914210 | NA | CNV loss | EPHA8 (1 exon) | NA |
| EPHA8 | CMX-G0000000415 | CMX-V1672255 | chr1:22906271-22915161 | NA | CNV loss | EPHA8 (1 exon) | NA |
| EPHA8 | CMX-G0000000415 | CMX-V1740010 | chr1:22906271-22914076 | NA | CNV loss | EPHA8 (1 exon) | NA |
| EPHA8 | CMX-G0000000415 | CMX-V1757241 | chr1:22904856-22915352 | NA | CNV loss | EPHA8 (1 exon) | NA |
| EPHA8 | CMX-G0000000415 | CMX-V1080982 | chr1:22906322-22914695 | NA | CNV loss | EPHA8 (1 exon) | NA |
| EPHA8 | CMX-G0000000415 | CMX-V1506728 | chr1:22905731-22913502 | NA | CNV loss | EPHA8 (1 exon) | NA |
| FGF8 | CMX-G0000016316 | CMX-V1202186 | chr10:103524444-103533748 | NA | CNV gain | FGF8 (2 exons) | NA |
| FGF8 | CMX-G0000016316 | CMX-V1242750 | chr10:103524714-103532892 | NA | CNV gain | FGF8 (2 exons) | NA |
| FGF8 | CMX-G0000016316 | CMX-V1059642 | chr10:103520069-103531134 | NA | CNV gain | FGF8 (1 exon) | NA |
| FGF8 | CMX-G0000016316 | CMX-V1478224 | chr10:103525082-103536399 | NA | CNV gain | FGF8 (6 exons) | NA |
| FMR1 | CMX-G0000031614 | CMX-V9083727 | chrX:147010263 | A | C | Drastic nonsynonymous | NA |
| FMR1 | CMX-G0000031614 | CMX-V9083728 | chrX:147014960 | C | T | Start codon gained | NA |
| FMR1 | CMX-G0000031614 | CMX-V9084252 | chrX:146126483 | G | A | NA | 0.000198744 |
| FMR1 | CMX-G0000031614 | CMX-V9084253 | chrX:146153970 | C | T | NA | 1.92E-05 |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| FMR1 | CMX-G0000031614 | CMX-V9084254 | chrX:146195865 | A | G | NA | 0.000371198 |
| FMR1 | CMX-G0000031614 | CMX-V9084255 | chrX:146221514 | C | T | NA | 0.000292157 |
| FMR1 | CMX-G0000031614 | CMX-V9084256 | chrX:146247740 | T | A | NA | 0.0001997 |
| FMR1 | CMX-G0000031614 | CMX-V9084257 | chrX:146255213 | G | A | NA | 0.000185975 |
| FMR1 | CMX-G0000031614 | CMX-V9084258 | chrX:146406319 | A | G | NA | 0.000262855 |
| FMR1 | CMX-G0000031614 | CMX-V9084259 | chrX:146994916 | A | G | NA | 0.000816693 |
| FMR1 | CMX-G0000031614 | CMX-V9084260 | chrX:147002992 | T | G | NA | 0.000810806 |
| FMR1 | CMX-G0000031614 | CMX-V9084261 | chrX:147003339 | A | G | NA | 0.000810806 |
| FMR1 | CMX-G0000031614 | CMX-V9084262 | chrX:147003794 | T | C | NA | 0.000810806 |
| FMR1 | CMX-G0000031614 | CMX-V9084263 | chrX:147024558 | A | T | NA | 0.000641561 |
| FMR1 | CMX-G0000031614 | CMX-V9084264 | chrX:147372528 | G | C | NA | 0.000633948 |
| FMR1 | CMX-G0000031614 | CMX-V9084265 | chrX:147397806 | A | G | NA | 0.000813685 |
| FMR1 | CMX-G0000031614 | CMX-V9084266 | chrX:147437683 | A | G | NA | 0.000784981 |
| FMR1 | CMX-G0000031614 | CMX-V9084267 | chrX:147449673 | T | C | NA | 0.000401568 |
| FMR1 | CMX-G0000031614 | CMX-V9084268 | chrX:147454832 | G | A | NA | 0.000965078 |
| FMR1 | CMX-G0000031614 | CMX-V9084269 | chrX:147454832 | G | T | NA | 0.000646517 |
| FMR1 | CMX-G0000031614 | CMX-V9084270 | chrX:147479861 | A | C | NA | 0.000646517 |
| FMR1 | CMX-G0000031614 | CMX-V9084271 | chrX:147480274 | A | G | NA | 0.000646517 |
| FMR1 | CMX-G0000031614 | CMX-V9084272 | chrX:147481891 | T | C | NA | 0.000646517 |
| FMR1 | CMX-G0000031614 | CMX-V9084273 | chrX:147482603 | A | G | NA | 0.000564877 |
| FMR1 | CMX-G0000031614 | CMX-V9084274 | chrX:147482630 | A | G | NA | 0.000458631 |
| FOXO3 | CMX-G0000010672 | CMX-V9084196 | chrX:108856108 | C | T | NA | 0.000232121 |
| FOXO3 | CMX-G0000010672 | CMX-V9084197 | chr6:109149693 | G | C | NA | 0.000344433 |
| FOXO3 | CMX-G0000010672 | CMX-V9084195 | chr6:108853361 | T | A | NA | 0.000176018 |
| FOXO3 | CMX-G0000010672 | CMX-V9084198 | chr6:109155789 | G | T | NA | 0.000641107 |
| FOXO3 | CMX-G0000010672 | CMX-V1295244 | chr6:108985148-108989762 | NA | CNV gain | FOXO3 (1 exon) | NA |
| FOXO3 | CMX-G0000010672 | CMX-V1963522 | chr6:108985507-108989056 | NA | CNV gain | FOXO3 (1 exon) | NA |
| FOXO3 | CMX-G0000010672 | CMX-V1963523 | chr6:108984930-108989762 | NA | CNV gain | FOXO3 (1 exon) | NA |
| FOXP3 | CMX-G0000030750 | CMX-V1008919 | chrX:48890221-49257528 | NA | CNV gain | FOXP3 (9 exons) | NA |
| GDF1 | CMX-G0000027183 | CMX-V1625432 | chr19:18872185-19535389 | NA | CNV gain | GDF1 (2 exons) | NA |
| GJA4, GJB3, GJB4 | CMX-G0000000643, CMX-G0000000642, CMX-G0000000641 | CMX-V1706868 | chr1:35000925-37866010 | NA | CNV gain | GJA4 (1 exon), GJB3 (1 exon), GJB4 (1 exon) | NA |
| GJD3 | CMX-G0000025169 | CMX-V1132225 | chr17:37952541-38532715 | NA | CNV gain | GJD3 (1 exon) | NA |
| GPC3 | CMX-G0000031486 | CMX-V1515961 | chrX:132613906-132779666 | NA | CNV gain | GPC3 (1 exon) | NA |
| IGF2 | CMX-G0000016702 | CMX-V1454080 | chr11:2127129-2173473 | NA | CNV gain | IGF2 (3 exons) | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| IGF2 | CMX-G0000016702 | CMX-V1542559 | chr11:2110901-2173938 | NA | CNV gain | IGF2 (3 exons) | NA |
| IGFBPL1 | CMX-G0000014341 | CMX-V1435664 | chr9:35776310-38419649 | NA | CNV loss | IGFBPL1 (3 exons) | NA |
| ISG15 | CMX-G0000000029 | CMX-V1111642 | chr1:940142-1016233 | NA | CNV gain | ISG15 (2 exons) | NA |
| ISG15 | CMX-G0000000029 | CMX-V1884847 | chr1:834638-1271900 | NA | CNV gain | ISG15 (2 exons) | NA |
| KISS1 | CMX-G0000002533 | CMX-V1823995 | chr1:202729101-205013246 | NA | CNV gain | KISS1 (2 exons) | NA |
| KISS1R | CMX-G0000026560 | CMX-V1469394 | chr19:867728-945645 | NA | CNV gain | KISS1R (2 exons) | NA |
| KISS1R | CMX-G0000026560 | CMX-V1974120 | chr19:867728-1126103 | NA | CNV gain | KISS1R (2 exons) | NA |
| KISS1R | CMX-G0000026560 | CMX-V1813360 | chr19:868013-1085518 | NA | CNV gain | KISS1R (2 exons) | NA |
| KISS1R | CMX-G0000026560 | CMX-V1883755 | chr19:866589-1232099 | NA | CNV gain | KISS1R (2 exons) | NA |
| LOXL4 | CMX-G0000016263 | CMX-V1039367 | chr10:100013106-100022354 | NA | CNV loss | LOXL4 (9 exons) | NA |
| LOXL4 | CMX-G0000016263 | CMX-V1620875 | chr10:100013359-100023161 | NA | CNV loss | LOXL4 (10 exons) | NA |
| LOXL4 | CMX-G0000016263 | CMX-V1806767 | chr10:100014360-100020546 | NA | CNV loss | LOXL4 (6 exons) | NA |
| LOXL4 | CMX-G0000016263 | CMX-V1954806 | chr10:100014176-100022354 | NA | CNV loss | LOXL4 (8 exons) | NA |
| LOXL4 | CMX-G0000016263 | CMX-V1107311 | chr10:100015459-100023313 | NA | CNV loss | LOXL4 (9 exons) | NA |
| LOXL4 | CMX-G0000016263 | CMX-V1373344 | chr10:100015459-100023369 | NA | CNV loss | LOXL4 (9 exons) | NA |
| LOXL4 | CMX-G0000016263 | CMX-V1073572 | chr10:100015459-100023161 | NA | CNV loss | LOXL4 (9 exons) | NA |
| LOXL4 | CMX-G0000016263 | CMX-V1348325 | chr10:100014551-100023161 | NA | CNV loss | LOXL4 (9 exons) | NA |
| LOXL4 | CMX-G0000016263 | CMX-V1321127 | chr10:100011910-100023369 | NA | CNV loss | LOXL4 (11 exons) | NA |
| LOXL4 | CMX-G0000016263 | CMX-V1323761 | chr10:100013876-103528663 | NA | CNV loss | LOXL4 (9 exons) | NA |
| LOXL4 | CMX-G0000016263 | CMX-V1275468 | chr10:100014176-100023161 | NA | CNV loss | LOXL4 (9 exons) | NA |
| MAP3K2 | CMX-G0000004205 | CMX-V1566424 | chr2:128093608-128138545 | NA | CNV gain | MAP3K2 (3 exons) | NA |
| MAP3K2 | CMX-G0000004205 | CMX-V1811137 | chr2:128098216-128117112 | NA | CNV gain | MAP3K2 (1 exon) | NA |
| MAP3K2 | CMX-G0000004205 | CMX-V1696049 | chr2:127520276-128116794 | NA | CNV gain | MAP3K2 (16 exons) | NA |
| MUC4 | CMX-G0000006719 | CMX-V9083756 | chr3:195505739 | C | T | Drastic nonsynonymous | NA |
| MUC4 | CMX-G0000006719 | CMX-V9083757 | chr3:195505960 | G | C | Drastic nonsynonymous | NA |
| MUC4 | CMX-G0000006719 | CMX-V90837578 | chr3:195506089 | G | A | Drastic nonsynonymous | NA |
| MUC4 | CMX-G0000006719 | CMX-V9083759 | chr3:195506099 | T | C | Drastic nonsynonymous | NA |
| MUC4 | CMX-G0000006719 | CMX-V9083760 | chr3:195505883 | T | C | Drastic nonsynonymous | NA |
| MUC4 | CMX-G0000006719 | CMX-V9083761 | chr3:195501149 | C | T | Drastic nonsynonymous | NA |
| MUC4 | CMX-G0000006719 | CMX-V9083762 | chr3:195506156 | G | C | Drastic nonsynonymous | NA |
| MUC4 | CMX-G0000006719 | CMX-V9083763 | chr3:195505897 | G | A | Drastic nonsynonymous | NA |
| MUC4 | CMX-G0000006719 | CMX-V9083764 | chr3:195506146 | A | G | Drastic nonsynonymous | NA |
| MUC4 | CMX-G0000006719 | CMX-V9083765 | chr3:195506149 | C | T | Drastic nonsynonymous | NA |
| MUC4 | CMX-G0000006719 | CMX-V9083766 | chr3:195506281 | A | G | Drastic nonsynonymous | NA |
| MUC4 | CMX-G0000006719 | CMX-V9083767 | chr3:195506291 | C | T | Drastic nonsynonymous | NA |
| MUC4 | CMX-G0000006719 | CMX-V9083768 | chr3:195506302 | G | T | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083769 | chr3:195506245 | C | A | Drastic nonsynonymous | NA |
| MUC4 | CMX-G0000006719 | CMX-V9083770 | chr3:195495916 | G | C | Drastic nonsynonymous | NA |
| MUC4 | CMX-G0000006719 | CMX-V9083771 | chr3:195506318 | C | G | Drastic nonsynonymous | NA |
| MUC4 | CMX-G0000006719 | CMX-V9083772 | chr3:195506323 | G | C | Drastic nonsynonymous | NA |
| MUC4 | CMX-G0000006719 | CMX-V9083773 | chr3:195506339 | T | G | Drastic nonsynonymous | NA |
| MUC4 | CMX-G0000006719 | CMX-V9083774 | chr3:195506350 | G | T | Drastic nonsynonymous | NA |
| MUC4 | CMX-G0000006719 | CMX-V9083775 | chr3:195506364 | G | C | Drastic nonsynonymous | NA |
| MUC4 | CMX-G0000006719 | CMX-V9083776 | chr3:195506185 | G | A | Drastic nonsynonymous | NA |
| MUC4 | CMX-G0000006719 | CMX-V9083777 | chr3:195506195 | C | T | Drastic nonsynonymous | NA |
| MUC4 | CMX-G0000006719 | CMX-V9083778 | chr3:195506398 | G | T | Drastic nonsynonymous | NA |
| MUC4 | CMX-G0000006719 | CMX-V9083779 | chr3:195506410 | G | A | Drastic nonsynonymous | NA |
| MUC4 | CMX-G0000006719 | CMX-V9083780 | chr3:195506411 | C | T | Drastic nonsynonymous | NA |
| MUC4 | CMX-G0000006719 | CMX-V9083781 | chr3:195506446 | G | T | Drastic nonsynonymous | NA |
| MUC4 | CMX-G0000006719 | CMX-V9083782 | chr3:195506460 | G | C | Drastic nonsynonymous | NA |
| MUC4 | CMX-G0000006719 | CMX-V9083783 | chr3:195506005 | A | C | Drastic nonsynonymous | NA |
| MUC4 | CMX-G0000006719 | CMX-V9083784 | chr3:195506521 | G | A | Drastic nonsynonymous | NA |
| MUC4 | CMX-G0000006719 | CMX-V9083785 | chr3:195506533 | C | A | Drastic nonsynonymous | NA |
| MUC4 | CMX-G0000006719 | CMX-V9083786 | chr3:195506542 | G | T | Drastic nonsynonymous | NA |
| MUC4 | CMX-G0000006719 | CMX-V9083787 | chr3:195505788 | G | C | Drastic nonsynonymous | NA |
| MUC4 | CMX-G0000006719 | CMX-V9083788 | chr3:195506558 | G | C | Drastic nonsynonymous | NA |
| MUC4 | CMX-G0000006719 | CMX-V9083789 | chr3:195506590 | G | A | Drastic nonsynonymous | NA |
| MUC4 | CMX-G0000006719 | CMX-V9083790 | chr3:195506597 | G | A | Drastic nonsynonymous | NA |
| MUC4 | CMX-G0000006719 | CMX-V9083791 | chr3:195505906 | G | A | Drastic nonsynonymous | NA |
| MUC4 | CMX-G0000006719 | CMX-V9083792 | chr3:195506626 | G | A | Drastic nonsynonymous | NA |
| MUC4 | CMX-G0000006719 | CMX-V9083793 | chr3:195506627 | T | G | Drastic nonsynonymous | NA |
| MUC4 | CMX-G0000006719 | CMX-V9083794 | chr3:195506740 | G | C | Drastic nonsynonymous | NA |
| MUC4 | CMX-G0000006719 | CMX-V9083795 | chr3:195506746 | G | A | Drastic nonsynonymous | NA |
| MUC4 | CMX-G0000006719 | CMX-V9083796 | chr3:195506494 | G | T | Drastic nonsynonymous | NA |
| MUC4 | CMX-G0000006719 | CMX-V9083797 | chr3:195506750 | G | C | Drastic nonsynonymous | NA |
| MUC4 | CMX-G0000006719 | CMX-V9083798 | chr3:195506752 | C | T | Drastic nonsynonymous | NA |
| MUC4 | CMX-G0000006719 | CMX-V9083799 | chr3:195506753 | G | C | Drastic nonsynonymous | NA |
| MUC4 | CMX-G0000006719 | CMX-V9083800 | chr3:195506809 | G | T | Drastic nonsynonymous | NA |
| MUC4 | CMX-G0000006719 | CMX-V9083801 | chr3:195506914 | G | A | Drastic nonsynonym | NA |
| MUC4 | CMX-G0000006719 | CMX-V9083802 | chr3:195506917 | A | C | Drastic nonsynonym | NA |
| MUC4 | CMX-G0000006719 | CMX-V9083803 | chr3:195506933 | G | A | Drastic nonsynonymous | NA |
| MUC4 | CMX-G0000006719 | CMX-V9083804 | chr3:195506940 | G | C | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083805 | chr3:195506953 | G | A | Drastic nonsynonymous | NA |
| MUC4 | CMX-G0000006719 | CMX-V9083806 | chr3:195506965 | T | C | Drastic nonsynonymous | NA |
| MUC4 | CMX-G0000006719 | CMX-V9083807 | chr3:195506966 | C | T | Drastic nonsynonymous | NA |
| MUC4 | CMX-G0000006719 | CMX-V9083808 | chr3:195506975 | G | C | Drastic nonsynonymous | NA |
| MUC4 | CMX-G0000006719 | CMX-V9083809 | chr3:195506747 | C | T | Drastic nonsynonymous | NA |
| MUC4 | CMX-G0000006719 | CMX-V9083810 | chr3:195506986 | G | A | Drastic nonsynonymous | NA |
| MUC4 | CMX-G0000006719 | CMX-V9083811 | chr3:195506987 | T | C | Drastic nonsynonymous | NA |
| MUC4 | CMX-G0000006719 | CMX-V9083812 | chr3:195506990 | C | G | Drastic nonsynonymous | NA |
| MUC4 | CMX-G0000006719 | CMX-V9083813 | chr3:195507010 | A | G | Drastic nonsynonymous | NA |
| MUC4 | CMX-G0000006719 | CMX-V9083814 | chr3:195507059 | T | C | Drastic nonsynonymous | NA |
| MUC4 | CMX-G0000006719 | CMX-V9083815 | chr3:195507062 | C | T | Drastic nonsynonymous | NA |
| MUC4 | CMX-G0000006719 | CMX V9083816 | chr3:195506378 | C | A | Drastic nonsynonymous | NA |
| MUC4 | CMX-G0000006719 | CMX-V9083817 | chr3:195507083 | T | C | Drastic nonsynonymous | NA |
| MUC4 | CMX-G0000006719 | CMX-V9083818 | chr3:195507086 | C | G | Drastic nonsynonymous | NA |
| MUC4 | CMX-G0000006719 | CMX-V9083819 | chr3:195507107 | C | T | Drastic nonsynonymous | NA |
| MUC4 | CMX-G0000006719 | CMX-V9083820 | chr3:195507166 | A | G | Drastic nonsynonymous | NA |
| MUC4 | CMX-G0000006719 | CMX-V9083821 | chr3:195507203 | T | G | Drastic nonsynonymous | NA |
| MUC4 | CMX-G0000006719 | CMX-V9083822 | chr3:195507226 | A | G | Drastic nonsynonymous | NA |
| MUC4 | CMX-G0000006719 | CMX-V9083823 | chr3:195507228 | G | C | Drastic nonsynonymous | NA |
| MUC4 | CMX-G0000006719 | CMX-V9083824 | chr3:195507236 | T | C | Drastic nonsynonymous | NA |
| MUC4 | CMX-G0000006719 | CMX-V9083825 | chr3:195507242 | C | A | Drastic nonsynonymous | NA |
| MUC4 | CMX-G0000006719 | CMX-V9083826 | chr3:195507251 | G | T | Drastic nonsynonymous | NA |
| MUC4 | CMX-G0000006719 | CMX-V9083827 | chr3:195507262 | T | G | Drastic nonsynonymous | NA |
| MUC4 | CMX-G0000006719 | CMX-V9083828 | chr3:195507316 | G | A | Drastic nonsynonymous | NA |
| MUC4 | CMX-G0000006719 | CMX-V9083829 | chr3:195507323 | T | C | Drastic nonsynonymous | NA |
| MUC4 | CMX-G0000006719 | CMX-V9083830 | chr3:195507324 | G | C | Drastic nonsynonymous | NA |
| MUC4 | CMX-G0000006719 | CMX-V9083831 | chr3:195507365 | G | A | Drastic nonsynonymous | NA |
| MUC4 | CMX-G0000006719 | CMX-V9083832 | chr3:195507379 | G | C | Drastic nonsynonymous | NA |
| MUC4 | CMX-G0000006719 | CMX-V9083833 | chr3:195507385 | G | A | Drastic nonsynonymous | NA |
| MUC4 | CMX-G0000006719 | CMX-V9083834 | chr3:195507397 | T | C | Drastic nonsynonymous | NA |
| MUC4 | CMX-G0000006719 | CMX-V9083835 | chr3:195507398 | C | T | Drastic nonsynonymous | NA |
| MUC4 | CMX-G0000006719 | CMX-V9083836 | chr3:195507406 | G | A | Drastic nonsynonymous | NA |
| MUC4 | CMX-G0000006719 | CMX-V9083837 | chr3:195507412 | C | G | Drastic nonsynonymous | NA |
| MUC4 | CMX-G0000006719 | CMX-V9083838 | chr3:195507422 | C | G | Drastic nonsynonymous | NA |
| MUC4 | CMX-G0000006719 | CMX-V9083839 | chr3:195507428 | T | A | Drastic nonsynonymous | NA |
| MUC4 | CMX-G0000006719 | CMX-V9083840 | chr3:195507433 | G | A | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083841 | chr3:195507434 | C | A | Drastic nonsynonymous | NA |
| MUC4 | CMX-G0000006719 | CMX-V9083842 | chr3:195507443 | T | G | Drastic nonsynonymous | NA |
| MUC4 | CMX-G0000006719 | CMX-V9083843 | chr3:195507445 | T | A | Drastic nonsynonymous | NA |
| MUC4 | CMX-G0000006719 | CMX-V9083844 | chr3:195507446 | C | T | Drastic nonsynonymous | NA |
| MUC4 | CMX-G0000006719 | CMX-V9083845 | chr3:195507461 | G | A | Drastic nonsynonymous | NA |
| MUC4 | CMX-G0000006719 | CMX-V9083846 | chr3:195507475 | G | C | Drastic nonsynonymous | NA |
| MUC4 | CMX-G0000006719 | CMX-V9083847 | chr3:195507491 | C | T | Drastic nonsynonymous | NA |
| MUC4 | CMX-G0000006719 | CMX-V9083848 | chr3:195507494 | C | T | Drastic nonsynonymous | NA |
| MUC4 | CMX-G0000006719 | CMX-V9083849 | chr3:195507502 | A | G | Drastic nonsynonymous | NA |
| MUC4 | CMX-G0000006719 | CMX-V9083850 | chr3:195507504 | C | G | Drastic nonsynonymous | NA |
| MUC4 | CMX-G0000006719 | CMX-V9083851 | chr3:195507605 | G | A | Drastic nonsynonymous | NA |
| MUC4 | CMX-G0000006719 | CMX-V9083852 | chr3:195507614 | C | G | Drastic nonsynonymous | NA |
| MUC4 | CMX-G0000006719 | CMX-V9083853 | chr3:195507620 | T | A | Drastic nonsynonymous | NA |
| MUC4 | CMX-G0000006719 | CMX-V9083854 | chr3:195507625 | G | A | Drastic nonsynonymous | NA |
| MUC4 | CMX-G0000006719 | CMX-V9083855 | chr3:195507635 | T | G | Drastic nonsynonymous | NA |
| MUC4 | CMX-G0000006719 | CMX-V9083856 | chr3:195507077 | G | A | Drastic nonsynonymous | NA |
| MUC4 | CMX-G0000006719 | CMX-V9083857 | chr3:195507694 | A | G | Drastic nonsynonymous | NA |
| MUC4 | CMX-G0000006719 | CMX-V9083858 | chr3:195507731 | G | A | Drastic nonsynonymous | NA |
| MUC4 | CMX-G0000006719 | CMX-V9083859 | chr3:195507779 | C | T | Drastic nonsynonymous | NA |
| MUC4 | CMX-G0000006719 | CMX-V9083860 | chr3:195507790 | G | A | Drastic nonsynonymous | NA |
| MUC4 | CMX-G0000006719 | CMX-V9083861 | chr3:195507827 | G | A | Drastic nonsynonymous | NA |
| MUC4 | CMX-G0000006719 | CMX-V9083862 | chr3:195474159 | G | A | Drastic nonsynonymous | NA |
| MUC4 | CMX-G0000006719 | CMX-V9083863 | chr3:195477786 | C | T | Drastic nonsynonymous | NA |
| MUC4 | CMX-G0000006719 | CMX-V9083864 | chr3:195489009 | C | A | Drastic nonsynonymous | NA |
| MUC4 | CMX-G0000006719 | CMX-V9083865 | chr3:195508019 | G | C | Drastic nonsynonymous | NA |
| MUC4 | CMX-G0000006719 | CMX-V9083866 | chr3:195508021 | C | T | Drastic nonsynonymous | NA |
| MUC4 | CMX-G0000006719 | CMX-V9083867 | chr3:195508069 | T | C | Drastic nonsynonymous | NA |
| MUC4 | CMX-G0000006719 | CMX-V9083868 | chr3:195508070 | C | T | Drastic nonsynonymous | NA |
| MUC4 | CMX-G0000006719 | CMX-V9083869 | chr3:195508091 | T | C | Drastic nonsynonymous | NA |
| MUC4 | CMX-G0000006719 | CMX-V9083870 | chr3:195505886 | C | G | Drastic nonsynonymous | NA |
| MUC4 | CMX-G0000006719 | CMX-V9083871 | chr3:195508115 | T | G | Drastic nonsynonymous | NA |
| MUC4 | CMX-G0000006719 | CMX-V9083872 | chr3:195508127 | G | C | Drastic nonsynonymous | NA |
| MUC4 | CMX-G0000006719 | CMX-V9083873 | chr3:195505907 | T | G | Drastic nonsynonymous | NA |
| MUC4 | CMX-G0000006719 | CMX-V9083874 | chr3:195505930 | C | G | Drastic nonsynonymous | NA |
| MUC4 | CMX-G0000006719 | CMX-V9083875 | chr3:195505955 | C | T | Drastic nonsynonymous | NA |
| MUC4 | CMX-G0000006719 | CMX-V9083876 | chr3:195508336 | C | T | Drastic nonsynonymous | NA |

TABLE 7-continued

List of Biologically and Statistically Significant Genetic Variants Most
Useful for Predicting Infertility Risk in Humans (arranged in alphabetical order by
gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083877 | chr3:195505979 | T | C | Drastic nonsynonymous | NA |
| MUC4 | CMX-G0000006719 | CMX-V9083878 | chr3:195508451 | G | T | Drastic nonsynonymous | NA |
| MUC4 | CMX-G0000006719 | CMX-V9083879 | chr3:195508453 | C | T | Drastic nonsynonymous | NA |
| MUC4 | CMX-G0000006719 | CMX-V9083880 | chr3:195508475 | C | T | Drastic nonsynonymous | NA |
| MUC4 | CMX-G0000006719 | CMX-V9083881 | chr3:195508478 | G | C | Drastic nonsynonymous | NA |
| MUC4 | CMX-G0000006719 | CMX-V9083882 | chr3:195508500 | G | C | Drastic nonsynonymous | NA |
| MUC4 | CMX-G0000006719 | CMX-V9083883 | chr3:195508501 | T | C | Drastic nonsynonymous | NA |
| MUC4 | CMX-G0000006719 | CMX-V9083884 | chr3:195508502 | C | T | Drastic nonsynonymous | NA |
| MUC4 | CMX-G0000006719 | CMX-V9083885 | chr3:195508523 | C | T | Drastic nonsynonymous | NA |
| MUC4 | CMX-G0000006719 | CMX-V9083886 | chr3:195508536 | G | C | Drastic nonsynonymous | NA |
| MUC4 | CMX-G0000006719 | CMX-V9083887 | chr3:195508667 | T | C | Drastic nonsynonymous | NA |
| MUC4 | CMX-G0000006719 | CMX-V9083888 | chr3:195508668 | G | C | Drastic nonsynonymous | NA |
| MUC4 | CMX-G0000006719 | CMX-V9083889 | chr3:195508702 | G | A | Drastic nonsynonymous | NA |
| MUC4 | CMX-G0000006719 | CMX-V9083890 | chr3:195506311 | G | C | Drastic nonsynonymous | NA |
| MUC4 | CMX-G0000006719 | CMX-V9083891 | chr3:195506315 | T | C | Drastic nonsynonymous | NA |
| MUC4 | CMX-G0000006719 | CMX-V9083892 | chr3:195508787 | G | T | Drastic nonsynonymous | NA |
| MUC4 | CMX-G0000006719 | CMX-V9083893 | chr3:195508789 | C | T | Drastic nonsynonymous | NA |
| MUC4 | CMX-G0000006719 | CMX-V9083894 | chr3:195509092 | C | T | Drastic nonsynonymous | NA |
| MUC4 | CMX-G0000006719 | CMX-V9083895 | chr3:195509093 | G | A | Drastic nonsynonymous | NA |
| MUC4 | CMX-G0000006719 | CMX-V9083896 | chr3:195509099 | T | C | Drastic nonsynonymous | NA |
| MUC4 | CMX-G0000006719 | CMX-V9083897 | chr3:195509102 | G | C | Drastic nonsynonymous | NA |
| MUC4 | CMX-G0000006719 | CMX-V9083898 | chr3:195506389 | C | T | Drastic nonsynonymous | NA |
| MUC4 | CMX-G0000006719 | CMX-V9083899 | chr3:195509212 | G | A | Drastic nonsynonymous | NA |
| MUC4 | CMX-G0000006719 | CMX-V9083900 | chr3:195509287 | T | G | Drastic nonsynonymous | NA |
| MUC4 | CMX-G0000006719 | CMX-V9083901 | chr3:195509353 | G | A | Drastic nonsynonymous | NA |
| MUC4 | CMX-G0000006719 | CMX-V9083902 | chr3:195509354 | C | T | Drastic nonsynonymous | NA |
| MUC4 | CMX-G0000006719 | CMX-V9083903 | chr3:195509363 | G | T | Drastic nonsynonymous | NA |
| MUC4 | CMX-G0000006719 | CMX-V9083904 | chr3:195509365 | C | T | Drastic nonsynonymous | NA |
| MUC4 | CMX-G0000006719 | CMX-V9083905 | chr3:195509374 | T | G | Drastic nonsynonymous | NA |
| MUC4 | CMX-G0000006719 | CMX-V9083906 | chr3:195509378 | G | C | Drastic nonsynonymous | NA |
| MUC4 | CMX-G0000006719 | CMX-V9083907 | chr3:195509423 | G | A | Drastic nonsynonymous | NA |
| MUC4 | CMX-G0000006719 | CMX-V9083908 | chr3:195506554 | G | A | Drastic nonsynonymous | NA |
| MUC4 | CMX-G0000006719 | CMX-V9083909 | chr3:195509563 | A | T | Drastic nonsynonymous | NA |
| MUC4 | CMX-G0000006719 | CMX-V9083910 | chr3:195509573 | A | G | Drastic nonsynonymous | NA |
| MUC4 | CMX-G0000006719 | CMX-V9083911 | chr3:195509606 | C | T | Drastic nonsynonymous | NA |
| MUC4 | CMX-G0000006719 | CMX-V9083912 | chr3:195506617 | G | A | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083913 | chr3:195509627 | T | C | Drastic nonsynonymous | NA |
| MUC4 | CMX-G0000006719 | CMX-V9083914 | chr3:195509651 | G | A | Drastic nonsynonymous | NA |
| MUC4 | CMX-G0000006719 | CMX-V9083915 | chr3:195509756 | G | C | Drastic nonsynonymous | NA |
| MUC4 | CMX-G0000006719 | CMX-V9083916 | chr3:195509795 | C | T | Drastic nonsynonymous | NA |
| MUC4 | CMX-G0000006719 | CMX-V9083917 | chr3:195509861 | A | G | Drastic nonsynonymous | NA |
| MUC4 | CMX-G0000006719 | CMX-V9083918 | chr3:195509879 | A | G | Drastic nonsynonymous | NA |
| MUC4 | CMX-G0000006719 | CMX-V9083919 | chr3:195509918 | G | C | Drastic nonsynonymous | NA |
| MUC4 | CMX-G0000006719 | CMX-V9083920 | chr3:195509939 | G | T | Drastic nonsynonymous | NA |
| MUC4 | CMX-G0000006719 | CMX-V9083921 | chr3:195509941 | A | C | Drastic nonsynonymous | NA |
| MUC4 | CMX-G0000006719 | CMX-V9083922 | chr3:195509954 | G | C | Drastic nonsynonymous | NA |
| MUC4 | CMX-G0000006719 | CMX-V9083923 | chr3:195509957 | A | G | Drastic nonsynonymous | NA |
| MUC4 | CMX-G0000006719 | CMX-V9083924 | chr3:195509974 | A | G | Drastic nonsynonymous | NA |
| MUC4 | CMX-G0000006719 | CMX-V9083925 | chr3:195510068 | T | A | Drastic nonsynonymous | NA |
| MUC4 | CMX-G0000006719 | CMX-V9083926 | chr3:195510083 | G | T | Drastic nonsynonymous | NA |
| MUC4 | CMX-G0000006719 | CMX-V9083927 | chr3:195510146 | G | C | Drastic nonsynonymous | NA |
| MUC4 | CMX-G0000006719 | CMX-V9083928 | chr3:195510194 | G | C | Drastic nonsynonymous | NA |
| MUC4 | CMX-G0000006719 | CMX-V9083929 | chr3:195510590 | C | G | Drastic nonsynonymous | NA |
| MUC4 | CMX-G0000006719 | CMX-V9083930 | chr3:195506983 | G | A | Drastic nonsynonymous | NA |
| MUC4 | CMX-G0000006719 | CMX-V9083931 | chr3:195510655 | T | G | Drastic nonsynonymous | NA |
| MUC4 | CMX-G0000006719 | CMX-V9083932 | chr3:195510659 | T | C | Drastic nonsynonymous | NA |
| MUC4 | CMX-G0000006719 | CMX-V9083933 | chr3:195510662 | C | T | Drastic nonsynonymous | NA |
| MUC4 | CMX-G0000006719 | CMX-V9083934 | chr3:195510683 | T | C | Drastic nonsynonymous | NA |
| MUC4 | CMX-G0000006719 | CMX-V9083935 | chr3:195510686 | C | G | Drastic nonsynonymous | NA |
| MUC4 | CMX-G0000006719 | CMX-V9083936 | chr3:195510697 | G | A | Drastic nonsynonymous | NA |
| MUC4 | CMX-G0000006719 | CMX-V9083937 | chr3:195510706 | G | A | Drastic nonsynonymous | NA |
| MUC4 | CMX-G0000006719 | CMX-V9083938 | chr3:195510707 | T | G | Drastic nonsynonymous | NA |
| MUC4 | CMX-G0000006719 | CMX-V9083939 | chr3:195510709 | C | T | Drastic nonsynonymous | NA |
| MUC4 | CMX-G0000006719 | CMX-V9083940 | chr3:195510718 | G | T | Drastic nonsynonymous | NA |
| MUC4 | CMX-G0000006719 | CMX-V9083941 | chr3:195510745 | G | A | Drastic nonsynonymous | NA |
| MUC4 | CMX-G0000006719 | CMX-V9083942 | chr3:195510749 | C | A | Drastic nonsynonymous | NA |
| MUC4 | CMX-G0000006719 | CMX V9083943 | chr3:195510766 | G | T | Drastic nonsynonymous | NA |
| MUC4 | CMX-G0000006719 | CMX V9083944 | chr3:195510767 | G | A | Drastic nonsynonymous | NA |
| MUC4 | CMX-G0000006719 | CMX-V9083945 | chr3:195510773 | A | G | Drastic nonsynonymous | NA |
| MUC4 | CMX-G0000006719 | CMX-V9083946 | chr3:195510827 | C | T | Drastic nonsynonymous | NA |
| MUC4 | CMX-G0000006719 | CMX-V9083947 | chr3:195510896 | G | A | Drastic nonsynonymous | NA |
| MUC4 | CMX-G0000006719 | CMX-V9083948 | chr3:195510899 | T | C | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083949 | chr3:195510910 | G | T | Drastic nonsynonymous | NA |
| MUC4 | CMX-G0000006719 | CMX-V9083950 | chr3:195510943 | G | T | Drastic nonsynonymous | NA |
| MUC4 | CMX-G0000006719 | CMX-V9083951 | chr3:195511013 | G | A | Drastic nonsynonymous | NA |
| MUC4 | CMX-G0000006719 | CMX-V9083952 | chr3:195511019 | T | C | Drastic nonsynonymous | NA |
| MUC4 | CMX-G0000006719 | CMX-V9083953 | chr3:195511043 | T | C | Drastic nonsynonymous | NA |
| MUC4 | CMX-G0000006719 | CMX-V9083954 | chr3:195511051 | C | A | Drastic nonsynonymous | NA |
| MUC4 | CMX-G0000006719 | CMX-V9083955 | chr3:195511070 | C | G | Drastic nonsynonymous | NA |
| MUC4 | CMX-G0000006719 | CMX-V9083956 | chr3:195511076 | T | A | Drastic nonsynonymous | NA |
| MUC4 | CMX-G0000006719 | CMX-V9083957 | chr3:195511102 | G | A | Drastic nonsynonymous | NA |
| MUC4 | CMX-G0000006719 | CMX-V9083958 | chr3:195511142 | T | C | Drastic nonsynonymous | NA |
| MUC4 | CMX-G0000006719 | CMX-V9083959 | chr3:195511156 | C | G | Drastic nonsynonymous | NA |
| MUC4 | CMX-G0000006719 | CMX-V9083960 | chr3:195511186 | A | G | Drastic nonsynonymous | NA |
| MUC4 | CMX-G0000006719 | CMX-V9083961 | chr3:195511190 | C | T | Drastic nonsynonymous | NA |
| MUC4 | CMX-G0000006719 | CMX-V9083962 | chr3:195511204 | T | G | Drastic nonsynonymous | NA |
| MUC4 | CMX-G0000006719 | CMX-V9083963 | chr3:195511211 | C | T | Drastic nonsynonymous | NA |
| MUC4 | CMX-G0000006719 | CMX-V9083964 | chr3:195511214 | G | C | Drastic nonsynonymous | NA |
| MUC4 | CMX-G0000006719 | CMX-V9083965 | chr3:195511268 | T | A | Drastic nonsynonymous | NA |
| MUC4 | CMX-G0000006719 | CMX-V9083966 | chr3:195511273 | G | A | Drastic nonsynonymous | NA |
| MUC4 | CMX-G0000006719 | CMX-V9083967 | chr3:195511285 | T | C | Drastic nonsynonymous | NA |
| MUC4 | CMX-G0000006719 | CMX-V9083968 | chr3:195511286 | T | C | Drastic nonsynonymous | NA |
| MUC4 | CMX-G0000006719 | CMX-V9083969 | chr3:195511331 | A | G | Drastic nonsynonymous | NA |
| MUC4 | CMX-G0000006719 | CMX-V9083970 | chr3:195511336 | G | C | Drastic nonsynonymous | NA |
| MUC4 | CMX-G0000006719 | CMX-V9083971 | chr3:195511358 | C | G | Drastic nonsynonymous | NA |
| MUC4 | CMX-G0000006719 | CMX-V9083972 | chr3:195511390 | C | G | Drastic nonsynonymous | NA |
| MUC4 | CMX-G0000006719 | CMX-V9083973 | chr3:195511396 | G | A | Drastic nonsynonymous | NA |
| MUC4 | CMX-G0000006719 | CMX-V9083974 | chr3:195511403 | C | T | Drastic nonsynonymous | NA |
| MUC4 | CMX-G0000006719 | CMX-V9083975 | chr3:195511412 | T | A | Drastic nonsynonymous | NA |
| MUC4 | CMX-G0000006719 | CMX-V9083976 | chr3:195511438 | G | T | Drastic nonsynonymous | NA |
| MUC4 | CMX-G0000006719 | CMX-V9083977 | chr3:195507683 | C | T | Drastic nonsynonymous | NA |
| MUC4 | CMX-G0000006719 | CMX-V9083978 | chr3:195511454 | C | G | Drastic nonsynonymous | NA |
| MUC4 | CMX-G0000006719 | CMX-V9083979 | chr3:195511460 | T | A | Drastic nonsynonymous | NA |
| MUC4 | CMX-G0000006719 | CMX-V9083980 | chr3:195511465 | G | A | Drastic nonsynonymous | NA |
| MUC4 | CMX-G0000006719 | CMX-V9083981 | chr3:195511474 | A | G | Drastic nonsynonymous | NA |
| MUC4 | CMX-G0000006719 | CMX-V9083982 | chr3:195511486 | G | T | Drastic nonsynonymous | NA |
| MUC4 | CMX-G0000006719 | CMX-V9083983 | chr3:195507925 | C | T | Drastic nonsynonymous | NA |
| MUC4 | CMX-G0000006719 | CMX-V9083984 | chr3:195508009 | G | A | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9083985 | chr3:195508010 | C | A | Drastic nonsynonymous | NA |
| MUC4 | CMX-G0000006719 | CMX-V9083986 | chr3:195511513 | G | A | Drastic nonsynonymous | NA |
| MUC4 | CMX-G0000006719 | CMX-V9083987 | chr3:195511525 | T | C | Drastic nonsynonymous | NA |
| MUC4 | CMX-G0000006719 | CMX-V9083988 | chr3:195511526 | C | T | Drastic nonsynonymous | NA |
| MUC4 | CMX-G0000006719 | CMX-V9083989 | chr3:195511534 | T | G | Drastic nonsynonymous | NA |
| MUC4 | CMX-G0000006719 | CMX-V9083990 | chr3:195511547 | C | T | Drastic nonsynonymous | NA |
| MUC4 | CMX-G0000006719 | CMX-V9083991 | chr3:195508108 | G | A | Drastic nonsynonymous | NA |
| MUC4 | CMX-G0000006719 | CMX-V9083992 | chr3:195511690 | G | C | Drastic nonsynonymous | NA |
| MUC4 | CMX-G0000006719 | CMX-V9083993 | chr3:195511705 | G | A | Drastic nonsynonymous | NA |
| MUC4 | CMX-G0000006719 | CMX-V9083994 | chr3:195508175 | G | C | Drastic nonsynonymous | NA |
| MUC4 | CMX-G0000006719 | CMX-V9083995 | chr3:195508178 | G | C | Drastic nonsynonymous | NA |
| MUC4 | CMX-G0000006719 | CMX-V9083996 | chr3:195508238 | C | G | Drastic nonsynonymous | NA |
| MUC4 | CMX-G0000006719 | CMX-V9083997 | chr3:195511822 | G | T | Drastic nonsynonymous | NA |
| MUC4 | CMX-G0000006719 | CMX-V9083998 | chr3:195508402 | G | T | Drastic nonsynonymous | NA |
| MUC4 | CMX-G0000006719 | CMX-V9083999 | chr3:195511870 | G | A | Drastic nonsynonymous | NA |
| MUC4 | CMX-G0000006719 | CMX-V9084000 | chr3:195511877 | G | A | Drastic nonsynonymous | NA |
| MUC4 | CMX-G0000006719 | CMX-V9084001 | chr3:195511918 | G | T | Drastic nonsynonymous | NA |
| MUC4 | CMX-G0000006719 | CMX-V9084002 | chr3:195511925 | A | G | Drastic nonsynonymous | NA |
| MUC4 | CMX-G0000006719 | CMX-V9084003 | chr3:195511937 | C | T | Drastic nonsynonymous | NA |
| MUC4 | CMX-G0000006719 | CMX-V9084004 | chr3:195512042 | T | C | Drastic nonsynonymous | NA |
| MUC4 | CMX-G0000006719 | CMX-V9084005 | chr3:195512107 | T | A | Drastic nonsynonymous | NA |
| MUC4 | CMX-G0000006719 | CMX-V9084006 | chr3:195512117 | C | G | Drastic nonsynonymous | NA |
| MUC4 | CMX-G0000006719 | CMX-V9084007 | chr3:195512195 | C | T | Drastic nonsynonymous | NA |
| MUC4 | CMX-G0000006719 | CMX-V9084008 | chr3:195512206 | A | G | Drastic nonsynonymous | NA |
| MUC4 | CMX-G0000006719 | CMX-V9084009 | chr3:195512212 | G | T | Drastic nonsynonymous | NA |
| MUC4 | CMX-G0000006719 | CMX-V9084010 | chr3:195512242 | G | A | Drastic nonsynonymous | NA |
| MUC4 | CMX-G0000006719 | CMX-V9084011 | chr3:195508774 | G | T | Drastic nonsynonymous | NA |
| MUC4 | CMX-G0000006719 | CMX-V9084012 | chr3:195508786 | A | G | Drastic nonsynonymous | NA |
| MUC4 | CMX-G0000006719 | CMX-V9084013 | chr3:195512267 | T | C | Drastic nonsynonymous | NA |
| MUC4 | CMX-G0000006719 | CMX-V9084014 | chr3:195512270 | C | G | Drastic nonsynonymous | NA |
| MUC4 | CMX-G0000006719 | CMX-V9084015 | chr3:195512287 | G | A | Drastic nonsynonymous | NA |
| MUC4 | CMX-G0000006719 | CMX-V9084016 | chr3:195512302 | G | A | Drastic nonsynonymous | NA |
| MUC4 | CMX-G0000006719 | CMX-V9084017 | chr3:195512567 | G | A | Drastic nonsynonymous | NA |
| MUC4 | CMX-G0000006719 | CMX-V9084018 | chr3:195512597 | G | A | Drastic nonsynonymous | NA |
| MUC4 | CMX-G0000006719 | CMX-V9084019 | chr3:195509170 | A | G | Drastic nonsynonymous | NA |
| MUC4 | CMX-G0000006719 | CMX-V9084020 | chr3:195512606 | G | C | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9084021 | chr3:195512665 | G | A | Drastic nonsynonymous | NA |
| MUC4 | CMX-G0000006719 | CMX-V9084022 | chr3:195512686 | G | T | Drastic nonsynonymous | NA |
| MUC4 | CMX-G0000006719 | CMX-V9084023 | chr3:195512693 | A | G | Drastic nonsynonymous | NA |
| MUC4 | CMX-G0000006719 | CMX-V9084024 | chr3:195512767 | T | G | Drastic nonsynonymous | NA |
| MUC4 | CMX-G0000006719 | CMX-V9084025 | chr3:195512768 | T | A | Drastic nonsynonymous | NA |
| MUC4 | CMX-G0000006719 | CMX-V9084026 | chr3:195513136 | G | C | Drastic nonsynonymous | NA |
| MUC4 | CMX-G0000006719 | CMX-V9084027 | chr3:195513154 | G | T | Drastic nonsynonymous | NA |
| MUC4 | CMX-G0000006719 | CMX-V9084028 | chr3:195513155 | T | C | Drastic nonsynonymous | NA |
| MUC4 | CMX-G0000006719 | CMX-V9084029 | chr3:195509476 | A | G | Drastic nonsynonymous | NA |
| MUC4 | CMX-G0000006719 | CMX-V9084030 | chr3:195513203 | C | T | Drastic nonsynonymous | NA |
| MUC4 | CMX-G0000006719 | CMX-V9084031 | chr3:195513214 | A | G | Drastic nonsynonymous | NA |
| MUC4 | CMX-G0000006719 | CMX-V9084032 | chr3:195513364 | C | T | Drastic nonsynonymous | NA |
| MUC4 | CMX-G0000006719 | CMX-V9084033 | chr3:195509614 | G | A | Drastic nonsynonymous | NA |
| MUC4 | CMX-G0000006719 | CMX-V9084034 | chr3:195513383 | T | A | Drastic nonsynonymous | NA |
| MUC4 | CMX-G0000006719 | CMX-V9084035 | chr3:195513394 | A | T | Drastic nonsynonymous | NA |
| MUC4 | CMX-G0000006719 | CMX-V9084036 | chr3:195513395 | G | T | Drastic nonsynonymous | NA |
| MUC4 | CMX-G0000006719 | CMX-V9084037 | chr3:195513397 | C | T | Drastic nonsynonymous | NA |
| MUC4 | CMX-G0000006719 | CMX-V9084038 | chr3:195513398 | C | T | Drastic nonsynonymous | NA |
| MUC4 | CMX-G0000006719 | CMX-V9084039 | chr3:195513413 | G | A | Drastic nonsynonymous | NA |
| MUC4 | CMX-G0000006719 | CMX-V9084040 | chr3:195513433 | G | A | Drastic nonsynonymous | NA |
| MUC4 | CMX-G0000006719 | CMX-V9084041 | chr3:195513442 | G | T | Drastic nonsynonymous | NA |
| MUC4 | CMX-G0000006719 | CMX-V9084042 | chr3:195513445 | C | T | Drastic nonsynonymous | NA |
| MUC4 | CMX-G0000006719 | CMX-V9084043 | chr3:195513461 | G | A | Drastic nonsynonymous | NA |
| MUC4 | CMX-G0000006719 | CMX-V9084044 | chr3:195513491 | G | T | Drastic nonsynonymous | NA |
| MUC4 | CMX-G0000006719 | CMX-V9084045 | chr3:195513502 | T | G | Drastic nonsynonymous | NA |
| MUC4 | CMX-G0000006719 | CMX-V9084046 | chr3:195513515 | C | T | Drastic nonsynonymous | NA |
| MUC4 | CMX-G0000006719 | CMX-V9084047 | chr3:195513598 | G | A | Drastic nonsynonymous | NA |
| MUC4 | CMX-G0000006719 | CMX-V9084048 | chr3:195513667 | T | G | Drastic nonsynonymous | NA |
| MUC4 | CMX-G0000006719 | CMX-V9084049 | chr3:195513743 | G | T | Drastic nonsynonymous | NA |
| MUC4 | CMX-G0000006719 | CMX-V9084050 | chr3:195513779 | C | T | Drastic nonsynonymous | NA |
| MUC4 | CMX-G0000006719 | CMX-V9084051 | chr3:195510649 | G | A | Drastic nonsynonymous | NA |
| MUC4 | CMX-G0000006719 | CMX-V9084052 | chr3:195513991 | G | A | Drastic nonsynonymous | NA |
| MUC4 | CMX-G0000006719 | CMX-V9084053 | chr3:195514109 | C | A | Drastic nonsynonymous | NA |
| MUC4 | CMX-G0000006719 | CMX-V9084054 | chr3:195514144 | T | C | Drastic nonsynonymous | NA |
| MUC4 | CMX-G0000006719 | CMX-V9084055 | chr3:195514324 | G | A | Drastic nonsynonymous | NA |
| MUC4 | CMX-G0000006719 | CMX-V9084056 | chr3:195514379 | T | C | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9084057 | chr3:195514403 | C | T | Drastic nonsynonymous | NA |
| MUC4 | CMX-G0000006719 | CMX-V9084058 | chr3:195514643 | T | G | Drastic nonsynonymous | NA |
| MUC4 | CMX-G0000006719 | CMX-V9084059 | chr3:195514645 | T | C | Drastic nonsynonymous | NA |
| MUC4 | CMX-G0000006719 | CMX-V9084060 | chr3:195514646 | C | T | Drastic nonsynonymous | NA |
| MUC4 | CMX-G0000006719 | CMX-V9084061 | chr3:195514654 | A | G | Drastic nonsynonymous | NA |
| MUC4 | CMX-G0000006719 | CMX-V9084062 | chr3:195514661 | A | G | Drastic nonsynonymous | NA |
| MUC4 | CMX-G0000006719 | CMX-V9084063 | chr3:195514718 | G | C | Drastic nonsynonymous | NA |
| MUC4 | CMX-G0000006719 | CMX-V9084064 | chr3:195514729 | G | A | Drastic nonsynonymous | NA |
| MUC4 | CMX-G0000006719 | CMX-V9084065 | chr3:195514733 | C | A | Drastic nonsynonymous | NA |
| MUC4 | CMX-G0000006719 | CMX-V9084066 | chr3:195514741 | A | C | Drastic nonsynonymous | NA |
| MUC4 | CMX-G0000006719 | CMX-V9084067 | chr3:195514757 | A | G | Drastic nonsynonymous | NA |
| MUC4 | CMX-G0000006719 | CMX-V9084068 | chr3:195514805 | G | A | Drastic nonsynonymous | NA |
| MUC4 | CMX-G0000006719 | CMX-V9084069 | chr3:195514811 | C | T | Drastic nonsynonymous | NA |
| MUC4 | CMX-G0000006719 | CMX-V9084070 | chr3:195514812 | G | C | Drastic nonsynonymous | NA |
| MUC4 | CMX-G0000006719 | CMX-V9084071 | chr3:195514825 | G | A | Drastic nonsynonymous | NA |
| MUC4 | CMX-G0000006719 | CMX-V9084072 | chr3:195514846 | A | G | Drastic nonsynonymous | NA |
| MUC4 | CMX-G0000006719 | CMX-V9084073 | chr3:195514859 | C | T | Drastic nonsynonymous | NA |
| MUC4 | CMX-G0000006719 | CMX-V9084074 | chr3:195514862 | G | C | Drastic nonsynonymous | NA |
| MUC4 | CMX-G0000006719 | CMX-V9084075 | chr3:195514873 | G | A | Drastic nonsynonymous | NA |
| MUC4 | CMX-G0000006719 | CMX-V9084076 | chr3:195514882 | G | A | Drastic nonsynonymous | NA |
| MUC4 | CMX-G0000006719 | CMX-V9084077 | chr3:195514930 | A | G | Drastic nonsynonymous | NA |
| MUC4 | CMX-G0000006719 | CMX-V9084078 | chr3:195514948 | G | A | Drastic nonsynonymous | NA |
| MUC4 | CMX-G0000006719 | CMX-V9084079 | chr3:195514969 | G | A | Drastic nonsynonymous | NA |
| MUC4 | CMX-G0000006719 | CMX-V9084080 | chr3:195515003 | T | C | Drastic nonsynonymous | NA |
| MUC4 | CMX-G0000006719 | CMX-V9084081 | chr3:195515008 | C | G | Drastic nonsynonymous | NA |
| MUC4 | CMX-G0000006719 | CMX-V9084082 | chr3:195515038 | G | A | Drastic nonsynonymous | NA |
| MUC4 | CMX-G0000006719 | CMX-V9084083 | chr3:195515045 | A | G | Drastic nonsynonymous | NA |
| MUC4 | CMX-G0000006719 | CMX-V9084084 | chr3:195515122 | G | C | Drastic nonsynonymous | NA |
| MUC4 | CMX-G0000006719 | CMX-V9084085 | chr3:195515134 | G | T | Drastic nonsynonymous | NA |
| MUC4 | CMX-G0000006719 | CMX-V9084086 | chr3:195515141 | A | G | Drastic nonsynonymous | NA |
| MUC4 | CMX-G0000006719 | CMX-V9084087 | chr3:195515194 | G | C | Drastic nonsynonymous | NA |
| MUC4 | CMX-G0000006719 | CMX-V9084088 | chr3:195515387 | T | C | Drastic nonsynonymous | NA |
| MUC4 | CMX-G0000006719 | CMX-V9084089 | chr3:195515411 | G | T | Drastic nonsynonymous | NA |
| MUC4 | CMX-G0000006719 | CMX-V9084090 | chr3:195515413 | C | T | Drastic nonsynonymous | NA |
| MUC4 | CMX-G0000006719 | CMX-V9084091 | chr3:195515449 | A | T | Drastic nonsynonymous | NA |
| MUC4 | CMX-G0000006719 | CMX-V9084092 | chr3:195515459 | C | T | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| MUC4 | CMX-G0000006719 | CMX-V9084093 | chr3:195538901 | C | T | Start codon gained | NA |
| MUC4 | CMX-G0000006719 | CMX-V9084094 | chr3:195512246 | T | C | Drastic nonsynonymous | NA |
| MUC4 | CMX-G0000006719 | CMX-V9084095 | chr3:195511556 | T | A | Drastic nonsynonymous | NA |
| MUC4 | CMX-G0000006719 | CMX-V9084096 | chr3:195512603 | T | C | Drastic nonsynonymous | NA |
| MUC4 | CMX-G0000006719 | CMX-V9084097 | chr3:195513173 | G | A | Drastic nonsynonymous | NA |
| MUC4 | CMX-G0000006719 | CMX-V9084098 | chr3:195511451 | T | C | Drastic nonsynonymous | NA |
| MUC4 | CMX-G0000006719 | CMX-V9084099 | chr3:195511781 | G | A | Drastic nonsynonymous | NA |
| MUC4 | CMX-G0000006719 | CMX-V9084100 | chr3:195511499 | C | T | Drastic nonsynonymous | NA |
| MUC4 | CMX-G0000006719 | CMX-V9084101 | chr3:195513365 | G | A | Drastic nonsynonymous | NA |
| MUC4 | CMX-G0000006719 | CMX-V9084102 | chr3:195511780 | G | A | Drastic nonsynonymous | NA |
| MUC4 | CMX-G0000006719 | CMX-V9084103 | chr3:195513826 | G | A | Drastic nonsynonymous | NA |
| MUC4 | CMX-G0000006719 | CMX-V9084104 | chr3:195512245 | T | C | Drastic nonsynonymous | NA |
| MUC4 | CMX-G0000006719 | CMX-V9084105 | chr3:195511500 | G | C | Drastic nonsynonymous | NA |
| MUC4 | CMX G0000006719 | CMX-V9084106 | chr3:195511502 | G | C | Drastic nonsynonymous | NA |
| MUC4 | CMX-G0000006719 | CMX-V9084107 | chr3:195511859 | T | G | Drastic nonsynonymous | NA |
| MUC4 | CMX-G0000006719 | CMX-V9084108 | chr3:195511783 | A | G | Drastic nonsynonymous | NA |
| MUC4 | CMX-G0000006719 | CMX-SV00002 | chr3:195512373 | G | GGAT | Codon change and codon insertion | NA |
| MUC4 | CMX-G0000006719 | CMX-SV00003 | chr3:195518112 | T | TGTCTCCTGCGTAACA | Codon change and codon insertion | NA |
| MUC4 | CMX-G0000006719 | CMX-SV00004 | chr3:195464985 | CNV duplication | NA | Splice acceptor variant | NA |
| MUC4 | CMX-G0000006719 | CMX-SV00005 | chr3:195507809 | CNV deletion | NA | Nonsynonymous and coding sequence | NA |
| MUC4 | CMX-G0000006719 | CMX-SV00006 | chr3:195508499 | CNV duplication | NA | Frameshift | NA |
| MUC4 | CMX-G0000006719 | CMX-V9084187 | chr3:195499847 | A | G | NA | 6.75E−05 |
| MUC4 | CMX-G0000006719 | CMX-V9084188 | chr3:195500367 | A | G | NA | 0.000532509 |
| MUC4 | CMX-G0000006719 | CMX-V9084191 | chr3:195506750 | G | C | NA | 0.000425548 |
| MUC4 | CMX-G0000006719 | CMX-V9084192 | chr3:195506760 | T | A | NA | 7.68E−05 |
| MUC4 | CMX-G0000006719 | CMX-V9084189 | chr3:195506195 | C | T | NA | 8.00E−05 |
| MUC4 | CMX-G0000006719 | CMX-V9084190 | chr3:195506746 | G | A | NA | 0.000150373 |
| NLRP11 | CMX-G0000028188 | CMX-V9084110 | chr19:56323263 | G | A | Drastic nonsynonymous | NA |
| NLRP11 | CMX-G0000028188 | CMX-V9084111 | chr19:56329447 | G | A | Drastic nonsynonymous | NA |
| NLRP11 | CMX-G0000028188 | CMX-V9084112 | chr19:56343378 | C | A | Start codon gained | NA |
| NLRP14 | CMX-G0000016919 | CMX-V9084115 | chr11:7091569 | C | T | Drastic nonsynonymous | NA |
| NLRP14 | CMX-G0000016919 | CMX-V9084116 | chr11:7079038 | G | A | Drastic nonsynonymous | NA |
| NLRP14 | CMX-G0000016919 | CMX-V9084117 | chr11:7059981 | G | A | Drastic nonsynonymous | NA |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| NLRP5 | CMX-G0000028192 | CMX-V9084120 | chr19:56569629 | C | G | Drastic nonsynonymous | NA |
| NLRP5 | CMX-G0000028192 | CMX-V9084121 | chr19:56572875 | G | A | Drastic nonsynonymous | NA |
| NLRP5 | CMX-G0000028192 | CMX-V9084170 | chr19:56567147 | A | G | NA | 8.96E−06 |
| NLRP5 | CMX-G0000028192 | CMX-V9084169 | chr19:56567133 | A | G | NA | 0.000422755 |
| NLRP8 | CMX-G0000028191 | CMX-V9084122 | chr19:56459342 | C | T | Drastic nonsynonymous | NA |
| NLRP8 | CMX-G0000028191 | CMX-V9084123 | chr19:56467375 | C | T | Drastic nonsynonymous | NA |
| NLRP8 | CMX-G0000028191 | CMX-V9084124 | chr19:56499279 | G | C | Stop codon lost | NA |
| PADI3 | CMX-G0000000342 | CMX-V1792728 | chr1:17548826-18037716 | NA | CNV gain | PADI3 (16 exons) | NA |
| PADI6 | CMX-G0000000344 | CMX-V9084147 | chr1:17707931 | T | G | NA | 0.000947202 |
| PADI6 | CMX-G0000000344 | CMX-V9084145 | chr1:17707757 | C | T | NA | 0.000791492 |
| PADI6 | CMX-G0000000344 | CMX-V9084146 | chr1:17707758 | G | C | NA | 0.000832422 |
| PAEP | CMX-G0000015254 | CMX-V1271620 | chr9:138131476-138644038 | NA | CNV gain | PAEP (2 exons) | NA |
| PLCB1 | CMX-G0000028445 | CMX-V1930635 | chr20:8142398-10362561 | NA | CNV gain | PLCB1 (2 exons) | NA |
| PMS2 | CMX-G0000011251 | CMX-V9084128 | chr7:6045627 | C | T | Drastic nonsynonymous | NA |
| PMS2 | CMX-G0000011251 | CMX-SV00007 | chr7:6029313 | CNV duplication | NA | Splice donor, acceptor and coding sequence | NA |
| PMS2 | CMX-G0000011251 | CMX-V9084222 | chr7:5981433 | A | G | NA | 0.000681822 |
| POF1B | CMX-G0000031099 | CMX-V1507096 | chrX:77243971-85734966 | NA | CNV gain | POF1B (15 exons) | NA |
| PRDM9 | CMX-G0000008219 | CMX-V1222200 | chr5:21969693-23940832 | NA | CNV loss | PRDM9 (3 exons) | NA |
| SCARB1 | CMX-G0000019991 | CMX-V9084131 | chr12:125270773 | A | G | Drastic nonsynonymous | NA |
| SCARB1 | CMX-G0000019991 | CMX-V9084132 | chr12:125323962 | A | C | Start codon gained | NA |
| SCARB1 | CMX-G0000019991 | CMX-V9084133 | chr12:125324570 | C | T | Start codon gained | NA |
| SCARB1 | CMX-G0000019991 | CMX-V9084134 | chr12:125324553 | C | T | Start codon gained | NA |
| SERPINA10 | CMX-G0000021629 | CMX-V1143735 | chr14:94691918-278027 | NA | CNV gain | SERPINA10 (4 exons) | NA |
| SIRT3 | CMX-G0000016629 | CMX-V1733950 | chr11:222921-278027 | NA | CNV loss | SIRT3 (2 exons) | NA |
| SPIN1 | CMX-G0000014689 | CMX-V9084227 | chr9:90754700 | G | A | NA | 0.000183378 |
| SPIN1 | CMX-G0000014689 | CMX-V9084228 | chr9:90754733 | A | C | NA | 0.000548473 |
| SPIN1 | CMX-G0000014689 | CMX-V9084229 | chr9:91120108 | G | A | NA | 0.000742923 |
| SPIN1 | CMX-G0000014689 | CMX-V9084230 | chr9:91120393 | A | G | NA | 0.000742923 |
| SPIN1 | CMX-G0000014689 | CMX-V9084231 | chr9:91124743 | A | G | NA | 0.000742923 |
| SPIN1 | CMX-G0000014689 | CMX-V9084232 | chr9:91126304 | C | T | NA | 0.000742923 |
| SPIN1 | CMX-G0000014689 | CMX-V9084233 | chr9:91126736 | G | A | NA | 0.00031089 |
| SPIN1 | CMX-G0000014689 | CMX-V9084234 | chr9:91130846 | G | A |  | 0.000771149 |
| SPIN1 | CMX-G0000014689 | CMX-V9084235 | chr9:91131392 | A | G | NA | 0.000934759 |
| SPIN1 | CMX-G0000014689 | CMX-V9084236 | chr9:91133854 | T | A | NA | 0.000858194 |
| SPIN1 | CMX-G0000014689 | CMX-V9084237 | chr9:91139780 | C | T | NA | 0.000910019 |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| SPIN1 | CMX-G0000014689 | CMX-V9084238 | chr9:91146391 | C | T | NA | 0.000484881 |
| SPN | CMX-G0000023664 | CMX-V1697382 | chr16:29274955-29761984 | NA | CNV loss | SPN (1 exon) | NA |
| TACC3 | CMX-G0000006818 | CMX-V9084137 | chr4:1729556 | G | A | Drastic nonsynonymous | NA |
| TACC3 | CMX-G0000006818 | CMX-V9084138 | chr4:1732978 | G | A | Drastic nonsynonymous | NA |
| TLE6 | CMX-G0000026639 | CMX-V1806717 | chr19:2946999-3051118 | NA | CNV loss | TLE6 (2 exons) | |
| TLE6 | CMX-G0000026639 | CMX-V1336365 | chr19:2937389-3057790 | NA | CNV loss | TLE6 (2 exons) | NA |
| ZP3 | CMX-G0000011947 | CMX-V9084143 | chr7:76058767 | G | T | Start codon gained | NA |
| NA | NA | CMX-V2992389 | chr1:3584692-3585200 | NA | CNV gain | NA | 0.000363085 |
| NA | NA | CMX-V2992390 | chr1:33214881-33216355 | NA | CNV loss | NA | 0.00145087 |
| NA | NA | CMX-V2992391 | chr1:110252792-110252792 | NA | CNV loss | NA | 0.00145087 |
| NA | NA | CMX-V2992392 | chr1:148800056-148802742 | NA | CNV gain | NA | 0.000363942 |
| NA | NA | CMX-V2992393 | chr2:86414923-86421116 | NA | CNV loss | NA | 0.00145087 |
| NA | NA | CMX-V2992394 | chr2:96237124-96237180 | NA | CNV gain | NA | 1.33207E-05 |
| NA | NA | CMX-V2992395 | chr2:215404260-215412550 | NA | CNV loss | NA | 0.000269506 |
| NA | NA | CMX-V2992396 | chr2:217210720-217210773 | NA | CNV loss | NA | 0.00141334 |
| NA | NA | CMX-V2992397 | chr3:38475943-38476013 | NA | CNV loss | NA | 0.000263066 |
| NA | NA | CMX-V2992398 | chr3:150577148-150583696 | NA | CNV loss | NA | 0.00145087 |
| NA | NA | CMX-V2992399 | chr4:95892431-95892748 | NA | CNV loss | NA | 0.000595928 |
| NA | NA | CMX-V2992400 | chr4:103965296-103966620 | NA | CNV gain | NA | 9.32084E-05 |
| NA | NA | CMX-V2992401 | chr4:174691633-174691747 | NA | CNV loss | NA | 0.001024494 |
| NA | NA | CMX-V2992402 | chr5:106349950-106350159 | NA | CNV loss | NA | 0.001666446 |
| NA | NA | CMX-V2992403 | chr5:179654883-179655477 | NA | CNV loss | NA | 0.00091471 |
| NA | NA | CMX-V2992404 | chr6:77073676-77085224 | NA | CNV gain | NA | 0.00010917 |
| NA | NA | CMX-V2992405 | chr7:43968000-44039304 | NA | CNV loss | NA | 0.000860892 |
| NA | NA | CMX-V2992406 | chr7:69794356-69800088 | NA | CNV loss | NA | 0.00145087 |
| NA | NA | CMX-V2992407 | chr7:99464961-99465782 | NA | CNV loss | NA | 0.00125625 |
| NA | NA | CMX-V2992408 | chr7:101713977-101923980 | NA | CNV loss | NA | 0.000860892 |
| NA | NA | CMX-V2992409 | chr8:1229246-101923980 | NA | CNV gain | NA | 0.00116959 |
| NA | NA | CMX-V2992410 | chr8:141723436-141723436 | NA | CNV loss | NA | 0.001419478 |
| NA | NA | CMX-V2992411 | chr8:145465005-145465005 | NA | CNV loss | NA | 0.000488267 |
| NA | NA | CMX-V2992412 | chr9:119213636-119220054 | NA | NA | NA | 0.001446882 |
| NA | NA | CMX-V2992413 | chr9:129199955-129200021 | NA | CNV gain | NA | 0.00046153 |
| NA | NA | CMX-V2992414 | chr9:138557819-138563454 | NA | CNV loss | NA | 0.001446882 |
| NA | NA | CMX-V2992415 | chr10:13425201-13426135 | NA | CNV loss | NA | 0.000295719 |
| NA | NA | CMX-V2992416 | chr10:79352754-79359886 | NA | CNV loss | NA | 0.00145087 |
| NA | NA | CMX-V2992417 | chr10:135037958-135044579 | NA | CNV loss | NA | 0.000983276 |

TABLE 7-continued

List of Biologically and Statistically Significant Genetic Variants Most Useful for Predicting Infertility Risk in Humans (arranged in alphabetical order by gene name)

| Gene Symbol | Celmatix Gene ID | Celmatix Variant ID | Location | Ref | Alt | Impact | P-value |
|---|---|---|---|---|---|---|---|
| NA | NA | CMX-V2992418 | chr11:2113479-2113533 | NA | CNV loss | NA | 0.001566125 |
| NA | NA | CMX-V2992419 | chr11:20521659-20533456 | NA | CNV loss | NA | 0.001445217 |
| NA | NA | CMX-V2992420 | chr11:72165348-72167302 | NA | CNV loss | NA | 0.000366026 |
| NA | NA | CMX-V2992421 | chr12:110336347-110344141 | NA | CNV loss | NA | 0.000263066 |
| NA | NA | CMX-V2992422 | chr12:131580185-131649282 | NA | CNV loss | NA | 0.000434354 |
| NA | NA | CMX-V2992423 | chr13:105982985-105988178 | NA | CNV loss | NA | 0.000434354 |
| NA | NA | CMX-V2992424 | chr14:104711812-104721574 | NA | CNV loss | NA | 0.000117224 |
| NA | NA | CMX-V2992425 | chr14:105554845-105554845 | NA | CNV gain | NA | 0.00115304 |
| NA | NA | CMX-V2992426 | chr14:106038187-106038187 | NA | CNV gain | NA | 0.001388783 |
| NA | NA | CMX-V2992427 | chr15:72473905-72483708 | NA | CNV gain | NA | 2.2682E-05 |
| NA | NA | CMX-V2992428 | chr15:81743011-81748883 | NA | CNV loss | NA | 0.000934763 |
| NA | NA | CMX-V2992429 | chr15:97006211-97006211 | NA | CNV loss | NA | 0.00088514 |
| NA | NA | CMX-V2992430 | chr16:420035-420035 | NA | CNV loss | NA | 0.001033484 |
| NA | NA | CMX-V2992431 | chr16:28297962-28340178 | NA | CNV loss | NA | 3.83769E-05 |
| NA | NA | CMX-V2992432 | chr16:28614007-28653740 | NA | CNV loss | NA | 0.000337601 |
| NA | NA | CMX-V2992433 | chr16:33772936-33809650 | NA | CNV loss | NA | 0.001224595 |
| NA | NA | CMX-V2992434 | chr17:37686892-37687211 | NA | CNV loss | NA | 0.000263066 |
| NA | NA | CMX-V2992435 | chr17:70365673-70365673 | NA | CNV loss | NA | 0.001652185 |
| NA | NA | CMX-V2992436 | chr17:77418789-77465794 | NA | CNV loss | NA | 0.000117224 |
| NA | NA | CMX-V2992437 | chr19:1532671-1549096 | NA | CNV loss | NA | 0.000934076 |
| NA | NA | CMX-V2992438 | chr19:18835562-18835562 | NA | CNV loss | NA | 0.001224595 |
| NA | NA | CMX-V2992439 | chr19:38480199-38480199 | NA | CNV loss | NA | 0.000269506 |
| NA | NA | CMX-V2992440 | chr19:45731785-45732555 | NA | CNV loss | NA | 0.000229579 |
| NA | NA | CMX-V2992441 | chr19:53102000-53153808 | NA | CNV gain | NA | 0.001644428 |
| NA | NA | CMX-V2992442 | chr20:1500411-1508282 | NA | CNV loss | NA | 0.000461106 |
| NA | NA | CMX-V2992443 | chr20:6694925-6696738 | NA | CNV loss | NA | 0.000934763 |
| NA | NA | CMX-V2992444 | chr20:61592202-61594834 | NA | CNV loss | NA | 0.001494022 |
| NA | NA | CMX-V2992445 | chr21:15355967-15355967 | NA | CNV loss | NA | 0.001566125 |
| NA | NA | CMX-V2992446 | chr21:44541166-44547084 | NA | CNV loss | NA | 0.000257622 |
| NA | NA | CMX-V2992447 | chrX:100110102-100110152 | NA | CNV loss | NA | 0.001445217 |
| NA | NA | CMX-V2992448 | chrX:152934795-152944222 | NA | CNV loss | NA | 0.000247877 |

Description of Certain Genes

Below are detailed descriptions of some of the fertility genes described in the tables above.

BARD1

BRCA1-Associated Ring Domain 1 (BARD1) is a gene that forms a heterodimer complex with the BRCA1 gene, and this complex is required for spindle-pole assembly in mitosis, and hence chromosome stability. Mouse embryos carrying homozygous null alleles for BARD1 died between embryonic day 7.5 and embryonic day 8.5 due to severely impaired cell proliferation (McCarthy et al. Molec. Cell. Biol. 23: 5056-5063, 2003).

C6orf221 (KHDC3L)

KH domain containing 3-like, subcortical maternal complex member (KHDC3L). The gene also has the identifier "C6orf221" [Entrez Gene id: 154288, HGNC id: 33699]. KH domains are protein domains that binds to RNA molecules, and KHDC3L is likely involved in genomic imprinting, a phenomenon where genes are expressed in a parental-origin specific manner. KHDC3L gene expression is maximal in germinal vesicle oocytes, tailing off through metaphase II oocytes, and its expression profile is similar to other oocyte-specific genes [Am J Hum Genet. 2011 Sep. 9; 89(3): 451-458]. It is also found within the set of maternal factors that are important for driving egg-to-embryo transition during fertilization [Reproduction. 2010 May; 139(5): 809-23]. Mice carrying homozygous null alleles for KHDC3L display a maternal effect defect in embryogenesis with delayed embryonic development and spindle abnormalities resulting in decreased litter sizes for homozygous females. In humans, KHDC3L has been implicated in familial biparental hydatidiform mole, a maternal-effect recessive inherited disorder [Ref: Am J Hum Genet. 2011 Sep. 9; 89(3): 451-458]

DNMT1

DNA (cytosine-5)-methyltransferase 1 (DNMT1) [Entrez Gene id: 1786, HGNC id: 2976], belongs to a group of enzymes that transfer methyl groups to position 5 of cytosine bases in DNA. While this process, known as DNA methylation, does not alter DNA base composition, it leaves "epigenetic" modifications to DNA molecules that affect the biochemical properties of the DNA region. DNA methylation, mediated by DNMT1, is crucial in determining cell fate during embyogenesis [Genes Dev. 2008 Jun. 15; 22(12): 1607-16, Dev Biol. 2002 Jan. 1; 241(1):172-82.]. Mouse embryos carrying homozygous null alleles for DNMT1 survive only to mid-gestation. The expression of the DNMT1 gene is significantly higher in reproductive tissues than other cell types, and is found within the set of maternal factors that are important for driving egg-to-embryo transition during fertilization [Reproduction. 2010 May; 139(5): 809-23, BMC Genomics. 2009 Aug. 3; 10:348].

FMR1

Fragile X Mental Retardation 1 (FMR1) encodes for the RNA-binding protein FMRP that is implicated in the fragile-X symdrome. The inhibition of translation may be a function of FMR1 in vivo, and that failure of mutant FMR1 protein to oligomerize may contribute to the pathophysiologic events leading to fragile X syndrome. Fragile X premutations in female carriers appear to be a risk factor for premature ovarian failure: 16% of the premutation carriers, menopause occurred before the age of 40, compared with none of the full-mutation carriers and 1 (0.4%) of the controls, indicating a significant association between premature menopause and premutation carrier status. [Am. J. Med. Genet. 83: 322-325, 1999]

FOXO3

Foxhead box O3 (FOXO3) encodes a protein that induces apoptosis in cells, lying within the DNA damage response and repair pathways. FOXO3 knockout female mice exhibit infertility phenotypes, in particular abnormal ovarian follicular function. Mice mutants carrying a homozygous non-synonymous substitution in exon 2 of the FOXO3 gene show loss of fertility of sexual maturity and exhibit premature ovarian failures. [Mammalian Genome 22: 235-248, 2011]

MUC4

MUC4 belongs to a family of high-molecular-weight glycoproteins that protect and lubricate the epithelial surface of respiratory, gastrointestinal and reproductive tracts. The extracellular domain can interact with an epidermal growth factor receptor on the cell surface to modulate downstream cell growth signaling by stabilizing and/or enhancing the activity of cell growth receptor complexes [Nature Rev. Cancer. 4(1):45-60, 2004]. MUC4 is expressed in the endometrial epithelium and is associated with endometriosis development and endometriosis-related infertility such as embryo implantation [BMC Med. 2011 9:19, 2011].

NLRP11

NLR family, pyrin domain containing 11 (NLRP11) encodes a leucine-rich protein belonging to a large family of proteins likely involved in inflammation [Nature Rev. Molec. Cell Biol. 4: 95-104, 2003], and is expressed in the ovary, testes and pre-implantation embryos [BMC Evol Biol. 2009 Aug. 14; 9:202. doi: 10.1186/1471-2148-9-202.]. NLRP11 gene expression shows specificity to reproductive tissues.

NLRP14

NLR family, pyrin domain containing 14 (NLRP14) encodes a leucine-rich protein belonging to a large family of proteins likely involved in inflammation [Nature Rev. Molec. Cell Biol. 4: 95-104, 2003], and is expressed in the ovary, testes and pre-implantation embryos [BMC Evol Biol. 2009 Aug. 14; 9:202. doi: 10.1186/1471-2148-9-202.]. NPRL14 is also found within the set of maternal factors that are important for driving egg-to-embryo transition during fertilization [Reproduction. 2010 May; 139(5):809-23, BMC Genomics. 2009 Aug. 3; 10:348].

NLRP5

NLRP5 or MATER (Maternal antigen the embryos require), the protein encoded by the Nlrp5 gene, is another highly abundant oocyte protein that is essential in mouse for embryonic development beyond the two-cell stage. MATER was originally identified as an oocyte-specific antigen in a mouse model of autoimmune premature ovarian failure (Tong et al., 25 Endocrinology, 140:3720-3726, 1999). MATER demonstrates a similar expression and subcellular expression profile to PADI6. Like Padi6-null animals, Nlrp5-null females exhibit normal oogenesis, ovarian development, oocyte maturation, ovulation and fertilization. However, embryos derived from Nlrp5-null females undergo a developmental block at the two-cell stage and fail to exhibit normal embryonic genome activation (Tong et al., Nat Genet. 26:267-268, 2000; and Tong et al. Mamm Genome 11:281-287, 2000b).

NLRP8

NLR family, pyrin domain containing 8 (NLRP8) encodes a leucine-rich protein belonging to a large family of proteins likely involved in inflammation [Nature Rev. Molec. Cell Biol. 4: 95-104, 2003], and is expressed in the ovary, testes and pre-implantation embryos [*BMC Evol Biol.* 2009 Aug. 14; 9:202. doi: 10.1186/1471-2148-9-202.]. NLRP8 gene expression shows specificity to reproductive tissues.

NPM2

The gene NPM2[Entrez Gene id: 10361, HGNC id: 7930], or nucleoplasmin 2, is a chaperon that binds to histones, and is involved in sperm chromatin remodeling after oocyte entry [Nucleic Acids Res. 2012 June; 40(11): 4861-4878]. NPM2 has been found in a screen for oocyte-specific genes involved in preimplantation embryonic development [Semin Reprod Med. 2007 July; 25(4):243-51], and is differentially expressed during final oocyte maturation and early embryonic development in humans [Feral Steril. 2007 March; 87(3):677-90]. NPM2 is a maternal effect gene critical for nuclear and nucleolar organization and embryonic development, and is found within the set of maternal factors that are important for driving egg-to-embryo transition during fertilization [Reproduction. 2010 May; 139(5): 809-23, BMC Genomics. 2009 Aug. 3; 10:348]. NPM2 is associated with abnormal oocyte morphology and reduced fertility in mice, and female mice homozygous null for NPM2 carry defects in preimplantation embryo development, with abnormalities in oocyte and early embryonic nuclei [Science. 2003 Apr. 25; 300(5619):633-6].

PADI6

Peptidylarginine Deiminase 6 (PADI6)

Padi6 was originally cloned from a 2D murine egg proteome gel based on its relative abundance, and Padi6 expression in mice appears to be almost entirely limited to the oocyte and pre-implantation embryo (Yurttas et al., 2010). Padi6 is first expressed in primordial oocyte follicles and persists, at the protein level, throughout pre-implantation development to the blastocyst stage (Wright et al., Dev Biol, 256:73-88, 2003). Inactivation of Padi6 leads to female infertility in mice, with the Padi6-null developmental arrest occurring at the two-cell stage (Yurttas et al., 2008).

PMS2

PMS2 is involved in DNA mismatch repair and involved in fertilization and pre-implantation development. It has been identified by knockout mouse studies as one of many maternal effect genes essential for development [Nature Cell Bio. 4 Suppl, pp.s 41-9].

SCARB1

Scavenger receptor class B, member 1 (SCARB1) gene encodes a glycoprotein that is a receptor for mediating cholesterol transport. SCARB1-null homozygous female mice were infertile with dysfunctional oocytes [J. Clin. Invest. 108: 1717-1722, 2001], hence, mutations in SCARB1 may affect female fertility by regulating lipoprotein metabolism.

SPIN1

Spindlin 1 (SPIN1) is a gene abundantly expressed in early embryo development, during the transition from oocyte to pluripotent early-embryo. SPIN1 is phosphorylated in a cell-cycle dependent manner and is associated with the meiotic spindle [Development 124: 493-503, 1997].

TACC3

Transforming, Acidic Coiled-Coil Containing Protein 3 (TACC3). In mice, TACC3 is abundantly expressed in the cytoplasm of growing oocytes, and is required for microtubule anchoring at the centrosome and for spindle assembly and cell survival (Fu et al., 2010). TACC3 is also found within the set of maternal factors that are important for driving egg-to-embryo transition during fertilization [Reproduction. 2010 May; 139(5):809-23, BMC Genomics. 2009 Aug. 3; 10:348].

ZP1

Zona pellucid glycoprotein 1 (ZP1) encodes for a protein that is a structural component of the zona pellucida—an extracellular matrix that surrounds the oocyte and early embryo.

ZP2

Zona pellucid glycoprotein 2 (ZP2) encodes for a protein that is a structural component of the zona pellucida—an extracellular matrix that surrounds the oocyte and early embryo. ZP2 binds to acrosome-reacted sperm and is important in preventing polyspermy [*Hum Reprod.* 2004 July; 19(7):1580-6.].

ZP3

Zona pellucid glycoprotein 3 (ZP3) [Entrez Gene id: 7784, HGNC id: 13189], is a structural component of the zona pellucida—an extracellular matrix that surrounds the oocyte and early embryo. It is found within the set of maternal factors that are important for driving egg-to-embryo transition during fertilization [BMC Genomics. 2009 Aug. 3; 10:348]. ZP3 is also expressed in oocytes from early ovarian development, and likely to have a role in the development of primordial follicle before zona pellucida formation [Mol Cell Endocrinol. 2008 Jul. 16; 289(1-2):10-5]. Female mice carring null alleles for ZP3 exhibit decreased ovary size and weight, abnormal ovarian folliculogenesis and ovulation, ultimately resulting in female infertility.

ZP4

Zona pellucid glycoprotein 4 (ZP4) encodes for a protein that is a structural component of the zona pellucida—an extracellular matrix that surrounds the oocyte and early embryo. ZP4 stimulates acrosome reaction as part of a signaling pathway that involves Protein Kinase A [*Biol Reprod.* 2008 November; 79(5):869-77]

DNA (Cytosine-5)-Methyltransferase 1 (DNMT1)

[Entrez Gene id: 1786, HGNC id: 2976], belongs to a group of enzymes that transfer methyl groups to position 5 of cytosine bases in DNA. While this process, known as DNA methylation, does not alter DNA base composition, it leaves "epigenetic" modifications to DNA molecules that affect the biochemical properties of the DNA region. DNA methylation, mediated by DNMT1, is crucial in determining cell fate during embyogenesis [Genes Dev. 2008 Jun. 15; 22(12):1607-16, Dev Biol. 2002 Jan. 1; 241(1):172-82.]. Mouse embryos carrying homozygous null alleles for DNMT1 survive only to mid-gestation. The expression of the DNMT1 gene is significantly higher in reproductive tissues than other cell types, and is found within the set of maternal factors that are important for driving egg-to-embryo transition during fertilization [Reproduction. 2010 May; 139(5):809-23, BMC Genomics. 2009 Aug. 3; 10:348].

The gene NPM2 [Entrez Gene id: 10361, HGNC id: 7930], or nucleoplasmin 2, is a chaperon that binds to histones, and is involved in sperm chromatin remodeling after oocyte entry [Nucleic Acids Res. 2012 June; 40(11): 4861-4878]. NPM2 has been found in a screen for oocyte-specific genes involved in preimplantation embryonic development [Semin Reprod Med. 2007 July; 25(4):243-51], and is differentially expressed during final oocyte maturation and early embryonic development in humans [Feral Steril. 2007 March; 87(3):677-90]. NPM2 is a maternal effect gene critical for nuclear and nucleolar organization and embryonic development, and is found within the set of maternal factors that are important for driving egg-to-embryo transition during fertilization [Reproduction. 2010 May; 139(5): 809-23, BMC Genomics. 2009 Aug. 3; 10:348]. NPM2 is associated with abnormal oocyte morphology and reduced fertility in mice, and female mice homozygous null for NPM2 carry defects in preimplantation embryo development, with abnormalities in oocyte and early embryonic nuclei [Science. 2003 Apr. 25; 300(5619):633-6].

Oocyte-Expressed Protein (OOEP)

[Entrez Gene id: 441161, HGNC id: 21382], also goes by the identifiers KHDC2, FLOPED, HOEP19 and C6orf156. OOEP is found within the set of maternal factors that are important for driving egg-to-embryo transition during fertilization [Reproduction. 2010 May; 139(5):809-23]. OOEP is expressed in ovaries, but not detectable in 11 other cell types including male testes. Within the ovary, its expression is restricted to growing oocytes. The OOEP protein product sublocalizes to the subcortex of eggs and preimplantation embryos. OOEP homozygous null female mice have seemingly normal ovarian physiology and produced viable eggs that can be fertilized, however, these embryos do not progress beyond cleavage stage development and hence these female mice are sterile. It is believed that a functioning OOEP is a pre-requisite for pre-implantation mouse development [Dev Cell. 2008 September; 15(3): 416-425.].

Factor Located in Oocytes Permitting Embryonic Development (FLOPED/OOEP)

The subcortical maternal complex (SCMC) is a poorly characterized murine oocyte structure to which several maternal effect gene products localize (Li et al. Dev Cell 15:416-425, 2008). PADI6, MATER, FILIA, TLE6, and FLOPED have been shown to localize to this complex (Li et al. Dev Cell 15:416-425, 2008; Yurttas et al. Development 135:2627-2636, 2008). This complex is not present in the absence of Floped and Nlrp5, and similar to embryos resulting from Nlrp5-depleted oocytes, embryos resulting from Floped-null oocytes do not progress past the two cell stage of mouse development (Li et al., 2008). FLOPED is a small (19 kD) RNA binding protein that has also been characterized under the name of MOEP19 (Herr et al., Dev Biol 314:300-316, 2008).

Zona Pellucid Glycoprotein 3 (ZP3)

[Entrez Gene id: 7784, HGNC id: 13189], is a structural component of the zona pellucida—an extracellular matrix that surrounds the oocyte and early embryo. It is found within the set of maternal factors that are important for driving egg-to-embryo transition during fertilization [BMC Genomics. 2009 Aug. 3; 10:348]. ZP3 is also expressed in oocytes from early ovarian development, and likely to have a role in the development of primordial follicle before zona pellucida formation [Mol Cell Endocrinol. 2008 Jul. 16; 289(1-2):10-5]. Female mice carring null alleles for ZP3 exhibit decreased ovary size and weight, abnormal ovarian folliculogenesis and ovulation, ultimately resulting in female infertility.

FIGLA (Factor in Germline Alpha)

[Entrez Gene id: 344018, HGNC id:], also goes by the gene identifiers POF6, BHLHC8, and FIGALPHA. This gene is a basic helix-loop-helix transcription factor that acts as an activator of oocyte genes. FIGLA is expressed in all ovarian follicular stages and in mature oocytes, and is required for normal folliculogenesis. FIGLA expression is also believed to repress genes expressed normal in male testes, and hence sustains the female phenotype by activating female and repressing male germ cell genetic hierarchies in growing oocytes during postnatal ovarian development [Mol Cell Biol. 2010 July; 30(14]. Female mice with FIGLA mutations result in decreased oocytes numbers and abnormal ovarian folliculogenesis. Heterozygous mutations in FIGLA has been implicated in women with premature ovarian failure [Am J Hum Genet. 2008 June; 82(6):1342-8.].

Peptidylarginine Deiminase 6 (PADI6)

Padi6 was originally cloned from a 2D murine egg proteome gel based on its relative abundance, and Padi6 expression in mice appears to be almost entirely limited to the oocyte and pre-implantation embryo (Yurttas et al., 2010). Padi6 is first expressed in primordial oocyte follicles and persists, at the protein level, throughout pre-implantation development to the blastocyst stage (Wright et al., Dev Biol, 256:73-88, 2003). Inactivation of Padi6 leads to female infertility in mice, with the Padi6-null developmental arrest occurring at the two-cell stage (Yurttas et al., 2008).

Maternal Antigen the Embryos Require (MATER/NLRP5)

MATER, the protein encoded by the Nlrp5 gene, is another highly abundant oocyte protein that is essential in for embryonic development beyond the two-cell stage. MATER was originally identified as an oocyte-specific antigen in a mouse model of autoimmune premature ovarian failure (Tong et al., Endocrinology, 140:3720-3726, 1999). MATER demonstrates a similar expression and subcellular expression profile to PADI6. Like Padi6-null animals, Nlrp5-null females exhibit normal oogenesis, ovarian development, oocyte maturation, ovulation and fertilization. However, embryos derived from Nlrp5-null females undergo a developmental block at the two-cell stage and fail to exhibit normal embryonic genome activation (Tong et al., Nat Genet. 26:267-268, 2000; and Tong et al. Mamm Genome 11:281-287, 2000b).

KH Domain Containing 3-Like, Subcortical Maternal Complex Member (FILIA/KHDC3L)

FILIA is another small RNA-binding domain containing maternally inherited murine protein. FILIA was identified and named for its interaction with MATER (Ohsugi et al. Development 135:259-269, 2008). Like other components of the SCMC, maternal inheritance of the Khdc3 gene product is required for early embryonic development. In mice, loss of Khdc3 results in a developmental arrest of varying severity with a high incidence of aneuploidy due, in part, to improper chromosome alignment during early cleavage divisions (Li et al., 2008). Khdc3 depletion also results in aneuploidy, due to spindle checkpoint assembly (SAC) inactivation, abnormal spindle assembly, and chromosome misalignment (Zheng et al. Proc Natl Acad Sci USA 106: 7473-7478, 2009).

Basonuclin (BNC1)

Basonuclin is a zinc finger transcription factor that has been studied in mice. It is found expressed in keratinocytes and germ cells (male and female) and regulates rRNA (via polymerase I) and mRNA (via polymerase II) synthesis (Iuchi and Green, 1999; Wang et al., 2006). Depending on the amount by which expression is reduced in oocytes, embryos may not develop beyond the 8-cell stage. In Bsn1 depleted mice, a normal number of oocytes are ovulated even though oocyte development is perturbed, but many of these oocytes cannot go on to yield viable offspring (Ma et al., 2006).

Zygote Arrest 1 (ZAR1) Zar1 is an oocyte-specific maternal effect gene that is known to function at the oocyte to embryo transition in mice. High levels of Zar1 expression are observed in the cytoplasm of murine oocytes, and homozygous-null females are infertile: growing oocytes from Zar1-null females do not progress past the two-cell stage.

Cytosolic Phospholipase A2γ(PLA2G4C)

Under normal conditions, cPLA2γ, the protein product of the murine PLA2G4C ortholog, expression is restricted to oocytes and early embryos in mice. At the subcellular level, cPLA2γ mainly localizes to the cortical regions, nucleoplasm, and multivesicular aggregates of oocytes. It is also worth noting that while cPLA2γ expression does appear to be mainly limited to oocytes and pre-implantation embryos in healthy mice, expression is considerably up-regulated within the intestinal epithelium of mice infected with *Trichinella spiralis*. This suggests that cPLA2γ may also play a role in the inflammatory response. The human PLA2G4C differs in that rather than being abundantly expressed in the ovary, it is abundantly expressed in the heart and skeletal muscle. Also, the human protein contains a lipase consensus sequence but lacks a calcium-binding domain found in other PLA2 enzymes. Accordingly, another cytosolic phospholipase may be more relevant for human fertility.

Transforming, Acidic Coiled-Coil Containing Protein 3 (TACC3)

In mice, TACC3 is abundantly expressed in the cytoplasm of growing oocytes, and is required for microtubule anchoring at the centrosome and for spindle assembly and cell survival (Fu et al., 2010). In certain embodiments, the gene is a gene that is expressed in an oocyte. Exemplary genes include CTCF, ZFP57, POU5F1, SEBOX, and HDAC1.

In other embodiments, the gene is a gene that is involved in DNA repair pathways, including but not limited to, MLH1, PMS1 and PMS2. In other embodiments, the gene is BRCA1 or BRCA2.

In other embodiments, the biomarker is a gene product (e.g., RNA or protein) of an infertility-associated gene. In particular embodiments, the gene product is a gene product of a maternal effect gene. In other embodiments, the gene product is a product of a gene from Table 1. In certain embodiments, the gene product is a product of a gene that is expressed in an oocyte, such as a product of CTCF, ZFP57, POU5F1, SEBOX, and HDAC1. In other embodiments, the gene product is a product of a gene that is involved in DNA repair pathways, such as a product of MLH1, PMS1, or PMS2. In other embodiments, gene product is a product of BRCA1 or BRCA2.

In other embodiments, the biomarker may be an epigenetic factor, such as methylation patterns (e.g., hypermethylation of CpG islands), genomic localization or post-translational modification of histone proteins, or general post-translational modification of proteins such as acetylation, ubiquitination, phosphorylation, or others.

In other embodiments, methods of the invention analyze infertility-associated biomarkers in order to assess the risk infertility.

In certain embodiments, the biomarker is a genetic region, gene, or RNA/protein product of a gene associated with the one carbon metabolism pathway and other pathways that effect methylation of cellular macromolecules. Exemplary genes and products of those genes are described below.

Methylenetetrahydrofolate Reductase (MTHFR)

In particular embodiments a mutation (677C>T) in the MTHFR gene is associated with infertility. The enzyme 5,10-methylenetetrahydrofolate reductase regulates folate activity (Pavlik et al., Fertility and Sterility 95(7): 2257-2262, 2011). The 677TT genotype is known in the art to be associated with 60% reduced enzyme activity, inefficient folate metabolism, decreased blood folate, elevated plasma homocysteine levels, and reduced methylation capacity. Pavlik et al. (2011) investigated the effect of the MTHFR 677C>T on serum anti-Mullerian hormone (AMH) concentrations and on the numbers of oocytes retrieved (NOR) following controlled ovarian hyperstimulation (COH). Two hundred and seventy women undergoing COH for IVF were analyzed, and their AMH levels were determined from blood samples collected after 10 days of GnRH superagonist treatment and before COH. Average AMH levels of TT carriers were significantly higher than those of homozygous CC or heterozygous CT individuals. AMH serum concentrations correlated significantly with the NOR in all individuals studied. The study concluded that the MTHFR 677TT genotype is associated with higher serum AMH concentrations but paradoxically has a negative effect on NOR after COH. It was proposed that follicle maturation might be retarded in MTHFR 677TT individuals, which could subsequently lead to a higher proportion of initially recruited follicles that produce AMH, but fail to progress towards cyclic recruitment. The tissue gene expression patterns of MTHFR do not show any bias towards oocyte expression. Analyzing a sample for this mutation or other mutations (Table 1) in the MTHFR gene or abnormal gene expression of products of the MTHFR gene allows one to assess a risk of infertility.

Jeddi-Tehrani et al. (American Journal of Reproductive Immunology 66(2):149-156, 2011) investigated the effect of the MTHFR 677TT genotype on Recurrant Pregnancy Loss (RPL). One hundred women below 35 years of age with two successive pregnancy losses and one hundred healthy women with at least two normal pregnancies were used to assess the frequency of five candidate genetic risk factors for RPL-MTHFR 677C>T, MTHFR 1298A>C, PARI1-675 4G/5G (Plasminogen Activator Inhibitor-1 promoter region), BF-455G/A (Beta Fibrinogen promoter region), and ITGB3 1565T/C (Integrin Beta 3). The frequencies of the polymorphisms were calculated and compared between case and control groups. Both the MTHFR polymorphisms (677C>T and 1298 A>C) and the BF-455G/A polymorphism were found to be positively and ITGB3 1565T/C polymorphism was found to be negatively associated with RPL. Homozygosity but not heterozygosity for the PAI-1-6754G/5G polymorphism was significantly higher in patients with RPL than in the control group. The presence of both mutations of MTHFR genes highly increased the risk of RPL. Analyzing a sample for these mutation and other mutations (Table 1) in the MTHFR gene or abnormal gene expression of products of the MTHFR gene allows one to assess a risk of infertility.

Catechol-O-Methyltransferase (COMT)

In particular embodiments a mutation (472G>A) in the COMT gene is associated with infertility. Catechol-O-methyltransferase is known in the art to be one of several enzymes that inactivates catecholamine neurotransmitters by transferring a methyl group from SAM (S-adenosyl methionine) to the catecholamine. The AA gene variant is known to alter the enzyme's thermostability and reduces its activity 3 to 4 fold (Schmidt et al., Epidemiology 22(4): 476-485, 2011). Salih et al. (Fertility and Sterility 89(5, Supplement 1): 1414-1421, 2008) investigated the regulation of COMT expression in granulosa cells and assessed the effects of 2-ME2 (COMT product) and COMT inhibitors on DNA proliferation and steroidogenesis in JC410 porcine and HGLS human granulosa cell lines in in vitro experiments. They further assessed the regulation of COMT expression by DHT (Dihydrotestosterone), insulin, and ATRA (all-trans retinoic acid). They concluded that COMT expression in granulosa cells was up-regulated by insulin, DHT, and ATRA. Further, 2-ME2 decreased, and COMT inhibition increased granulosa cell proliferation and steroidogenesis. It was hypothesized that COMT overexpression with subsequent increased level of 2-ME2 may lead to ovulatory dysfunction. Analyzing a sample for this mutation in the COMT gene or abnormal gene expression of products of the COMT gene allows one to assess a risk of infertility.

Methionine Synthase Reductase (MTRR)

In particular embodiments a mutation (A66G) in the Methionine Synthase Reductase (MTRR) gene is associated with infertility. MTRR is required for the proper function of the enzyme Methionine Synthase (MTR). MTR converts homocysteine to methionine, and MTRR activates MTR, thereby regulating levels of homocysteine and methionine. The maternal variant A66G has been associated with early developmental disorders such as Down's syndrome (Pozzi et al., 2009) and Spina Bifida (Doolin et al., American journal of human genetics 71(5): 1222-1226, 2002). Analyzing a sample for this mutation in the MTRR gene or abnormal gene expression of products of the MTRR gene allows one to assess the risk of infertility.

Betaine-Homocysteine S-Methyltransferase (BHMT)

In particular embodiments a mutation (G716A) in the BHMT gene is associated with infertility. Betaine-Homocysteine S-Methyltransferase (BHMT), along with MTRR, assists in the Folate/B-12 dependent and choline/betaine-dependent conversions of homocysteine to methionine. High homocysteine levels have been linked to female infertility (Berker et al., Human Reproduction 24(9): 2293-2302, 2009). Benkhalifa et al. (2010) discuss that controlled ovarian hyperstimulation (COH) affects homocysteine concentration in follicular fluid. Using germinal vescicle oocytes from patients involved in IVF procedures, the study concludes that the human oocyte is able to regulate its homocysteine level via remethylation using MTR and BHMT, but not CBS (Cystathione Beta Synthase). They further emphasize that this may regulate the risk of imprinting problems during IVF procedures. Analyzing a sample for this mutation in the BHMT gene or abnormal gene expression of products of the BHMT gene allows one to assess a risk of infertility.

Ikeda et al. (Journal of Experimental Zoology Part A: Ecological Genetics and Physiology 313A(3): 129-136, 2010) examined the expression patterns of all methylation pathway enzymes in bovine oocytes and preimplantation embryos. Bovine oocytes were demonstrated to have the mRNA of MAT1A (Methionine adenosyltransferase), MAT2A, MAT2B, AHCY (S-adenosylhomocysteine hydrolase), MTR, BHMT, SHMT1 (Serine hydroxymethyltransferase), SHMT2, and MTHFR. All these transcripts were consistently expressed through all the developmental stages, except MAT1A, which was not detected from the 8-cell stage onward, and BHMT, which was not detected in the 8-cell stage. Furthermore, the effect of exogenous homocysteine on preimplantation development of bovine embryos was investigated in vitro. High concentrations of homocysteine induced hypermethylation of genomic DNA as well as developmental retardation in bovine embryos. Analyzing a sample for these irregular methylation patterns allows one to assess a risk of infertility.

Folate Receptor 2 (FOLR2)

In particular embodiments a mutation (rs2298444) in the FOLR2 gene is associated with infertility. Folate Receptor 2 helps transport folate (and folate derivatives) into cells. Elnakat and Ratnam (Frontiers in bioscience: a journal and virtual library 11: 506-519, 2006) implicate FOLR2, along with FOLR1, in ovarian and endometrial cancers. Analyzing sample mutations in the FOLR2 or FOLR1 genes or abnormal gene expression of products of the FOLR2 or FOLR1 genes allows one to assess a risk of infertility.

Transcobalamin 2 (TCN2)

In particular embodiments a mutation (C776G) in the TCN2 gene is associated with infertility. Transcobalamin 2 facilitates transport of cobalamin (Vitamin B12) into cells. Stanislawska-Sachadyn et al. (Eur J ClinNutr 64(11): 1338-1343, 2010) assessed the relationship between TCN2 776C>G polymorphism and both serum B12 and total homocysteine (tHcy) levels. Genotypes from 613 men from Northern Ireland were used to show that the TCN2 776CC genotype was associated with lower serum B12 concentrations when compared to the 776CG and 776GG genotypes. Furthermore, vitamin B12 status was shown to influence the relationship between TCN2 776C>G genotype and tHcy concentrations. The TCN2 776C>G polymorphism may contribute to the risk of pathologies associated with low B12 and high total homocysteine phenotype. Analyzing a sample for this mutation in the TCN2 gene or abnormal gene expression of products of the TCN2 gene allows one to assess a risk of infertility.

Cystathionine-Beta-Synthase (CBS)

In particular embodiments a mutation (rs234715) in the CBS gene is associated with infertility. With vitamin B6 as a cofactor, the Cystathionine-Beta-Synthase (CBS) enzyme catalyzes a reaction that permanently removes homocysteine from the methionine pathway by diverting it to the transsulfuration pathway. CBS gene mutations associated with decreased CBS activity also lead to elevated plasma homocysteine levels. Guzman et al. (2006) demonstrate that Cbs knockout mice are infertile. They further explain that Cbs-null female infertility is a consequence of uterine failure, which is a consequence of hyperhomocysteinemia or other factor(s) in the uterine environment. Analyzing a sample for this mutation in the CBS gene or abnormal gene expression of products of the CBS gene allows one to assess a risk of infertility.

In certain embodiments, the biomarker is a genetic region that has been previously associated with female infertility. A SNP association study by targeted re-sequencing was performed to search for new genetic variants associated with female infertility. Such methods have been successful in identifying significant variants associated in a wide range of diseases Rehman et al., 2010; Walsh et al., 2010). Briefly, a SNP association study is performed by collecting SNPs in genetic regions of interest in a number of samples and controls and then testing each of the SNPs that showed significant frequency differences between cases and controls. Significant frequency differences between cases and controls indicate that the SNP is associated with the condition of interest.

Assays

Methods of the invention involve conducting an assay that detects either a mutation in an infertility-associated gene or abnormal expression (over or under) of an infertility-associated gene product. In particular embodiments, the assay is conducted on infertility-associated genetic regions or products of these regions. Detailed descriptions of conventional methods, such as those employed to make and use nucleic acid arrays, amplification primers, hybridization probes, and the like can be found in standard laboratory manuals such as: Genome Analysis: A Laboratory Manual Series (Vols. I-IV), Cold Spring Harbor Laboratory Press; PCR Primer: A Laboratory Manual, Cold Spring Harbor Laboratory Press; and Sambrook, J et al., (2001) Molecular Cloning: A Laboratory Manual, 2nd ed. (Vols.

1-3), Cold Spring Harbor Laboratory Press. Custom nucleic acid arrays are commercially available from, e.g., Affymetrix (Santa Clara, Calif.), Applied Biosystems (Foster City, Calif.), and Agilent Technologies (Santa Clara, Calif.).

Methods of detecting mutations in genetic regions are known in the art. In certain embodiments, a mutation in a single infertility-associated genetic region indicates infertility. In other embodiments, the assay is conducted on more than one genetic region, and a mutation in at least two of the genetic regions indicates infertility. In other embodiments, a mutation in at least three of the genetic regions indicates infertility; a mutation in at least four of the genetic regions indicates infertility; a mutation in at least five of the genetic regions indicates infertility; a mutation in at least six of the genetic regions indicates infertility; a mutation in at least seven of the genetic regions indicates infertility; a mutation in at least eight of the genetic regions indicates infertility; a mutation in at least nine of the genetic regions indicates infertility; a mutation in at least 10 of the genetic regions indicates infertility; a mutation in at least 15 of the genetic regions indicates infertility; or a mutation in all of the genetic regions from Table 1 indicates infertility.

In certain embodiments, a known single nucleotide polymorphism at a particular position can be detected by single base extension for a primer that binds to the sample DNA adjacent to that position. See for example Shuber et al. (U.S. Pat. No. 6,566,101), the content of which is incorporated by reference herein in its entirety. In other embodiments, a hybridization probe might be employed that overlaps the SNP of interest and selectively hybridizes to sample nucleic acids containing a particular nucleotide at that position. See for example Shuber et al. (U.S. Pat. Nos. 6,214,558 and 6,300,077), the content of which is incorporated by reference herein in its entirety.

In particular embodiments, nucleic acids are sequenced in order to detect variants (i.e., mutations) in the nucleic acid compared to wild-type and/or non-mutated forms of the sequence. The nucleic acid can include a plurality of nucleic acids derived from a plurality of genetic elements. Methods of detecting sequence variants are known in the art, and sequence variants can be detected by any sequencing method known in the art e.g., ensemble sequencing or single molecule sequencing.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977). Another conventional sequencing method involves chemical degradation of nucleic acid fragments. See, Maxam et al., Proc. Natl. Acad. Sci., 74: 560 564 (1977). Methods have also been developed based upon sequencing by hybridization. See, e.g., Harris et al., (U.S. patent application number 2009/0156412). The content of each reference is incorporated by reference herein in its entirety.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53:1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

If the nucleic acid from the sample is degraded or only a minimal amount of nucleic acid can be obtained from the sample, PCR can be performed on the nucleic acid in order to obtain a sufficient amount of nucleic acid for sequencing (See e.g., Mullis et al. U.S. Pat. No. 4,683,195, the contents of which are incorporated by reference herein in its entirety).

Methods of detecting levels of gene products (e.g., RNA or protein) are known in the art. Commonly used methods known in the art for the quantification of mRNA expression in a sample include northern blotting and in situ hybridization (Parker & Barnes, Methods in Molecular Biology 106:247 283 (1999), the contents of which are incorporated by reference herein in their entirety); RNAse protection assays (Hod, Biotechniques 13:852 854 (1992), the contents of which are incorporated by reference herein in their entirety); and PCR-based methods, such as reverse transcription polymerase chain reaction (RT-PCR) (Weis et al., Trends in Genetics 8:263 264 (1992), the contents of which are incorporated by reference herein in their entirety). Alternatively, antibodies may be employed that can recognize specific duplexes, including RNA duplexes, DNA-RNA hybrid duplexes, or DNA-protein duplexes. Other methods known in the art for measuring gene expression (e.g., RNA or protein amounts) are shown in Yeatman et al. (U.S. patent application number 2006/0195269), the content of which is hereby incorporated by reference in its entirety.

A differentially expressed gene or differential gene expression refer to a gene whose expression is activated to a higher or lower level in a subject suffering from a disorder, such as infertility, relative to its expression in a normal or control subject. The terms also include genes whose expression is activated to a higher or lower level at different stages of the same disorder. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example.

Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disorder, such as infertility, or between various stages of the same disorder. Differential expression includes both quantitative, as well as qualitative, differences in the temporal or cellular expression pattern in a gene or its expression products. Differential gene expression (increases and decreases in expression) is based upon percent or fold changes over expression in normal cells. Increases may be of 1, 5, 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or 10 fold over expression levels in normal cells. Decreases may be of 1, 5, 10, 20, 30, 40, 50, 55, 60, 65, 70, 75, 80, 82, 84, 86, 88, 90, 92, 94, 96, 98, 99 or 100% relative to expression levels in normal cells.

In certain embodiments, reverse transcriptase PCR (RT-PCR) is used to measure gene expression. RT-PCR is a quantitative method that can be used to compare mRNA levels in different sample populations to characterize patterns of gene expression, to discriminate between closely related mRNAs, and to analyze RNA structure.

The first step is the isolation of mRNA from a target sample. The starting material is typically total RNA isolated from human tissues or fluids.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). The contents of each of theses references is incorporated by reference herein in their entirety. In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MAS-TERPURE Complete DNA and RNA Purification Kit (EPICENTRE, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700 Sequence Detection System™ (Perkin-Elmer-Applied Biosystems, Foster City, Calif., USA), or Lightcycler (Roche Molecular Biochemicals, Mannheim, Germany). In certain embodiments, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin. For performing analysis on pre-implantation embryos and oocytes, Chuk is a gene that is used for normalization.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, in which internal competitor for each target sequence is used for normalization, and with quantitative comparative PCR using a normalization gene contained within the sample, or a housekeeping gene for RT-PCR. For further details see, e.g. Held et al., Genome Research 6:986 994 (1996), the contents of which are incorporated by reference herein in their entirety.

In another embodiment, a MassARRAY-based gene expression profiling method is used to measure gene expression. In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059 3064 (2003).

Further PCR-based techniques include, for example, differential display (Liang and Pardee, Science 257:967 971 (1992)); amplified fragment length polymorphism (iAFLP) (Kawamoto et al., Genome Res. 12:1305 1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888 1898 (2001)); and high coverage expression profiling (HiCEP) analysis (Fukumura et al., Nucl. Acids. Res. 31(16) e94 (2003)). The contents of each of which are incorporated by reference herein in their entirety.

In certain embodiments, differential gene expression can also be identified, or confirmed using a microarray technique. In this method, polynucleotide sequences of interest (including cDNAs and oligonucleotides) are plated, or arrayed, on a microchip substrate. The arrayed sequences are then hybridized with specific DNA probes from cells or tissues of interest. Methods for making microarrays and determining gene product expression (e.g., RNA or protein) are shown in Yeatman et al. (U.S. patent application number 2006/0195269), the content of which is incorporated by reference herein in its entirety.

In a specific embodiment of the microarray technique, PCR amplified inserts of cDNA clones are applied to a substrate in a dense array, for example, at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106 149 (1996), the contents of which are incorporated by reference herein in their entirety). Microarray analysis can be performed by commercially available equipment, following manufacturer's protocols, such as by using the Affymetrix GenChip technology, or Incyte's microarray technology.

Alternatively, protein levels can be determined by constructing an antibody microarray in which binding sites comprise immobilized, preferably monoclonal, antibodies specific to a plurality of protein species encoded by the cell genome. Preferably, antibodies are present for a substantial fraction of the proteins of interest. Methods for making monoclonal antibodies are well known (see, e.g., Harlow and Lane, 1988, ANTIBODIES: A LABORATORY MANUAL, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art. Generally, the expression, and the level of expression, of proteins of diagnostic or prognostic interest can be detected through immunohistochemical staining of tissue slices or sections.

Finally, levels of transcripts of marker genes in a number of tissue specimens may be characterized using a "tissue array" (Kononen et al., Nat. Med. 4(7):844-7 (1998)). In a tissue array, multiple tissue samples are assessed on the same microarray. The arrays allow in situ detection of RNA and protein levels; consecutive sections allow the analysis of multiple samples simultaneously.

In other embodiments, Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997, the contents of each of which are incorporated by reference herein in their entirety).

In other embodiments Massively Parallel Signature Sequencing (MPSS) is used to measure gene expression. This method, described by Brenner et al., Nature Biotechnology 18:630 634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Immunohistochemistry methods are also suitable for detecting the expression levels of the gene products of the present invention. Thus, antibodies (monoclonal or polyclonal) or antisera, such as polyclonal antisera, specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

In certain embodiments, a proteomics approach is used to measure gene expression. A proteome refers to the totality of the proteins present in a sample (e.g. tissue, organism, or cell culture) at a certain point of time. Proteomics includes, among other things, study of the global changes of protein expression in a sample (also referred to as expression proteomics). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

In some embodiments, mass spectrometry (MS) analysis can be used alone or in combination with other methods (e.g., immunoassays or RNA measuring assays) to determine the presence and/or quantity of the one or more biomarkers disclosed herein in a biological sample. In some embodiments, the MS analysis includes matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated by reference herein in their entirety.

Phenotypic Traits

In certain embodiments, methods of the invention assess risk of female infertility by correlating assay results with an analysis of a phenotypic trait or environmental exposure that may be associated with infertility. Exemplary phenotypic traits or environmental exposures are shown in Table 8.

TABLE 8

Phenotypic and environmental variables impacting fertility success

Cholesterol levels on different days of the menstrual cycle
Age of first menses for patient and female blood relatives (e.g. sisters, mother, grandmothers)
Age of menopause for female blood relatives (e.g. sisters, mother, grandmothers)
Number of previous pregnancies (biochemical/ectopic/clinical/fetal heart beat detected, live birth outcomes), age at the time, and outcome for patient and female blood relatives (e.g. sisters, mother, grandmothers)
Diagnosis of Polycystic Ovarian Syndrome
History of hydrosalpinx or tubal occlusion
History of endometriosis, pelvic pain, or painful periods
Cancer history/type of cancer/treatment/outcome for patient and female blood relatives (e.g. sisters, mother, grandmothers)
Age that sexual activity began, current level of sexual activity
Smoking history for patient and blood relatives
Travel schedule/number of flying hours a year/time difference changes of more than 3 hours
(Jetlag and Flight-associated Radiation Exposure)
Nature of periods (length of menses, length of cycle)
Biological age (number of years since first menses)
Birth control use
Drug use (illegal or legal)
Body mass index (current, lowest ever, highest ever)
History of polyps
History of hormonal imbalance
History of amenorrhoea
History of eating disorders
Alcohol consumption by patient or blood relatives
Details of mother's pregnancy with patient (i.e. measures of uterine environment): any drugs taken, smoking, alcohol, stress levels, exposure to plastics (i.e. Tupperware), composition of diet (see below)
Sleep patterns: number of hours a night, continuous/overall
Diet: meat, organic produce, vegetables, vitamin or other supplement consumption, dairy (full fat or reduced fat), coffee/tea consumption, folic acid, sugar(complex, artificial, simple), processed food versus home cooked.
Exposure to plastics: microwave in plastic, cook with plastic, store food in plastic, plastic water or coffee mugs.
Water consumption: amount per day, format: straight from the tap, bottled water (plastic or bottle), filtered (type: e.g. Britta/Pur)
Residence history starting with mother's pregnancy: location/duration
Environmental exposure to potential toxins for different regions (extracted from government monitoring databases)
Health metrics: autoimmune disease, chronic illness/condition
Pelvic surgery history
Life time number of pelvic X-rays
History of sexually transmitted infections: type/treatment/outcome
Reproductive hormone levels: follicle stimulating hormone, anti-Miillerian hormone, estrogen, progesterone TABLE 8-continued Phenotypic and environmental
variables impacting fertility success Stress
Thickness and type of endometrium throughout the menstrual cycle.
Age
Height
Fertility treatment history and details: history of hormone stimulation,
brand of drugs used, basal antral follicle count, follicle count after
stimulation with different protocols, number/quality/stage of retrieved
oocytes/ development profile of embryos resulting from in vitro
insemination (natural or ICSI), details of IVF procedure (which clinic,
doctor/embryologist at clinic, assisted hatching, fresh or thawed
oocytes/embryos, embryo transfer (blood on the catheter/squirt
detection and direction on ultrasound), number of successful
and unsuccessful IVF attempts
Morning sickness during pregnancy
Breast size before/during/after pregnancy
History of ovarian cysts
Twin or sibling from multiple birth (mono-zygotic or di-zygotic)
Male factor infertility for reproductive partner: Semen analysis
(count, motility, morphology), Vasectomy, male cancer, smoking,
alcohol, diet, STIs
Blood type
DES exposure in utero
Past and current exercise/athletic history
Levels of phthalates, including metabolites:
MEP - monoethyl phthalate,
MECPP - mono(2-ethyl-5-carboxypentyl) phthalate,
MEHHP - mono(2-ethyl-5-hydroxyhexyl) phthalate,
MEOHP - mono(2-ethyl-5-ox-ohexyl) phthalate,
MBP - monobutyl phthalate,
MBzP - monobenzyl phthalate,
MEHP - mono(2-ethylhexyl) phthalate,
MiBP - mono-isobutyl phthalate,
MCPP - mono(3-carboxypropyl) phthalate,
MCOP - monocarboxyisooctyl phthalate,
MCNP - monocarboxyisononyl phthalate
Familial history of Premature Ovarian Failure/Insufficiency
Autoimmunity history - Antiadrenal antibodies
(anti-21-hydroxylase antibodies), antiovarian antibodies,
antithyroid anitibodies (anti-thyroid peroxidase, antithyroglobulin)
Hormone levels: Leutenizing hormone (using immunofluorometric
assay), Δ4-Androstenedione (using radioimmunoassay),
Dehydroepiandrosterone (using radioimmunoassay),
and Inhibin B (commercial ELISA)
Number of years trying to conceive
Dioxin and PVC exposure
Hair color
Nevi (moles)
Lead, cadmium, and other heavy metal exposure Information regarding the fertility-associated phenotypic traits of the female, such as those listed in Table 8, can be obtained by any means known in the art. In many cases, such information can be obtained from a questionnaire completed by the subject that contains questions regarding certain fertility-associated phenotypic traits. Additional information can be obtained from a questionnaire completed by the subject's partner and blood relatives. The questionnaire includes questions regarding the subject's fertility-associated phenotypic traits, such as her age, smoking habits, or frequency of alcohol consumption. Information can also be obtained from the medical history of the subject, as well as the medical history of blood relatives and other family members. Additional information can be obtained from the medical history and family medical history of the subject's partner. Medical history information can be obtained through analysis of electronic medical records, paper medical records, a series of questions about medical history included in the questionnaire, and a combination thereof. In other cases, the information can be obtained by analyzing a sample collected from the female subject, reproductive partners of the subject, blood relatives of the subject, and a combination thereof. The sample may include human tissue or bodily fluid. Any of the assays described herein may be used to obtain the phenotypic trait.

In other embodiments, an assay specific to an environmental exposure is used to obtain the phenotypic trait of interest. Such assays are known to those of skill in the art, and may be used with methods of the invention. For example, the hormones used in birth control pills (estrogen and progesterone) may be detected from a urine or blood test. Venners et al. (Hum. Reprod. 21(9): 2272-2280, 2006) reports assays for detecting estrogen and progesterone in urine and blood samples. Venner also reports assays for detecting the chemicals used in fertility treatments.

Similarly, illicit drug use may be detected from a tissue or body fluid, such as hair, urine sweat, or blood, and there are numerous commercially available assays (LabCorp) for conducting such tests. Standard drug tests look for ten different classes of drugs, and the test is commercially known as a "10-panel urine screen". The 10-panel urine screen consists of the following: 1. Amphetamines (including Methamphetamine) 2. Barbiturates 3. Benzodiazepines 4. Cannabinoids $(THC)_5$. Cocaine 6. Methadone 7. Methaqualone 8. Opiates (Codeine, Morphine, Heroin, Oxycodone, Vicodin, etc.) 9. Phencyclidine (PCP) 10. Propoxyphene. Use of alcohol can also be detected by such tests.

Numerous assays can be used to tests a patient's exposure to plastics (e.g., Bisphenol A (BPA)). BPA is most commonly found as a component of polycarbonates (about 74% of total BPA produced) and in the production of epoxy resins (about 20%). As well as being found in a myriad of products including plastic food and beverage contains (including baby and water bottles), BPA is also commonly found in various household appliances, electronics, sports safety equipment, adhesives, cash register receipts, medical devices, eyeglass lenses, water supply pipes, and many other products. Assays for testing blood, sweat, or urine for presence of BPA are described, for example, in Genuis et al. (Journal of Environmental and Public Health, Volume 2012, Article ID 185731, 10 pages, 2012).

Association studies can be performed to analyze the effect of genetic mutations or abnormal gene expression on a particular trait being studied. Infertility as a trait may be analyzed as a non-continuous variable in a case-control study that includes as the patients infertile females and as controls fertile females that are age and ethnically matched. Methods including logistic regression analysis and Chi square tests may be used to identify an association between genetic mutations or abnormal gene expression and infertility. In addition, when using logistic regression, adjustments for covariates like age, smoking, BMI and other factors that effect infertility, such as those shown in Table 4, may be included in the analysis.

In addition, haplotype effects can be estimated using programs such as Haploscore. Alternatively, programs such as Haploview and Phase can be used to estimate haplotype frequencies and then further analysis such as Chi square test can be performed. Logistic regression analysis may be used to generate an odds ratio and relative risk for each genetic variant or variants.

The association between genetic mutations and/or abnormal gene expression and infertility may be analyzed within cases only or comparing cases and controls using analysis of variance. Such analysis may include, adjustments for covariates like age, smoking, BMI and other factors that effect infertility. In addition, haplotype effects can be estimated using programs such as Haploscore.

Method of logistic regression are described, for example in, Ruczinski (Journal of Computational and Graphical Statistics 12:475-512, 2003); Agresti (An Introduction to Categorical Data Analysis, John Wiley & Sons, Inc., 1996, New York, Chapter 8); and Yeatman et al. (U.S. patent application number 2006/0195269), the content of each of which is hereby incorporated by reference in its entirety.

Other algorithms for analyzing associations are known. For example, the stochastic gradient boosting is used to generate multiple additive regression tree (MART) models to predict a range of outcome probabilities. Each tree is a recursive graph of decisions the possible consequences of which partition patient parameters; each node represents a question (e.g., is the FSH level greater than x?) and the branch taken from that node represents the decision made (e.g. yes or no). The choice of question corresponding to each node is automated. A MART model is the weighted sum of iteratively produced regression trees. At each iteration, a regression tree is fitted according to a criterion in which the samples more involved in the prediction error are given priority. This tree is added to the existing trees, the prediction error is recalculated, and the cycle continues, leading to a progressive refinement of the prediction. The strengths of this method include analysis of many variables without knowledge of their complex interactions beforehand.

A different approach called the generalized linear model, expresses the outcome as a weighted sum of functions of the predictor variables. The weights are calculated based on least squares or Bayesian methods to minimize the prediction error on the training set. A predictor's weight reveals the effect of changing that predictor, while holding the others constant, on the outcome. In cases where one or more predictors are highly correlated, in a phenomenon known as collinearity, the relative values of their weights are less meaningful; steps must be taken to remove that collinearity, such as by excluding the nearly redundant variables from the model. Thus, when properly interpreted, the weights express the relative importance of the predictors. Less general formulations of the generalized linear model include linear regression, multiple regression, and multifactor logistic regression models, and are highly used in the medical community as clinical predictors.

Microarrays

In certain aspects, the invention provides a microarray including a plurality of oligonucleotides attached to a substrate at discrete addressable positions, in which at least one of the oligonucleotides hybridizes to a portion of a genetic region from Table 1 that includes an infertility-associated mutation.

Methods of constructing microarrays are known in the art. See for example Yeatman et al. (U.S. patent application number 2006/0195269), the content of which is hereby incorporated by reference in its entirety.

Microarrays are prepared by selecting probes that include a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support, which may be either porous or non-porous. For example, the probes of the invention may be polynucleotide sequences, which are attached to a nitrocellulose or nylon membrane or filter covalently at either the 3' or the 5' end of the polynucleotide. Such hybridization probes are well known in the art (see, e.g., Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, the solid support or surface may be a glass or plastic surface. In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In preferred embodiments, a microarray comprises a support or surface with an ordered array of binding (e.g., hybridization) sites or "probes" each representing one of the genes described herein, particularly the genes described in Table 1. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 1 $cm^2$ and 25 $cm^2$, between 12 $cm^2$ and 13 $cm^2$, or 3 $cm^2$. However, larger arrays are also contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

The microarrays of the present invention include one or more test probes, each of which has a polynucleotide sequence that is complementary to a subsequence of RNA or DNA to be detected. Preferably, the position of each probe on the solid surface is known. Indeed, the microarrays are preferably positionally addressable arrays. Specifically, each probe of the array is preferably located at a known, predetermined position on the solid support such that the identity (i.e., the sequence) of each probe can be determined from its position on the array (i.e., on the support or surface).

According to the invention, the microarray is an array (i.e., a matrix) in which each position represents one of the biomarkers described herein. For example, each position can contain a DNA or DNA analogue based on genomic DNA to which a particular RNA or cDNA transcribed from that genetic marker can specifically hybridize. The DNA or DNA analogue can be, e.g., a synthetic oligomer or a gene fragment. In one embodiment, probes representing each of the markers is present on the array. In a preferred embodiment, the array comprises probes for each of the genes listed in Table 1.

As noted above, the probe to which a particular polynucleotide molecule specifically hybridizes according to the invention contains a complementary genomic polynucleotide sequence. The probes of the microarray preferably consist of nucleotide sequences of no more than 1,000 nucleotides. In some embodiments, the probes of the array consist of nucleotide sequences of 10 to 1,000 nucleotides. In a preferred embodiment, the nucleotide sequences of the probes are in the range of 10-200 nucleotides in length and are genomic sequences of a species of organism, such that a plurality of different probes is present, with sequences complementary and thus capable of hybridizing to the genome of such a species of organism, sequentially tiled across all or a portion of such genome. In other specific embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, and most preferably are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., PCR PROTOCOLS: A GUIDE TO METHODS AND APPLICATIONS, Academic Press Inc., San Diego, Calif. (1990). It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995)).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251: 767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510, 270) or other methods for rapid synthesis and deposition of defined oligonucleotides (Blanchard et al., Biosensors & Bioelectronics 11:687-690). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids. Res. 20:1679-1684), may also be used. In principle, and as noted supra, any type of array, for example, dot blots on a nylon hybridization membrane (see Sambrook et al., MOLECULAR CLONING—A LABORATORY MANUAL (2ND ED.), Vols. 1-3, Cold Spring Harbor Laboratory, Cold Spring Harbor, N.Y. (1989)) could be used. However, as will be recognized by those skilled in the art, very small arrays will frequently be preferred because hybridization volumes will be smaller.

In one embodiment, the arrays of the present invention are prepared by synthesizing polynucleotide probes on a support. In such an embodiment, polynucleotide probes are attached to the support covalently at either the 3' or the 5' end of the polynucleotide.

In a particularly preferred embodiment, microarrays of the invention are manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 µL or less) and are separated from each other on the microarray (e.g., by hydrophobic domains) to form circular surface tension wells, which define the locations of the array elements (i.e., the different probes). Microarrays manufactured by this ink-jet method are typically of high density, preferably having a density of at least about 2,500 different probes per 1 cm.sup.2. The polynucleotide probes are attached to the support covalently at either the 3' or the 5' end of the polynucleotide.

The polynucleotide molecules which may be analyzed by the present invention are DNA, RNA, or protein. The target polynucleotides are detectably labeled at one or more nucleotides. Any method known in the art may be used to detectably label the target polynucleotides. Preferably, this labeling incorporates the label uniformly along the length of the DNA or RNA, and more preferably, the labeling is carried out at a high degree of efficiency.

In a preferred embodiment, the detectable label is a luminescent label. For example, fluorescent labels, bioluminescent labels, chemiluminescent labels, and colorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.). In another embodiment, the detectable label is a radiolabeled nucleotide.

In a further preferred embodiment, target polynucleotide molecules from a patient sample are labeled differentially from target polynucleotide molecules of a reference sample. The reference can comprise target polynucleotide molecules from normal tissue samples.

Nucleic acid hybridization and wash conditions are chosen so that the target polynucleotide molecules specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook et al., MOLECULAR CLONING—A LABORATORY MANUAL (2ND ED.), Vols. 1-3, Cold Spring Harbor Laboratory, Cold Spring Harbor, N.Y. (1989), and in Ausubel et al., CURRENT PROTOCOLS IN MOLECULAR BIOLOGY, vol. 2, Current Protocols Publishing, New York (1994). Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, HYBRIDIZATION WITH NUCLEIC ACID PROBES, Elsevier Science Publishers B.V.; and Kricka, 1992, NONISOTOPIC DNA PROBE TECHNIQUES, Academic Press, San Diego, Calif.

Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled genetic regions or products of these genetic regions are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

Computer Systems

Figure 15:
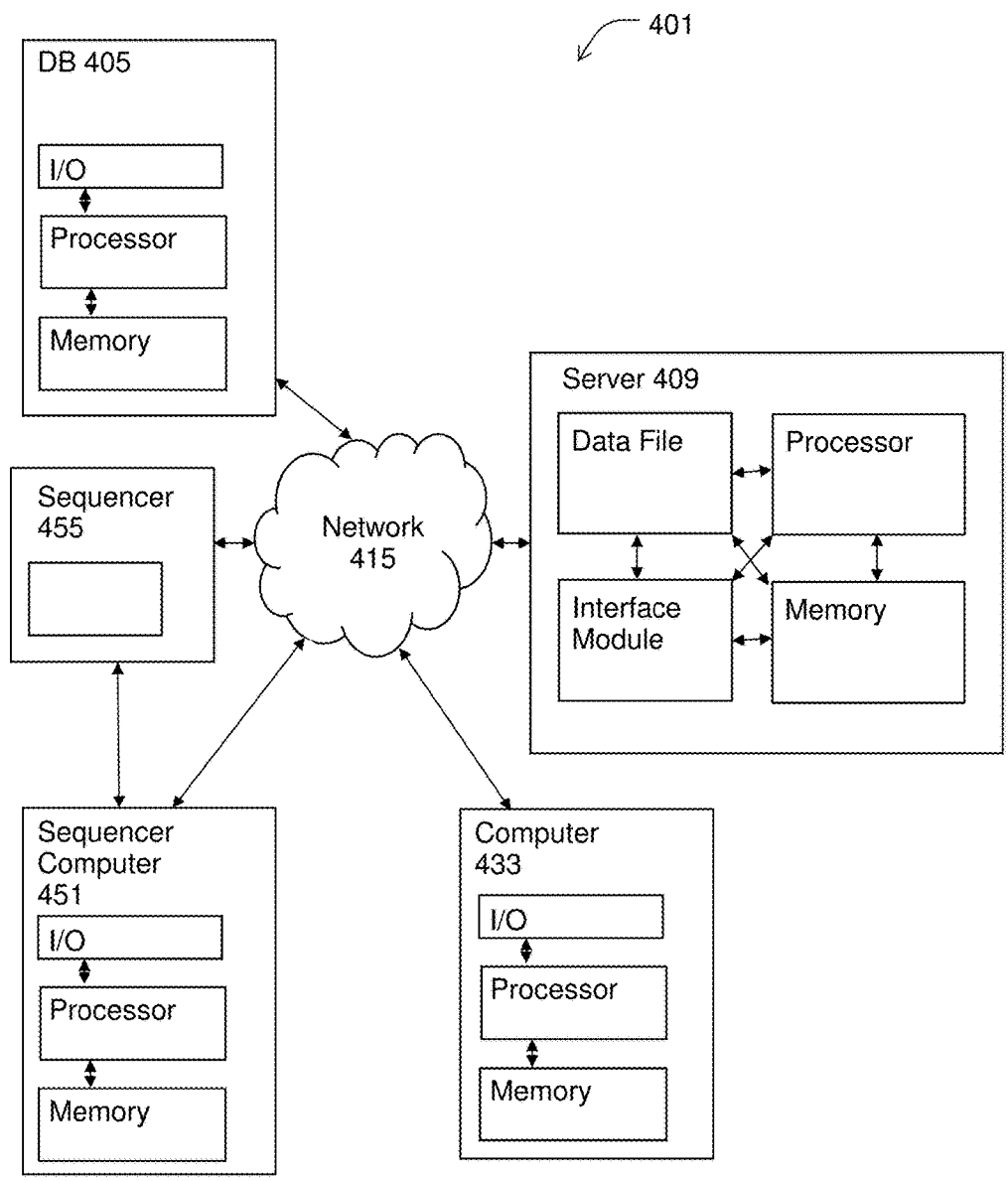
FIG. 15 illustrates a system for implementing methods of the invention.

FIG. 15 illustrates a computer system 401 useful for implementing methodologies described herein. A system of the invention may include any one or any number of the components shown in FIG. 15. Generally, a system 401 may include a computer 433 and a server computer 409 capable of communication with one another over network 415. Additionally, data may optionally be obtained from a database 405 (e.g., local or remote). In some embodiments, systems include an instrument 455 for obtaining sequencing data, which may be coupled to a sequencer computer 451 for initial processing of sequence reads.

In some embodiments, methods are performed by parallel processing and server 409 includes a plurality of processors with a parallel architecture, i.e., a distributed network of processors and storage capable of collecting, filtering, processing, analyzing, ranking genetic data obtained through methods of the invention. The system may include a plurality of processors configured to, for example, 1) collect genetic data from different modalities: a) one or more infertility databases 405 (e.g. infertility databases, including private and public fertility-related data), b) from one or more sequencers 455 or sequencing computers 451, c) from mouse modeling, etc; 2) filter the genetic data to identify genetic variations; 3) associate genetic variations with infertility using methods described throughout the application (e.g., filtering, clustering, etc.); 4) determine statistical significance of genetic variations based on fertility criteria defined herein (e.g., Example 18); and 5) characterize/identify the genetic variations as infertility biomarkers.

By leveraging genetic data sets obtained across different sources, applying layers of analyses (i.e., filtering, clustering, etc.) to genetic data, and quantifying/qualifying statistical significance of that genetic data, systems of the invention are able yield and identify new infertility biomarkers that previously could not be determined to have any association with infertility. For example, methods of the invention utilize data sets from different modalities. The data sets range include data obtained from infertility databases (e.g., public and private), sequencing data (e.g., whole genome sequencing from one or more biological samples), and genetic data obtained from mouse modeling, etc. Several layers of analysis are then applied to the genetic data to identify whether variations are potentially associated with infertility. Particularly, the genetic data sets are subject to evolutionary conservation analysis, filtering analysis (see FIG. 5) and/or subject to clustering analysis (Example 20). After those analyses are applied, the variants potentially associated with infertilty are then assessed for biological and statistical significance. The variants that are determined to be statistically significant are then classified as infertility biomarkers, even if those variant had no prior association with infertility. Accordingly, using the invention's multimodal and layered analysis, one is able to identify infertility biomarkers that would not have been identified or associated with infertility using standard techniques (i.e. comparing genetic sequences of an abnormal, infertile population to genetic sequences of a normal, fertile population).

While other hybrid configurations are possible, the main memory in a parallel computer is typically either shared between all processing elements in a single address space, or distributed, i.e., each processing element has its own local address space. (Distributed memory refers to the fact that the memory is logically distributed, but often implies that it is physically distributed as well.) Distributed shared memory and memory virtualization combine the two approaches, where the processing element has its own local memory and access to the memory on non-local processors. Accesses to local memory are typically faster than accesses to non-local memory.

Computer architectures in which each element of main memory can be accessed with equal latency and bandwidth are known as Uniform Memory Access (UMA) systems. Typically, that can be achieved only by a shared memory system, in which the memory is not physically distributed. A system that does not have this property is known as a Non-Uniform Memory Access (NUMA) architecture. Distributed memory systems have non-uniform memory access.

Processor-processor and processor-memory communication can be implemented in hardware in several ways, including via shared (either multiported or multiplexed) memory, a crossbar switch, a shared bus or an interconnect network of a myriad of topologies including star, ring, tree, hypercube, fat hypercube (a hypercube with more than one processor at a node), or n-dimensional mesh.

Parallel computers based on interconnected networks must incorporate routing to enable the passing of messages between nodes that are not directly connected. The medium used for communication between the processors is likely to be hierarchical in large multiprocessor machines. Such resources are commercially available for purchase for dedicated use, or these resources can be accessed via "the cloud," e.g., Amazon Cloud Computing.

A computer generally includes a processor coupled to a memory and an input-output (I/O) mechanism via a bus. Memory can include RAM or ROM and preferably includes at least one tangible, non-transitory medium storing instructions executable to cause the system to perform functions described herein. As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

A processor may be any suitable processor known in the art, such as the processor sold under the trademark XEON E7 by Intel (Santa Clara, Calif.) or the processor sold under the trademark OPTERON 6200 by AMD (Sunnyvale, Calif.).

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1—Identification of Oocyte Proteins

Oocytes are collected from females, for example mice, by superovulation, and zona pellucidae are removed by treatment with acid Tyrode solution. Oocyte plasma membrane (oolemma) proteins exposed on the surface can be distinguished at this point by biotin labeling. The treated oocytes are washed in 0.01 M PBS and treated with lysis buffer (7 M urea, 2 M thiourea, 4% (w/v) 3-[(3-cholamidopropyl) dimethylammonio]-1-propanesulfonate (CHAPS), 65 mM dithiothreitol (DTT), and 1% (v/v) protease inhibitor at −80° C.). Oocyte proteins are resolved by one-dimensional or two-dimensional SDS-PAGE. The gels are stained, visualized, and sliced. Proteins in the gel pieces are digested (12.5 ng/μl trypsin in 50 mM ammonium bicarbonate overnight at 37° C.), and the peptides are extracted and microsequenced.

Example 2—Sample Population for Identification of Infertility-Related Polymorphisms Genomic DNA is collected from 30 female subjects (15 who have failed multiple rounds of IVF versus 15 who were successful). In particular, all of the subjects are under age 38. Members of the control group succeeded in conceiving through IVF. Members of the test group have a clinical diagnosis of idiopathic infertility, and have failed three of more rounds of IVF with no prior pregnancy. The women are able to produce eggs for IVF and have a reproductively normal male partner. To focus on infertility resulting from oocyte defects (and eliminate factors such as implantation defects) women who have subsequently conceived by egg donation are favored.

Example 3—Sample Population for Identification of Infertility-Related Polymorphisms In a follow-up study of a larger cohort, genomic DNA is collected from 300 female subjects (divided into groups having profiles similar to the groups described above). The DNA sequence polymorphisms to be investigated are selected based on the results of small initial studies.

Example 4—Sample Population for Identification of Premature Ovarian Failure (POF) and Premature Maternal Aging Polymorphisms Genomic DNA is collected from 30 female subjects who are experiencing symptoms of premature decline in egg quality and reserve including abnormal menstrual cycles or amenorrhea. In particular, all of the subjects are between the ages of 15-40 and have follicle stimulating hormone (FSH) levels of over 20 international units (IU) and a basal antral follicle count of under 5. Members of the control group succeeded in conceiving through IVF. Members of the test group have no previous history of toxic exposure to known fertility damaging treatments such as chemotherapy. Members of this group may also have one or more female family member who experienced menopause before the age of 40.

Example 5—Sample Procurement and Preparation

Blood is drawn from patients at fertility clinics for standard procedures such as gauging hormone levels and many clinics bank this material after consent for future research projects. Although DNA is easily obtained from blood, wider population sampling is accomplished using home-based, noninvasive methods of DNA collection such as saliva using an Oragene DNA self collection kit (DNA Genotek).

Blood samples—Three-milliliter whole blood samples are venously collected and treated with sodium citrate anticoagulant and stored at 4° C. until DNA extraction.

Whole Saliva—Whole saliva is collected using the Oragene DNA selfcollection kit following the manufacturer's instructions. Participants are asked to rub their tongues around the inside of their mouths for about 15 sec and then deposit approximately 2 ml saliva into the collection cup. The collection cup is designed so that the solution from the vial.'s lower compartment is released and mixes with the saliva when the cap is securely fastened. This starts the initial phase of DNA isolation, and stabilizes the saliva sample for long-term storage at room temperature or in low temperature freezers. Whole saliva samples are stored and shipped, if necessary, at room temperature. Whole saliva has the potential advantage over other non-invasive DNA sampling methods, such as buccal and oral rinse, of providing large numbers of nucleated cells (eg., epithelial cells, leukocytes) per sample.

Blood clots—Clotted blood that is usually discarded after extraction through serum separation, for other laboratory tests such as for monitoring reproductive hormone levels is collected and stored at −80° C. until extraction.

Sample Preparation—Genomic DNA is prepared from patient blood or saliva for downstream sequencing applications with commercially available kits (e.g., Invitrogen.'s ChargeSwitch® gDNA Blood Kit or DNA Genotek kits, respectively). Genomic DNA from clotted is prepared by standard methods involving proteinase K digestion, salt/chloroform extraction and 90% ethanol precipitation of DNA. (see N Kanai et al., 1994, "Rapid and simple method for preparation of genomic DNA from easily obtainable clotted blood," J Clin Pathol 47:1043-1044, which is incorporated by reference in its entirety for all purposes).

Example 6—Manufacturing of a Customized Oligonucleotide Library

A customized oligonucleotide library can be used to enrich samples for DNAs of interest. Several methods for manufacturing customized oligonucleotide libraries are known in the art. In one example, Nimblegen sequence capture custom array design is used to create a customized target enrichment system tailored to infertility related genes. A customized library of oligonucleotides is designed to target genetic regions of Tables 1-7. The custom DNA oligonucleotides are synthesized on a high density DNA Nimblegen Sequence Capture Array with Maskless Array Synthesizer (MAS) technology. The Nimblegen Sequence Capture Array system workflow is array based and is performed on glass slides with an X1 mixer (Roche NimbleGen) and the NimbleGen Hybridization System.

In a similar example, Agilent's eArray (a web-based design tool) is used to create a customized target enrichment system tailored to infertility related genes. The SureSelect Target Enrichment System workflow is solution-based and is performed in microcentrifuge tubes or microtiter plates. A customized oligonucleotide library is used to enrich samples for DNA of interest. Agilent's eArray (a web-based design tool) is used to create a customized target enrichment system tailored to infertility related genes. A customized library is designed to target genetic regions of Tables 1-7. The custom RNA oligonucleotides, or baits, are biotinylated for easy capture onto streptavidin-labeled magnetic beads and used in Agilent's SureSelectTarget Enrichment System. The SureSelect Target Enrichment System workflow is solution-based and is performed in microcentrifuge tubes or microtiter plates.

Example 7—Capture of Genomic DNA

Genomic DNA is sheared and assembled into a library format specific to the sequencing instrument utilized downstream. Size selection is performed on the sheared DNA and confirmed by electrophoresis or other size detection method.

Several methods to capture genomic DNA are known in the art. In one example, the size-selected DNA is purified and the ends are ligated to annealed oligonucleotide linkers from Illumina to prepare a DNA library. DNA-adaptor ligated fragments are hybrized to a Nimblegen Sequence Capture array using an X1 mixer (Roche NimbleGen) and the Roche NimbleGen Hybridization System. After hybridization, are washed and DNA fragments bound to the array are eluted with elution buffer. The captured DNA is then dried by centrifugation, rehydrated and PCR amplified with polymerase. Enrichment of DNA can be assessed by quantitative PCR comparison to the same sample prior to hybridization.

In a similar example, the size-selected DNA is incubated with biotinylated RNA oligonucleotides "baits" for 24 hours. The RNA/DNA hybrids are immobilized to streptavidin-labeled magnetic beads, which are captured magnetically. The RNA baits are then digested, leaving only the target selected DNA of interest, which is then amplified and sequenced.

Example 8—Sequencing of Target Selected DNA

Target-selected DNA is sequenced by a paired end (50 bp) re-sequencing procedure using Illumina.'s Genome Analyzer. The combined DNS targeting and resequencing provides 45 fold redundancy which is greater than the accepted industry standard for SNP discovery.

Example 9—Correlation of Polymorphisms with Fertility

Polymorphisms among the sequences of target selected DNA from the pool of test subjects are identified, and may be classified according to where they occur in promoters, splice sites, or coding regions of a gene. Polymorphisms can also occur in regions that have no apparent function, such as introns and upstream or downstream non-coding regions. Although such polymorphisms may not be informative as to the functional defect of an allele, nevertheless, they are linked to the defect and useful for predicting infertility. The polymorphisms are analyzed statistically to determine their correlation with the fertility status of the test subjects. The statistical analysis indicates that certain polymorphisms identify gene defects that by themselves (homozygous or heterozygous) are sufficient to cause infertility. Other polymorphisms identify genetic variants that reduce, but do not eliminate fertility. Other polymorphisms identify genetic variants that have an apparent effect on fertility only in the presence of particular variants of other genes. Other polymorphisms identify genetic variants that have an apparent effect on fertility only in the presence of particular phenotypes. Other polymorphisms identify genetic variants that have an apparent effect on fertility only in the presence of particular environmental exposures. Still other polymorphisms identify genetic variants that have an apparent effect on fertility only in the presence of any combination of particular variants of other genes, presence of particular phenotypes, and particular environmental exposures.

Example 10—Correlation of Polymorphisms with Premature Ovarian Failure (POF)

Polymorphisms among the sequences of target selected DNA from the pool of test subjects are identified, and may be classified according to where they occur in promoters, splice sites, or coding regions of a gene. Polymorphisms can also occur in regions that have no apparent function, such as introns and upstream or downstream non-coding regions. Although such polymorphisms may not be informative as to the functional defect of an allele, nevertheless, they are linked to the defect and useful for predicting likelihood of premature ovarian failure (POF). The polymorphisms are analyzed statistically to determine their correlation with the POF status of the test subjects. The statistical analysis indicates that certain polymorphisms identify gene defects that by themselves (homozygous or heterozygous) are sufficient to cause POF. Other polymorphisms identify genetic variants that increase the likelihood, but do not cause POF. Other polymorphisms identify genetic variants that have an apparent effect on POF only in the presence of particular variants of other genes. Other polymorphisms identify genetic variants that have an apparent effect on POF only in the presence of particular phenotypes. Other polymorphisms identify genetic variants that have an apparent effect on POF only in the presence of particular environmental exposures. Still other polymorphisms identify genetic variants that have an apparent effect on POF only in the presence of any combination of particular variants of other genes, presence of particular phenotypes, and particular environmental exposures.

Example 11—Correlation of Polymorphisms with Premature Maternal Aging

Polymorphisms among the sequences of target selected DNA from the pool of test subjects are identified, and may be classified according to where they occur in promoters, splice sites, or coding regions of a gene. Polymorphisms can also occur in regions that have no apparent function, such as introns and upstream or downstream non-coding regions. Although such polymorphisms may not be informative as to the functional defect of an allele, nevertheless, they are linked to the defect and useful for predicting likelihood of premature decline in ovarian reserve and egg quality (i.e. maternal aging). The polymorphisms are analyzed statistically to determine their correlation with the maternal aging status of the test subjects. The statistical analysis indicates that certain polymorphisms identify gene defects that by themselves (homozygous or heterozygous) are sufficient to cause premature maternal aging. Other polymorphisms identify genetic variants that increase the likelihood, but do not cause premature maternal aging. Other polymorphisms identify genetic variants that have an apparent effect on premature maternal aging only in the presence of particular variants of other genes. Other polymorphisms identify genetic variants that have an apparent effect on premature maternal aging only in the presence of particular phenotypes. Other polymorphisms identify genetic variants that have an apparent effect on premature maternal aging only in the presence of particular environmental exposures. Still other polymorphisms identify genetic variants that have an apparent effect on premature maternal aging only in the presence of any combination of particular variants of other genes, presence of particular phenotypes, and particular environmental exposures.

Example 12—Diagnostics and Counseling

A library of nucleic acids in an array format is provided for infertility diagnosis. The library consists of selected nucleic acids for enrichment of genetic targets wherein polymorphisms in the targets are correlated with variations in fertility. A patient nucleic acid sample (appropriately cleaved and size selected) is applied to the array, and patient nucleic acids that are not immobilized are washed away. The immobilized nucleic acids of interest are then eluted and sequenced to detect polymorphisms. According to the polymorphisms detected, the fertility status of the patient is evaluated and/or quantified. The patient is accordingly advised as to the suitability and likelihood of success of a fertility treatment or suitability or necessity of a particular in vitro fertilization procedure.

Example 13—Diagnostics and Counseling

A complete DNA sequence of any number of or all of the genes in Tables 1-7 is determined using a targeted resequencing protocol. According to the polymorphisms detected and the phenotypic traits and environmental exposures reported, the fertility status of the patient is evaluated and/or quantified. The patient is accordingly advised as to the suitability and likelihood of success of a fertility treatment or suitability or necessity of a particular in vitro fertilization procedure.

Example 14—Diagnostics and Counseling

A library of nucleic acids in an array format is provided for infertility diagnosis. The library consists of selected nucleic acids for enrichment of genetic targets wherein polymorphisms in the targets are correlated with variations in fertility. A patient nucleic acid sample (appropriately cleaved and size selected) is applied to the array, and patient nucleic acids that are not immobilized are washed away. The immobilized nucleic acids of interest are then eluted and sequenced to detect polymorphisms. According to the polymorphisms detected and the phenotypic traits and environmental exposures reported, the POF status of the patient or likelihood of future POF occurrence is evaluated and/or quantified. The patient is accordingly advised as to whether preventative egg or ovary preservation is indicated.

Example 15—Diagnostics and Counseling

A complete DNA sequence of any number of or all of the genes in Tables 1-7 is determined using a targeted resequencing protocol. According to the polymorphisms detected and the phenotype and environmental exposures reported, the fertility status of the patient is evaluated and/or quantified. According to the polymorphisms detected and the phenotypic traits and environmental exposures reported, the POF status of the patient or likelihood of future POF occurrence is evaluated and/or quantified. The patient is accordingly advised as to whether preventative egg or ovary preservation is indicated.

Example 16—Diagnostics and Counseling

A library of nucleic acids in an array format is provided for infertility diagnosis. The library consists of selected nucleic acids for enrichment of genetic targets wherein polymorphisms in the targets are correlated with variations in fertility. A patient nucleic acid sample (appropriately cleaved and size selected) is applied to the array, and patient nucleic acids that are not immobilized are washed away. The immobilized nucleic acids of interest are then eluted and sequenced to detect polymorphisms. According to the polymorphisms detected and the phenotypic traits and environmental exposures reported, the maternal aging status of the patient or likelihood of future premature maternal aging occurrence is evaluated and/or quantified. The patient is accordingly advised as to whether preventative egg or ovary preservation, minimization of certain environmental exposures such as alcohol intake or smoking, or mitigation of certain phenotypes such as having children at a younger age is indicated.

Example 17—Diagnostics and Counseling

A complete DNA sequence of any number of or all of the genes in Tables 1-7 is determined using a targeted resequencing protocol. According to the polymorphisms detected and the phenotypic traits and environmental exposures reported, the fertility status of the patient is evaluated and/or quantified. According to the polymorphisms detected and the phenotype and environmental exposures reported, the maternal aging status of the patient or likelihood of future premature maternal aging occurrence is evaluated and/or quantified. The patient is accordingly advised as to whether preventative egg or ovary preservation, minimization of certain environmental exposures such as alcohol intake or smoking, or mitigation of certain phenotypes such as having children at a younger age is indicated.

Example 18—Whole Genome Sequencing for Female Infertility Biomarker Discovery

Whole genome sequencing (WGS) allows one to characterize the complete nucleic acid sequence of an individual's genome. With the amount of data obtained from WGS, a comprehensive collection of an individual's genetic variation is obtainable, which provides great potential for genetic biomarker discovery. The data obtained from WGS can be advantageously used to expand the ability to identify and characterize female infertility biomarkers. However, the ability to identify unknown variations of fertility significance within the vast WGS datasets is a challenging task that is analogous to finding a needle in a haystack.

Methods of the invention, according to certain embodiments, rely on bioinformatics to filter through WGS data in order to identify and prioritize variations of infertility significance. Specifically, the invention relies on a combination of clinical phenotypic data and an infertility knowledgebase to rank and/or score genomic regions of interest and their likely impact on different fertility disorders. In certain aspects, the filtering approach involves assessing sequencing data to identify genomic variations, identifying at least one of the variations as being in a genomic region associated with infertility, determining whether the at least one variation is a biologically-significant variation and/or a statistically-significant variation, and characterizing at least one identified variation as an infertility biomarker based on the determining step. A genomic region associated with infertility is any DNA sequence in which variation is associated with a change in fertility. Such regions may include genes (e.g. any region of DNA encoding a functional product), genetic regions (e.g. regions including genes and intergenic regions with a particular focus on regions conserved throughout evolution in placental mammals), and gene products (e.g., RNA and protein). In particular embodiments, the infertility-associated genetic region is a maternal effect gene, as described above. In particular embodiments, the infertility-associated genetic region is a gene (including exons, introns, and evolutionarily conserved regions of DNA flanking either side of said gene) that impacts fertility.

This filtering approach facilitates rapid identification of functionally relevant variants within genomic regions of significance for fertility. The identified variations with infertility significance obtained from WGS data may be used in diagnostic testing, and ultimately assist physicians in data interpretation, guide fertility therapeutics, and clarify why some patients are not responding to treatment. The following illustrates use of WGS data to identify variants of interest in accordance with methods of the invention.

Figure 5:
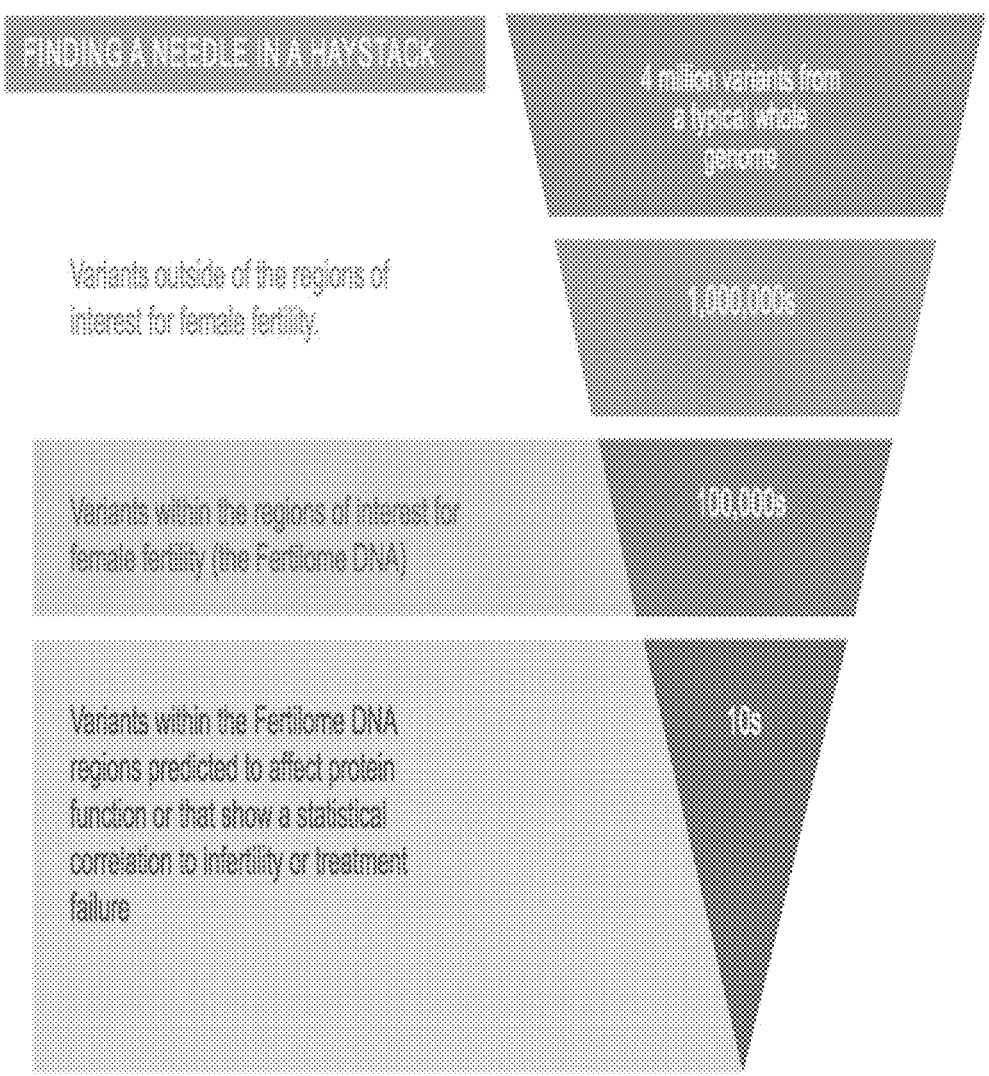
FIG. 5 depicts the method for filtering through variants detected in whole genome sequencing for the identification of genetic regions related to infertility.

FIG. 5 generally illustrates filtering through variations obtained from WGS sequencing data in order to identify variations of infertility significance. As shown in FIG. 5, the first step is to identify sequence variants in whole genome sequence. A typical whole genome can include up to four million variants. The next filtering step involves eliminating variants outside of regions of interest for female fertility (which amounts to about one million variants). Next, the filtering method isolates variants within regions of interest for female fertility, which is described herein as Fertilome nucleic acid (i.e. regions of the human genome that control egg quality and fertility). Variations located within the Fertilome nucleic acid may be in the 100,000s. The variations within the Fertilome nucleic acid are further filtered to identify and score variations of infertility significance (such variations are typically present in double digits). Particularly, variations of infertility significance include those within regions predicted to effect biological function or that show a statistical correlation to infertility or treatment failure.

Biologically-significant variations within the Fertilome nucleic acid include mutations that result in a change: 1) to a different amino acid predicted to alter the folding and/or structure of the encoded protein, 2) to a different amino acid occurring at a site with high evolutionarily conservation in mammals, 3) that introduces a premature stop termination signal, 4) that causes a stop termination signal to be lost, 5) that introduces a new start codon, 6) that causes a start codon to be lost or 7) that disrupts a splicing signal. Statistically-significant variations within the Fertilome nucleic acid are described in relation to and listed in Tables 2 and 3. Other methods for classifying variations as statistically- or biologically-significant includes scoring variations using an infertility knowledgebase (which is described in relation to Tables 5-7 above and FIG. 6 below). The infertility knowledgebase ranks genes based on attributes associated with infertility. The attributes include: diseases and disorders related to infertility, molecular pathways, molecular interactions, gene clusters, mouse phenotypes associated with each gene, gene expression data in reproductive tissues, proteomics data in oocytes, and accrued information from scientific publications through text-mining. List of ranked genes of interest are provided in Tables 5-7.

Figure 6:
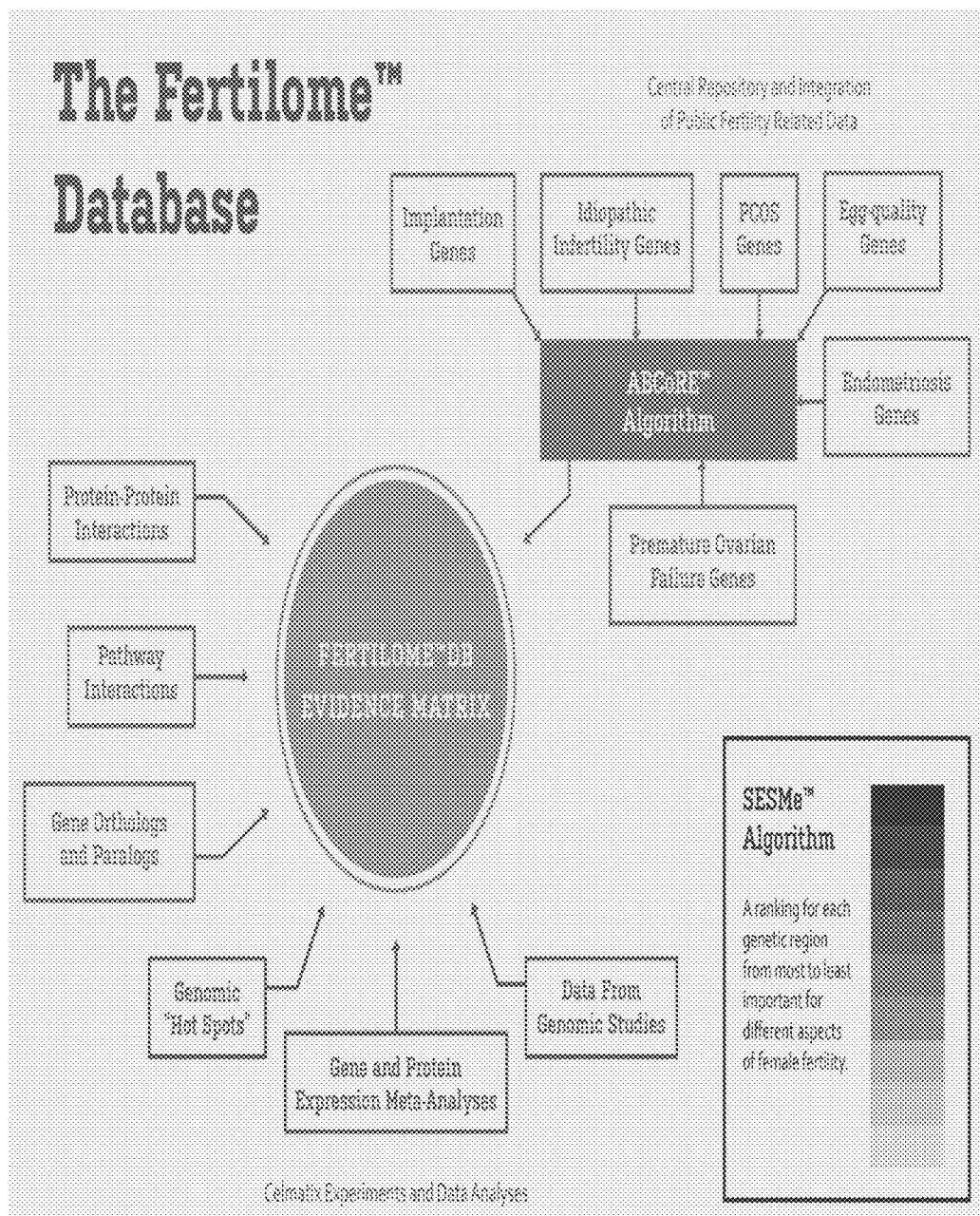
FIG. 6 depicts some of the components of the Fertilome™ Database, a tool for correlating genetic regions with risk for infertility (Fertilome™ Score).

FIG. 6 illustrates various data sources integrated into the infertility knowledgebase for analyzing whole-genome sequencing data according to certain embodiments. As shown in FIG. 6, information is obtained from private and public fertility-related data. Private and/or public fertility-related data may include implantation genes, idiopathic infertility genes, polycystic ovary syndrome (PCOS) genes, egg quality genes, endometriosis genes, and premature ovarian failure genes. The private and/or public fertility-related data is then subjected to the ABCoRE Algorithm to provide genomic regions and variations of interest that can be introduced into a fertility database evidence matrix along with other fertility-related information. As described in the detailed description, the ABCoRE algorithm identifies fertility regions of interest by performing evolutionary conservation analysis of one or more genes obtained from the private and/or public fertility-related data. The other fertility-related information includes, for example, protein-protein interactions, pathway interactions, gene orthologs and paralogs, genomic "hotpsots", gene protein expression and meta-analysis, and data from genomic studies. In operation, whole genomic sequencing data is compared to the compiled data in the fertility database evidence matrix to facilitate identification of potential genetic regions important for fertility. The fertility database evidence matrix filters through WGS variants to identify variants of fertility significance. In certain embodiments, the whole genomic sequencing data is also subjected to the SESMe algorithm that ranks each genetic region from most to least important for different aspects of female fertility.

Figure 7:
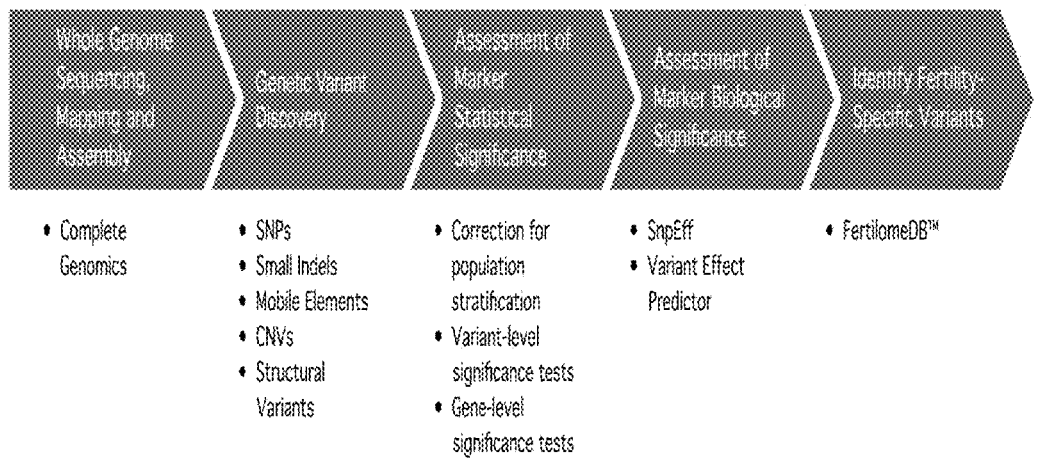
FIG. 7 is the bioinformatics pipeline used to identify biologically interesting and statistically significant genetic variants in infertile patients.
Figure 8:
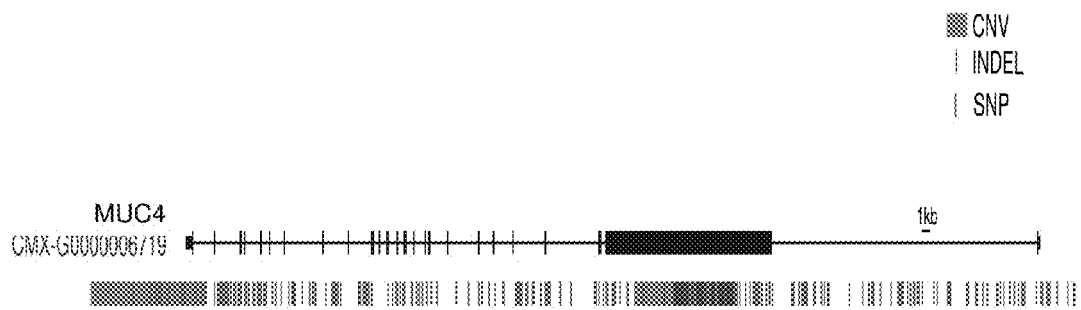
FIG. 8 shows the different types of biologically or statistically significant genetic variants that were detected in infertile patients in the MUC4 genetic region.

FIG. 7 illustrates a bioinformatics pipeline used to filter through WGS data to identify biomarkers associated with infertility according to certain embodiments. As shown in FIG. 7, samples are subjected to whole genome sequencing, mapping, and assembly. The WGS data is then analyzed to discover genetic variants such as SNPs, small indels, mobile elements, copy number variations, and structural variations. The identified variations are then assessed for statistical significance (See, for example, Tables 2 and 3 above). This includes correction for population stratification, variation-level significance tests, and gene level significance tests. In addition, the biological significance of WGS variants is determined using the SnpEff and Variant Effect Predictor (www.ensembl.org) engines (See, for example, Table 1 above). Variants of biological and statistical significance are then entered into the infertility knowledgebase (i.e. Fertilome database) in order to classify those variants as fertility biomarkers.

The following illustrates use of WGS data to identify variants of interest in accordance with methods of the invention.

Samples were collected from female patients undergoing fertility treatment at an academic reproductive medical center, and categorized into idiopathic infertility or primary ovarian insufficiency (POI) study groups. Phenotypic information was collected for each patient by mining >200 variables from electronic health records. Genomic DNA extracted from blood samples underwent WGS by Complete Genomics (Mountain View, Calif.). Analysis of genetic variants from WGS was assisted by an infertility knowledgebase with >800 genomic regions of interest (ROI) ranked by a scoring algorithm predicting their likely impact on different fertility disorders, based on publications, data repositories (including protein-protein interactions and tissue expression patterns), meta-analyses of these data, and animal model phenotypes.

The collected female samples were subjected to the processes/algorithms depicted in FIGS. 5-7 (described in more detail above). With those female samples, approximately 50,000 novel variants (approximately 1.6% of total variants observed) were identified as having fertility significances that have not been previously reported in databases such as the sbSNP reference. The identified fertility-related variants included single nucleotide polymorphisms (SNPs, insertions, deletions, copy number variations, inversions, and translocations. Of the SNPs, some of them are predictive to have putative functional significance based on the knowledgebase. For example, the knowledgebase scored some SNPs as deleterious mutations due to potential loss of function or changes in protein structure.

In certain aspects, the genomic data, such as WGS data, of a patient/subject population is subjected to a population stratification correction. Population stratification correction accounts for the presence of a systematic difference in allele frequencies between subpopulations in a population possibly due to different ancestry. When conducting population stratification, data is compared to a number (e.g. 1,000) of ethnically diverse individuals as part of the 1000 Genomes Project (100G). Principal components analysis (PCA) is applied to model and identify ancestry differences. In addition, computed association statistics are adjusted for the first two principal components.

Figure 13:
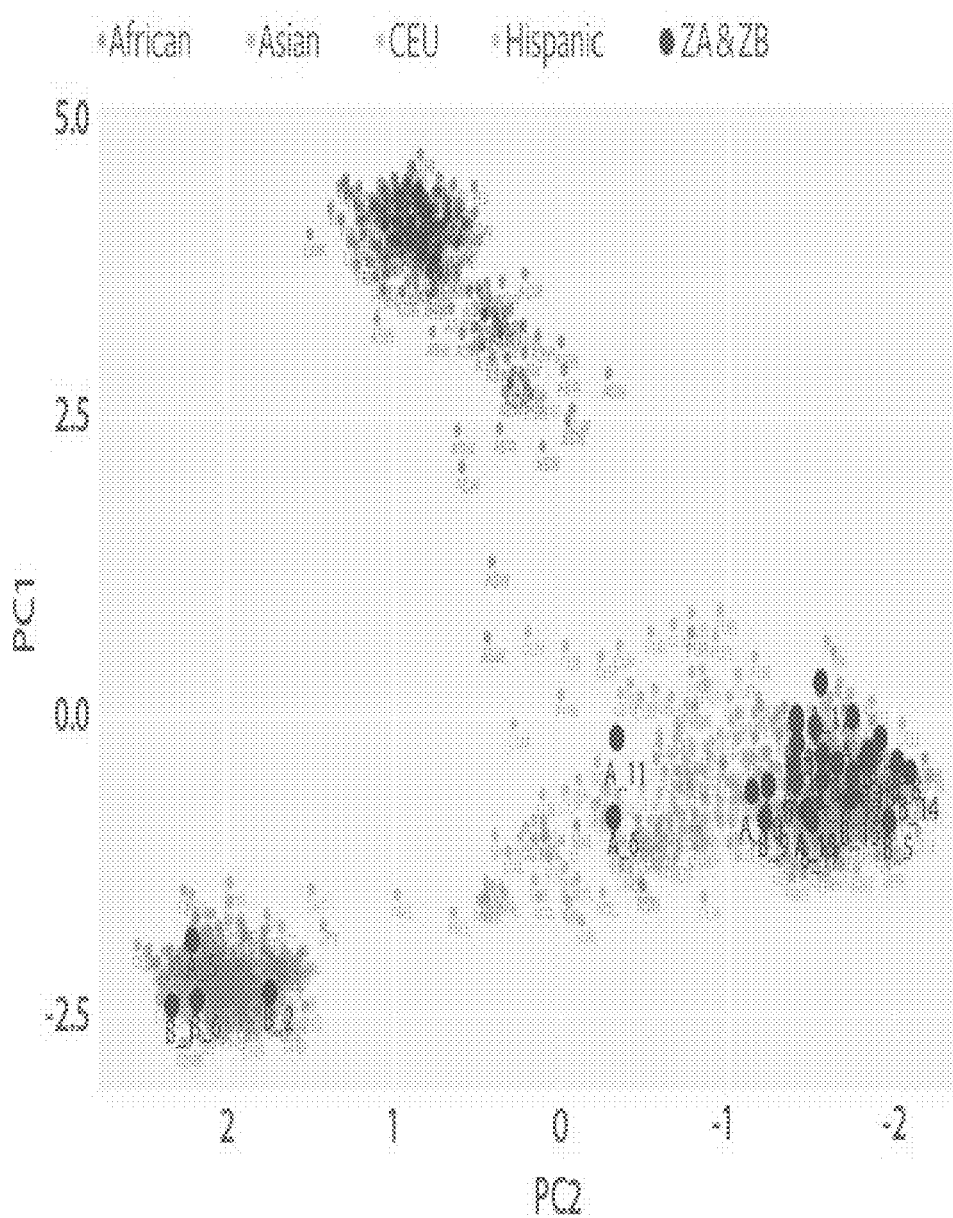
FIG. 13 illustrates population stratification correction of two patient groups (ZA=patients who did not get pregnant with IVF treatment, ZB=patients with infertility who did get pregnant with WF treatment).

FIG. 13 illustrates population stratification correction of two patient groups. The patient groups include female patients undergoing non-donor in vitro fertilization (IVF) cycles. The patients were 38 years old or younger at the time of enrollment, and had no history of carrying a pregnancy beyond the first term before IVF treatment. Each patient had lack of an apparent cause for infertility (i.e. unexplained) after an evaluation of a complete medical history, physical examination, endocrine profile, and the results of an intimate partner's sperm analysis. The patients were divided into two groups. Group A included 11 patients that experienced no live birth or pregnancy beyond the first trimester after 3 or more IVF cycles. Group B included 18 patients that experienced live birth or pregnancy beyond the first trimester through use of IVF therapy. With population stratification correction, Group A and B patients cluster (are shown as black dots) with East Asian, African, Hispanic, and European individuals as shown in the principal component analysis chart of FIG. 13. This data shows that ethnicity may be linked to infertility, or that certain genomic variations are more prevalent in certain ethnic populations. Accordingly, aspects of the invention involve assessing ethnicity of an individual, either through self-reporting by the individual (e.g., by a questionnaire) or via an assay that looks for known biomarkers related to genetic ethnicity of an individual. That ethnicity data (genetic or self-reported) may be used to guide testing, such as by ensuring that certain genomic variations are checked that are known to be associated with certain ethnic populations.

Example 19

Approximately 15% of couples experiencing difficulty conceiving are diagnosed with idiopathic infertility. Genetic polymorphisms could shed light on many of these currently unexplained cases by revealing disruptions to oocyte quality or uterine receptivity that may exist on a subcellular level.

In accordance with certain aspects, copy number variations are examined for their effect on female fertility using comparative genomic hybridization (CGH) arrays. CGH provides for methods of determining the relative number of copies of nucleic acid sequences in one or more subject genomes or portions thereof (for example, an infertility marker) as a function of the location of those sequences in a reference genome (for example, a normal human genome). As a result, CGH provides a map of losses and gains in nucleic acid copy number across the entire genome without prior knowledge of specific chromosomal abnormalities. Methods of the invention capitalize on the ability to detect copy number variations without the need for prior knowledge in order to detect potential mutations with infertility significance within patient populations that have unexplained infertility.

The following illustrates use of CGH arrays to identify copy number variants of interest in accordance with methods of the invention.

The study examined female patients undergoing non-donor in vitro fertilization (IVF) cycles. The patients were 38 years old or younger at the time of enrollment, and had no history of carrying a pregnancy beyond the first term before IVF treatment. Each patient had lack of an apparent cause for infertility (i.e. unexplained) after an evaluation of a complete medical history, physical examination, endocrine profile, and the results of an intimate partner's sperm analysis. The patients were divided into two groups. Group A included 11 patients that experienced no live birth or pregnancy beyond the first trimester after 3 or more IVF cycles. Group B included 18 patients that experienced live birth or pregnancy beyond the first trimester through use of IVF therapy.

Figure 9:
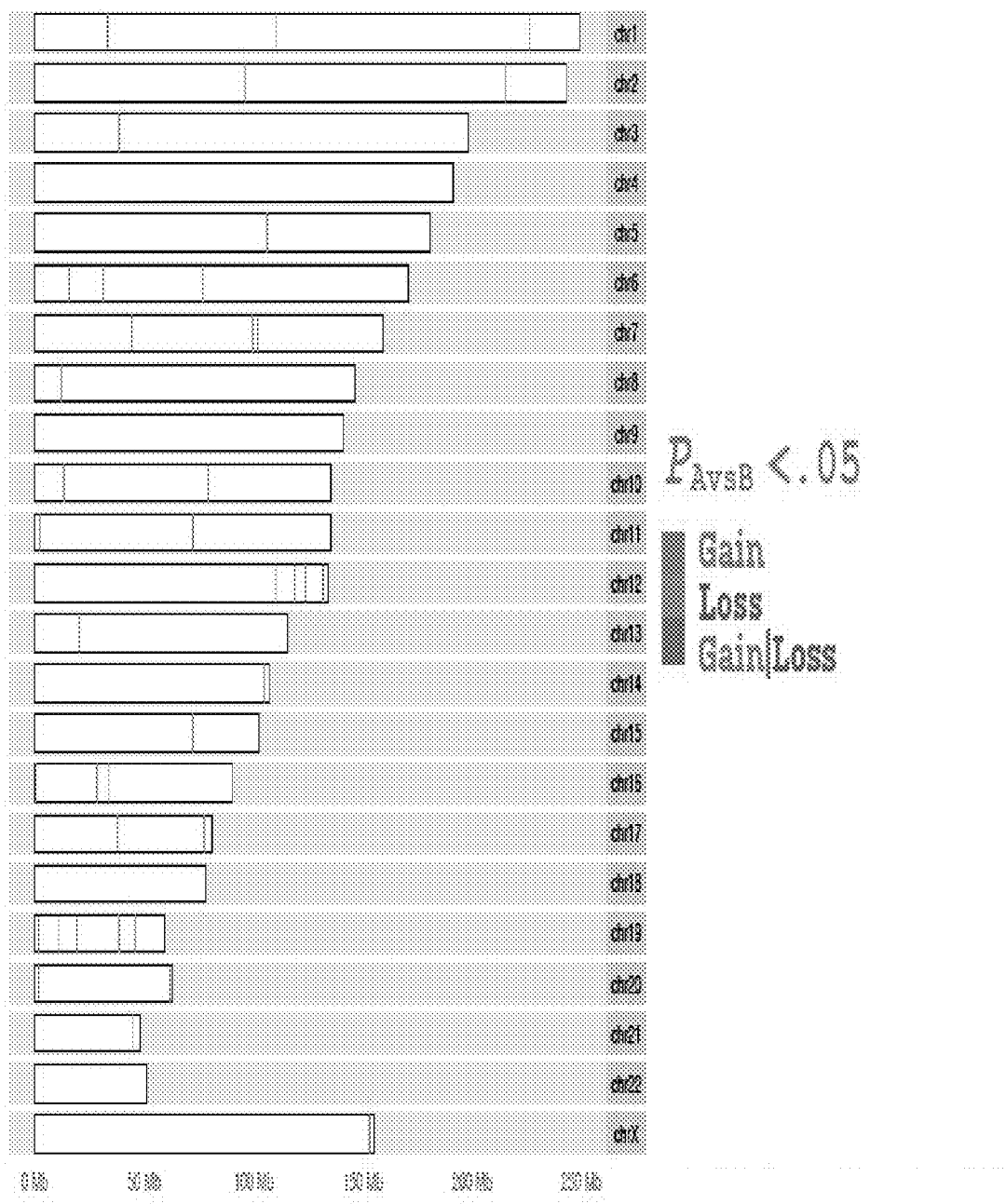
FIG. 9 provides CGH array data of copy number variations associated with infertility.
Figure 10:
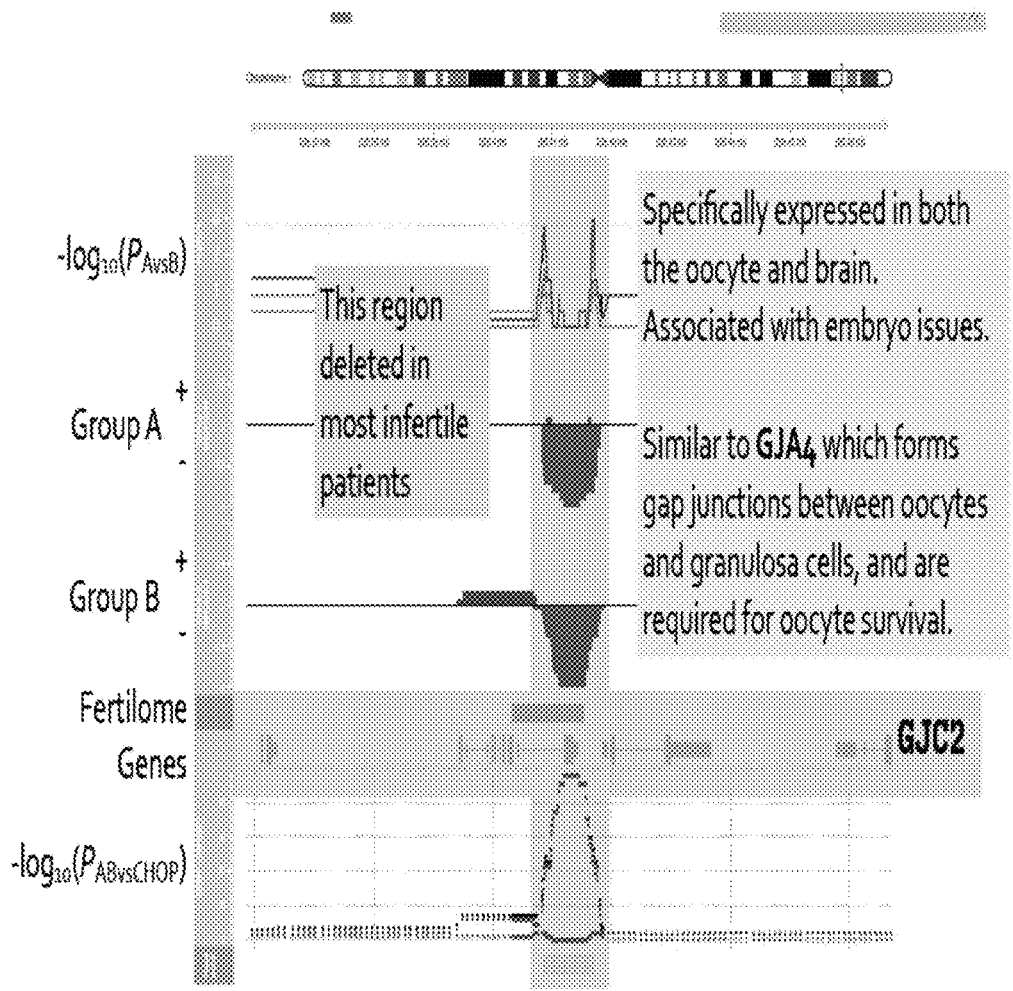
FIG. 10 illustrates a specific copy number variation detected in the GJC2 gene of Chromosome 1.
Figure 11:
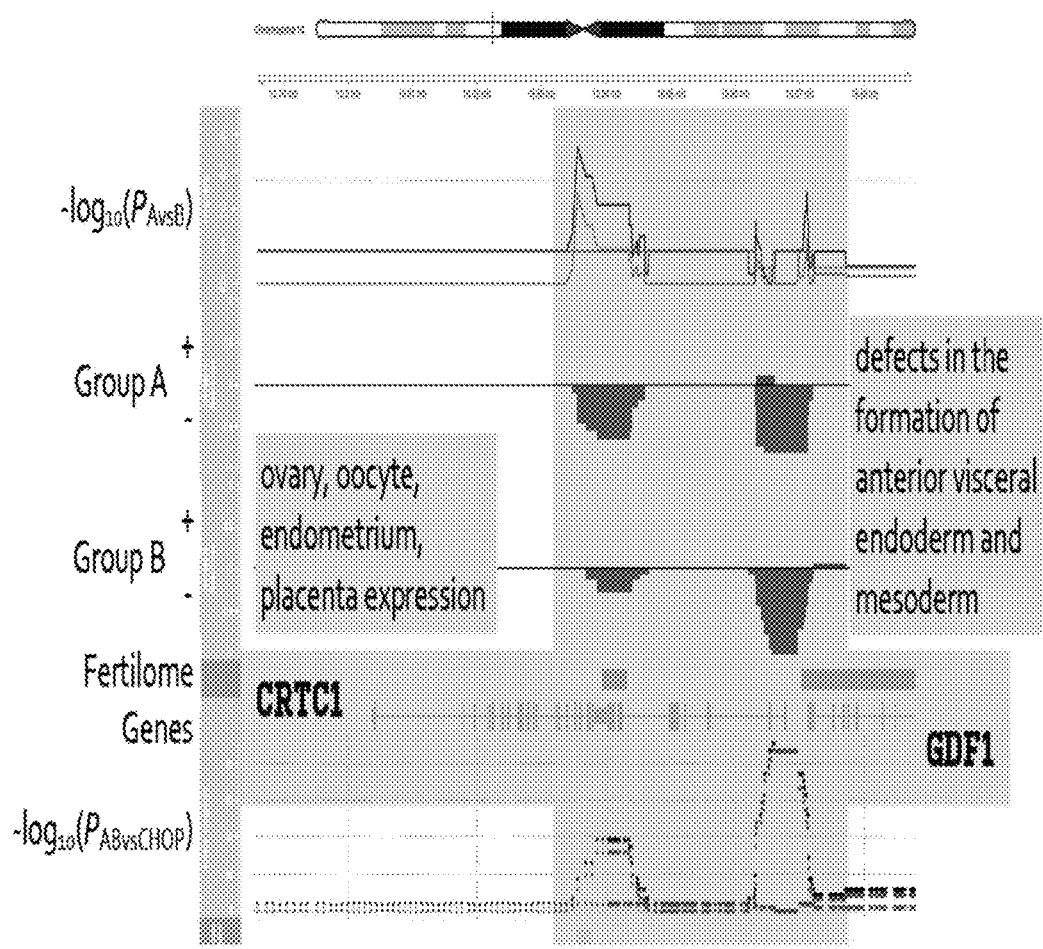
FIG. 11 illustrates a specific copy number variation detected in the CRTC1 and GDF1 genes of Chromosome 19.
Figure 12:
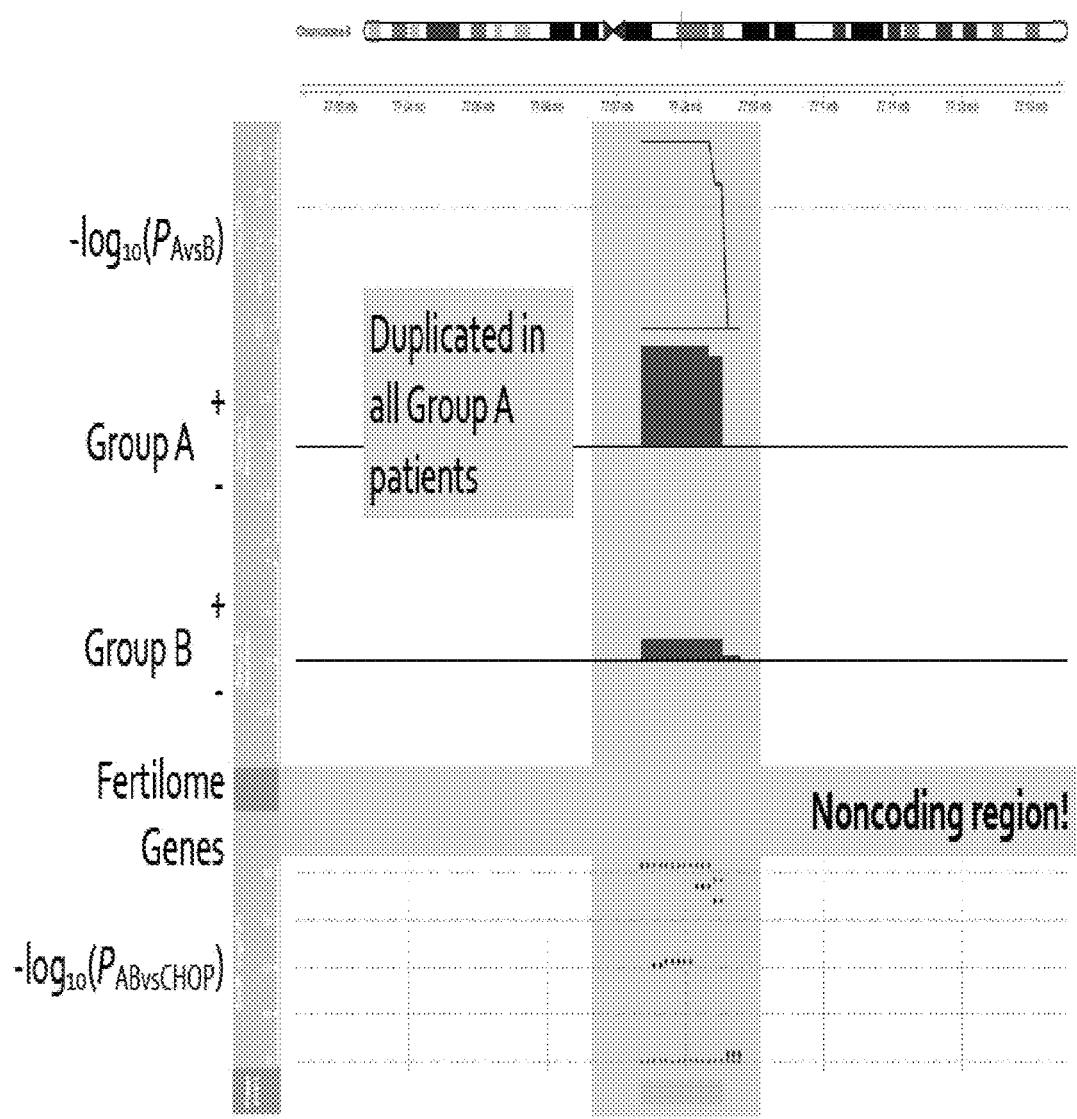
FIG. 12 illustrates a specific copy number variation detected in a non-coding region of Chromosome 6.

FIG. 9 provides CGH array data of copy number variations detected in the study populations within statistically significant regions associated with infertility (i.e. copy number variations within the Fertilome nucleic acid). FIG. 10 illustrates a specific copy number variation detected in the GJC2 gene of Chromosome 1 within Groups A and B. This region is specifically expressed in both the oocyte and brain, and is known to be associated with embryo issues. As shown, the region within GJC2 showed deletion in the most infertile patients. FIG. 11 illustrates a specific copy number variation detected in the CRTC1 and GDF1 genes of Chromosome 19 within Groups A and B. CRTC1 is associated with ovary, oocyte, endometrium, and placenta expression. GDF1 is associated with defects in the formation of anterior visceral endoderm and mesoderm. As shown, both patient groups exhibit copy number deletions in those genes. FIG. 12 illustrates a specific copy number variation detected in a non-coding region of Chromosome 6. As shown, both patient groups exhibit copy number duplication that region.

Example 20

In addition to using the existing infertility knowledge base to identify new genetic variations associated with infertility (e.g., Example 18), methods of the invention further utilize the existing infertility knowledgebase to identify commonalities between known infertility genes and genes having no prior association with infertility. By identifying commonalities between infertility genes and genes having no prior association with infertility, one is able to expand the list of potential genes associated with infertility and guide understanding as to what gene functions and changes are causally-linked to infertility. For example, genes having commonalities with known infertility genes can be identified as potential infertility biomarkers, and used in phenotypic studies (such those performed in mice) related to infertility, thereby expanding the breadth infertility knowledgebase.

In order to determine commonalities between infertility genes and genes without prior associated with infertility, methods of the invention utilize cluster analysis techniques. Generally, a cluster analysis involves grouping a set of objects in such a way that certain objects are clustered in one group are more similar to each other than objects in another group or cluster. Methods of the invention cluster known infertility genes with genes not associated with infertility based on features such as gene expression, phenotype, and genetic pathways. From the cluster analysis, one can identify genes without prior association with infertility that exhibit features with a high degree of similarity (relatedness) to infertility genes. Those genes exhibiting a high degree of similarity (as shown through the cluster analysis) can be identified as a potential infertility biomarker.

The following describes a clustering method used to identify a potential infertility biomarker in accordance with methods of the invention. The method is typically a computer-implemented method, e.g. utilizes a computer system that includes a processor and a computer readable storage medium. The processor of the computer system executes instructions obtained from the computer-readable storage device to perform the cluster analysis.

In accordance with to certain aspects, the method involves obtaining a gene data set that includes both known infertility genes and genes having no prior association with infertility. In certain embodiments, the gene data sets may be taken from known infertility databases, sequencing data obtained from patients, or sequencing data obtained from mouse modeling studies. The genes forming the cluster data set (those associated with infertility and those not known to be associated with infertility) are typically mammalian genes. The mammalian genes may correspond to mouse genes, human, genes, or a combination thereof. A cluster analysis is then performed on the gene data set to determine a relationship between the one or more genes not associated with infertility and the known infertility genes. If a gene not associated with infertility is shown to cluster with a known infertility gene, the method provides for identifying that gene as a potential infertility biomarker. If the gene not associated with infertility does not cluster with a known infertility gene, then that gene is less likely to be causally linked to infertility in the same/similar manner as that known infertility gene.

Methods of the invention assess several features (or parameters) of genes in order to determine commonalities and thus cluster genes not associated with infertility with known infertility genes based on the commonalities. In certain embodiments, those features include gene expression, phenotypes, gene pathways, and a combination thereof. One or more of those features can contribute to a gene's position in the clustering.

Feature data (such as gene expression, phenotype, gene pathway, etc.) is obtained for both known infertility genes and genes not known to be associated with infertility. The feature and gene data is compiled to form a matrix that will be used to exhibit the cluster analysis. For example, the feature data is pre-processed to express each domain as a row and each feature as a column (or vice versa). For domains with continuous values such as gene expression, the features are the individual tissues where gene expression was measured, and each value in the matrix (Xij) represents the expression of gene i in tissue j. For domains with categorical values such as phenotypes, the features are the individual phenotypes, and each value in the matrix (Xij) is a binary indicator representing whether gene i is associated with phenotype j. All of the domain specific matrices are then combined column-wise. A distance metric is then applied to each pair of rows and each pair of columns in the matrix. In certain embodiments, the distance metric is 'Distance=1-correlation'. However, it is understood that other standard distance metrics could be used (e.g. Euclidean).

Standard hierarchical clustering is then used to cluster the rows and columns of the matrix in order to determine feature commonalities between known infertility genes and other genes. Various hierarchical clustering techniques are known in the art, and can be applied to methods of the invention for clustering infertility genes with genes not associated with infertility. Hierarchical clustering techniques are described in, for example, Sturn, Alexander, John Quackenbush, and Zlatko Trajanoski. "Genesis: cluster analysis of microarray data." Bioinformatics 18.1 (2002): 207-208; Yeung, Ka Yee, and Walter L. Ruzzo. "Principal component analysis for clustering gene expression data." Bioinformatics 17.9 (2001): 763-774; Eisen, Michael B., et al. "Cluster analysis and display of genome-wide expression patterns." Proceedings of the National Academy of Sciences 95.25 (1998): 14863-14868. Generally, clustering involves comparing features of one or more genes not associated with features of one or more known infertility, and categorizing the genes into one or more feature groups based on the comparison. After the comparison, the cluster analysis may further involve assigning a value to the categorized genes based on a degree of relatedness. For example, genes clustered together having highly similar or the same features may be assigned a high value (e.g. positive integer). The degree of relatedness may be highlighted on the resulting cluster matrix via colors, e.g. high degree of commonality being shown in red and low degree of commonality being shown in blue.

After a hierarchical clustering technique is applied to the gene/feature data, the gene clusters are displayed against certain feature categories (e.g. phenotype/gene expression 'category'), which are then clustered to reflect commonality. For example, phenotypes of female reproduction are grouped together in one cluster, and phenotypes of embryo patterning, morphology and growth are grouped in a separate cluster, etc. The degree of relatedness or commonality between clustered genes (as determined by the cluster analysis) can then be highlighted on the resulting cluster matrix. For example, red may be used to indicate that the gene is associated with one very specific phenotype and/or is expressed at high levels in the associated tissue/physiological system indicated on the opposite axis; whereas blue may be used to indicate that the gene is associated with a number of different and varied phenotypes and/or is expressed at low levels in the associated tissue.

By clustering genes into feature specific groups and color-coding genes with high degree of relatedness, the resulting cluster matrix of the invention advantageously allows for visualization of groups of genes that are strongly associated with phenotypes relating to particular tissues or physiological systems (i.e. clusters of interest). Thus, cluster matrices of the invention allow one to quickly identify genes without prior association with infertility as potential infertility biomarkers based on their shown association (cluster) with known infertility biomarkers. This clustering and identification of potential infertility biomarkers is done independently from and without correlating a gene's proximity with other genes within or location on the Fertilome (genomic region associated with infertility). As a result, clustering provides an additional method of identifying infertility genes of interest that can be used to complement and in addition to other techniques for identifying infertility genes of interest.

The following describes a specific example of using the above described cluster analysis to correlate genes not known to be associated with infertility and a known infertility gene.

Activin receptor 2b (ACVR2B) is a significant copy number variation identified in a cohort of patients with infertility (i.e. copy number variation in this gene was identified as being significantly associated with an infertile phenotype in humans). Activin receptor 2B is the receptor bound by Activin, a protein previously known in the art to be involved in both human and mouse reproduction and embryonic development. Activin/Nodal signaling regulates pluripotency and several aspects of patterning during early embryogenesis. Together with Inhibin and Follistatin, Activin is also involved in the complex feedback loops that selectively regulate FSH secretion.

Figure 14:
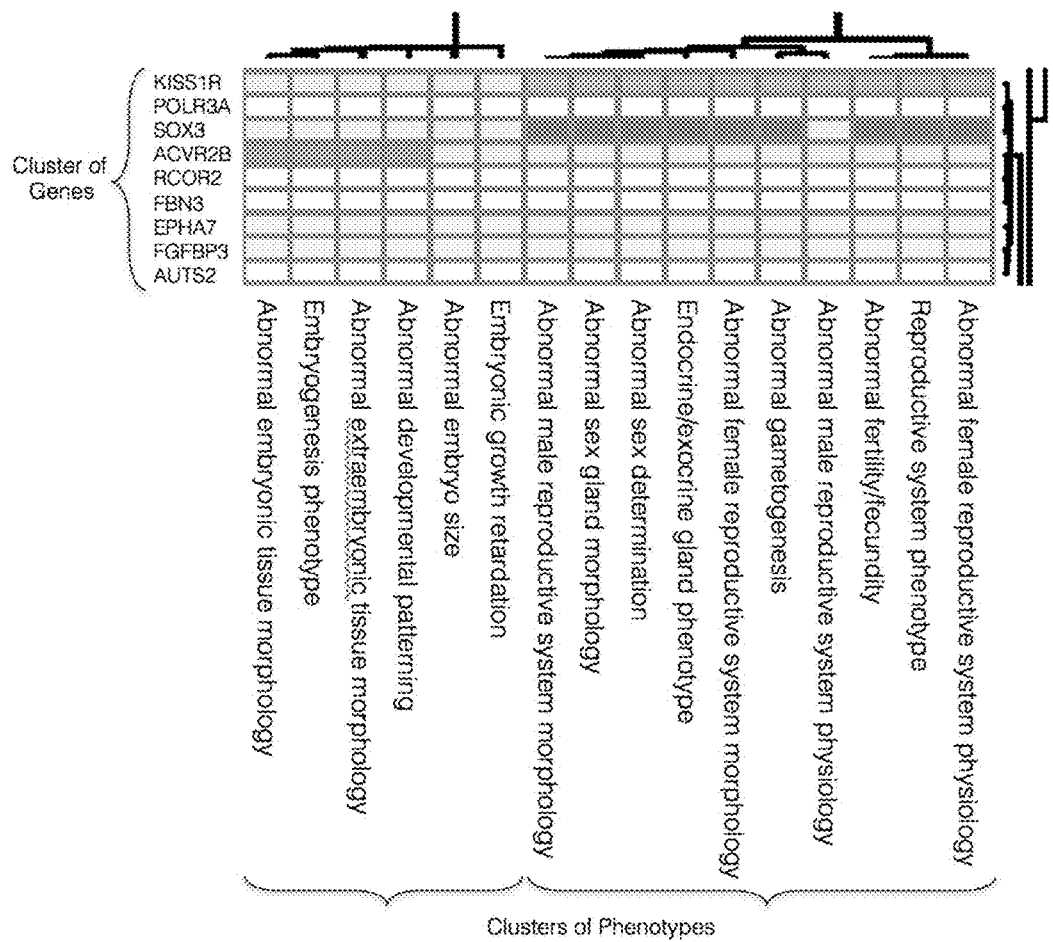
FIG. 14 exemplifies a cluster analysis according to certain aspects.

A cluster analysis was performed that compared those features of ACVR2B and features of a plurality of genes not known to be associated with infertility. Based on the cluster analysis, several of the plurality of genes were determined to cluster with the ACVR2B gene due to a commonality between functional and phenotypic features. The genes clustered with the ACVR2B gene were thus identified as potential infertility biomarkers. FIG. 14 illustrates the results of a cluster analysis with ACVR2B.

What is claimed is:

1. A system for identifying a potential infertility biomarker, the system comprising:
 a processor; and
 a computer-readable storage device containing instructions that when executed by the processor cause the system to:
 receive sequencing data from one or more sequencers communicatively coupled to processor, the sequencing data obtained by assaying a biological sample from a female having a clinical diagnosis of idiopathic infertility;
 receive data on a set of genes from one or more infertility databases communicatively coupled to the processor, wherein the sequencing data and the data form multi-modal data comprising genes known to be associated with infertility and genes having no prior association with infertility, and wherein the multi-modal data comprises one or more features for each gene selected from the group consisting of a phenotype, a gene expression pattern, a genetic pathway, and a combination thereof;
 perform a cluster analysis on the multi-modal data to identify one or more of the genes having no prior association with infertility that cluster with one or more of the genes known to be associated with infertility, the cluster analysis based on feature commonalities between the genes that have no prior association and the genes known to be associated with infertility; and
 provide an output via a display unit that identifies at least one of the genes having no prior association with infertility as a potential infertility biomarker based on it clustering with one or more genes known to be associated with infertility.

2. The system of claim 1, wherein the cluster analysis comprises the steps of
 identifying at least one feature of one or more of the genes known to be associated with infertility;
 analyzing one or more of the genes having no prior association with infertility for the corresponding feature; and
 comparing the at least one feature of the genes known to be associated with infertility with the corresponding feature of the genes having no prior association with infertility to identify feature commonalities.

3. The system of claim 2, wherein the cluster analysis further comprises categorizing the one or more genes having no prior association with infertility into one or more feature groups based on the comparison.

4. The system of claim 3, wherein the cluster analysis further comprises assigning a value to the categorized genes based on a degree of relatedness.

5. The system of claim 1, wherein the one or more genes having no prior association with infertility are mammalian genes.

6. The system of claim 1, wherein the mammalian genes correspond to a species selected from mouse, human, and a combination thereof.

7. The system of claim 1, wherein the genes known to be associated with infertility are mammalian genes.

8. The system of claim 7, wherein the mammalian genes correspond to a species selected from mouse, human, and a combination thereof.

9. The system of claim 1, wherein the cluster analysis comprises:
 compiling the multi-modal data to form a matrix that will be used to exhibit the cluster analysis, wherein each domain is expressed as a row and each feature is expressed as a column;
 applying a distance metric to each pair of rows and each pair of columns in the matrix;
 clustering, using hierarchical clustering, the rows and columns of the matrix in order to determine feature commonalities between the genes known to be associated with infertility and the genes having no prior association with infertility.

10. A computer-implemented method for identifying a potential infertility biomarker, the method comprising:
 assaying a biological sample from a female having a clinical diagnosis of idiopathic infertility to obtain sequencing data;
 receiving to a computer, multi-modal data on a set of genes including data obtained from at least one infertility-associated database and the sequencing data, wherein the set comprising genes known to be associated with infertility and genes having no prior association with infertility and wherein the multi-modal data comprises one or more features for each gene selected from the group consisting of a phenotype, a gene expression pattern, a genetic pathway, and a combination thereof;
 performing on the computer a cluster analysis to identify one or more of the genes having no prior association with infertility that cluster with one or more of the genes known to be associated with infertility the cluster analysis based on feature commonalities between the genes that have no prior association and the genes known to be associated with infertility; and
 identifying at least one of the genes having no prior association with infertility as a potential infertility biomarker based on it clustering with one or more genes known to be associated with infertility.

11. The computer-implemented method of claim 10, wherein the cluster analysis comprises the steps of:
 identifying at least one feature of one or more of the genes known to be associated with infertility;
 analyzing one or more of the genes having no prior association with infertility for a corresponding feature; and
 comparing the at least one feature of the genes known to be associated with infertility with the corresponding feature of the genes having no prior association with infertility to identify feature commonalities.

12. The computer-implemented method of claim 11, wherein the cluster analysis further comprises categorizing the one or more genes having no prior association with infertility into one or more feature groups based on the comparison.

13. The computer-implemented method of claim 12, wherein the cluster analysis further comprises assigning a value to the categorized genes based on a degree of relatedness.

14. The computer-implemented method of claim 10, wherein the one or more genes having no prior association with infertility are mammalian genes.

15. The computer-implemented method of claim 14, wherein the mammalian genes correspond to a species selected from mouse, human, and a combination thereof.

16. The computer-implemented method of claim 10, wherein the genes known to be associated with infertility are mammalian genes.

17. The computer-implemented method of claim 16, wherein the mammalian genes correspond to a species selected from mouse, human, and a combination thereof.

18. The computer-implemented method of claim 11, wherein the cluster analysis comprises:
   compiling the multi-modal data to form a matrix that will be used to exhibit the cluster analysis, wherein each domain is expressed as a row and each feature is expressed as a column;
   applying a distance metric to each pair of rows and each pair of columns in the matrix;
   clustering, using hierarchical clustering, the rows and columns of the matrix in order to determine feature commonalities between the genes known to be associated with infertility and the genes having no prior association with infertility.

* * * * *